(12) United States Patent
Rehwinkel et al.

(10) Patent No.: US 8,097,627 B2
(45) Date of Patent: *Jan. 17, 2012

(54) MULTIPLY-SUBSTITUTED TETRAHYDRONAPHTHALENE DERIVATIVES, PROCESS FOR THEIR PRODUCTION AND THEIR USE AS ANTI-INFLAMMATORY AGENTS

(75) Inventors: Hartmut Rehwinkel, Berlin (DE); Stefan Baeurle, Berlin (DE); Markus Berger, Berlin (DE); Norbert Schmees, Berlin (DE); Heike Schaecke, Berlin (DE); Konrad Krolikiewicz, Berlin (DE); Anne Mengel, Berlin (DE); Duy Nguyen, Berlin (DE); Stefan Jaroch, Berlin (DE); Werner Skuballa, Berlin (DE)

(73) Assignee: Bayer Pharma AG, Berlin (DE)

( * ) Notice: Subject to any disclaimer, the term of this patent is extended or adjusted under 35 U.S.C. 154(b) by 14 days.

This patent is subject to a terminal disclaimer.

(21) Appl. No.: 12/642,121

(22) Filed: Dec. 18, 2009

(65) Prior Publication Data

US 2010/0144742 A1 Jun. 10, 2010

Related U.S. Application Data

(63) Continuation of application No. 12/036,635, filed on Feb. 25, 2008, now abandoned, which is a continuation of application No. 10/961,375, filed on Oct. 12, 2004, now abandoned, which is a continuation-in-part of application No. 10/960,754, filed on Oct. 8, 2004, now Pat. No. 7,659,297.

(60) Provisional application No. 60/560,014, filed on Apr. 7, 2004.

(30) Foreign Application Priority Data

Apr. 5, 2004 (DE) .................. 10 2004 017 662

(51) Int. Cl.
| | |
|---|---|
| A61K 31/50 | (2006.01) |
| A61K 31/517 | (2006.01) |
| A61K 31/47 | (2006.01) |
| C07D 237/30 | (2006.01) |
| C07D 287/72 | (2006.01) |
| C07D 217/22 | (2006.01) |
| C07D 215/02 | (2006.01) |

(52) U.S. Cl. ............... 514/248; 514/266.1; 514/309; 514/312; 544/237; 544/287; 546/141; 546/153

(58) Field of Classification Search .......... 514/248, 514/266.1, 309, 312; 544/237, 287; 546/141, 546/153

See application file for complete search history.

(56) References Cited

U.S. PATENT DOCUMENTS

| | | | |
|---|---|---|---|
| 3,907,879 A | 9/1975 | Murakami et al. | |
| 5,059,609 A | 10/1991 | Eggler et al. | |
| 5,112,834 A | 5/1992 | Senn-Bilfinger | |
| 5,446,069 A | 8/1995 | Shih et al. | |
| 5,489,584 A | 2/1996 | Vuligonda et al. | |
| 6,197,783 B1 | 3/2001 | Senn-Bilfinger et al. | |
| 6,897,224 B2 | 5/2005 | Jaroch et al. | |
| 7,348,322 B2 | 3/2008 | Gong et al. | |
| 7,659,297 B2 * | 2/2010 | Rehwinkel et al. | 514/403 |
| 2003/0199690 A1 | 10/2003 | Dahanukar et al. | |
| 2005/0090559 A1 | 4/2005 | Berger | |
| 2005/0171109 A1 | 8/2005 | Rehwinkel et al. | |
| 2005/0209324 A1 | 9/2005 | Rehwinkel et al. | |
| 2005/0222154 A1 | 10/2005 | Rehwinkel et al. | |
| 2005/0272823 A1 | 12/2005 | Rehwinkel et al. | |
| 2006/0040933 A1 | 2/2006 | Jaroch et al. | |
| 2006/0084652 A1 | 4/2006 | Baeurle et al. | |
| 2006/0165915 A1 | 7/2006 | Lietzau et al. | |
| 2006/0167025 A1 | 7/2006 | Berger | |
| 2006/0202163 A1 | 9/2006 | Lietzau et al. | |
| 2006/0229305 A1 | 10/2006 | Berger et al. | |
| 2006/0247292 A1 | 11/2006 | Rehwinkel et al. | |
| 2007/0015750 A1 | 1/2007 | Baeurle et al. | |
| 2007/0015761 A1 | 1/2007 | Mengel et al. | |
| 2007/0129359 A1 | 6/2007 | Huwe et al. | |
| 2007/0225290 A1 | 9/2007 | Berger et al. | |
| 2008/0153859 A1 | 6/2008 | Rehwinkel et al. | |

FOREIGN PATENT DOCUMENTS

| | | |
|---|---|---|
| CN | 1524835 A | 9/2004 |
| EP | 0291327 A2 | 11/1988 |
| EP | 0299470 A1 | 1/1989 |
| EP | 0439265 | 7/1991 |

(Continued)

OTHER PUBLICATIONS

Int'l. Search Report dated issued Jan. 18, 2006 in PCT/EP2005/009623.

Evans, D.A. et al., "C2-symmetric copper (II) complexes as chiral lewis acids. Catalytic enantioselective carbonyl-ene reactions with glyoxylate and pyruvate esters," Journal of the American Chemical Society, 2000, pp. 7936-7943, vol. 122, Washington, D.C.

(Continued)

*Primary Examiner* — James O Wilson
*Assistant Examiner* — Ebenezer O Sackey
(74) *Attorney, Agent, or Firm* — Millen, White, Zelano & Branigan, P.C.

(57) ABSTRACT

The invention relates to multiply-substituted tetrahydronaphthalene derivatives of formula (I)

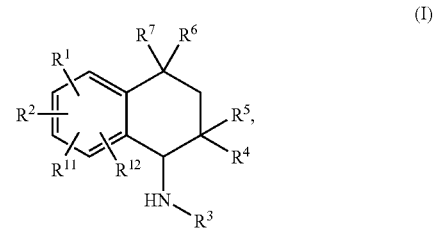

process for their production and their use as anti-inflammatory agents.

18 Claims, No Drawings

FOREIGN PATENT DOCUMENTS

| | | |
|---|---|---|
| EP | 05/79223 A1 | 1/1994 |
| JP | 63220242 A | 9/1988 |
| JP | 2000/256255 A2 | 9/2000 |
| WO | WO 88/08836 A2 | 11/1988 |
| WO | WO 96/20930 A | 7/1996 |
| WO | WO 99/04778 A1 | 2/1999 |
| WO | WO 99/06388 A2 | 2/1999 |
| WO | WO 99/37607 A1 | 7/1999 |
| WO | WO 99/50205 A2 | 10/1999 |
| WO | WO 00/10977 A1 | 3/2000 |
| WO | WO 01/30734 A1 | 5/2001 |
| WO | WO 02/10143 A | 2/2002 |
| WO | WO 02/16318 | 2/2002 |
| WO | WO 03/000694 A1 | 1/2003 |
| WO | WO 03/027061 A2 | 4/2003 |
| WO | WO 03/040107 A1 | 5/2003 |
| WO | WO 03/045924 A1 | 6/2003 |
| WO | WO 03/082280 A | 10/2003 |
| WO | WO 03/082827 A | 10/2003 |
| WO | WO 2004/020375 A1 | 3/2004 |
| WO | WO 2004/063163 A | 7/2004 |
| WO | WO 2004/075864 A | 9/2004 |
| WO | WO 2005/003098 A1 | 1/2005 |
| WO | WO 2005/021682 A1 | 3/2005 |
| WO | WO 2006/027236 A | 3/2005 |
| WO | WO 2005/034939 A | 4/2005 |
| WO | WO 2005/090343 A | 9/2005 |
| WO | WO 2006/015870 A | 2/2006 |
| WO | WO 2006/066950 A | 6/2006 |
| WO | WO 2006/100100 A | 9/2006 |
| WO | WO 2006/108699 A | 10/2006 |
| WO | WO 2006/108714 A | 10/2006 |

OTHER PUBLICATIONS

Cleghorn, L.A.T. et al., "Three-component bimetallic (pd/ln) mediated cascade allylation of C=X functionality—Part 1. Scope and class 1 examples with aldehydes and ketones," Journal of Organometallic Chemistry, Dec. 7, 2003, pp. 483-493, vol. 687 No. 2. Elsevier-sequoia S.A. Lausanne, CH.

Ene reaction, Wikipedia.

Inflammation, Wikipedia, p. 1-11.

Noseworthy et al., The New England Journal of Medicine, p. 949, vol. 343, No. 13, (2005).

Jordan, V.C. Nature Reviews: Drug Discovery, 2, 2003, p. 205.

Dorwald, F. Zaragoza. Side Reactions in Organic Synthesis: A Guide to Sucessful Synthesis Design, Weinheim: WILEY-VCH Verlag Gmbh & Co. KgaA, 2005, Preface.

Database CA (ONLINE), Chemical Abstracts Service, Columbus, OH, 2004. Patonay, Tamas et al., "Synthesis of racemic and enantiomerically enriched .alpha-Osyfunctionalized benzocyclanones and chromanones by dimethyldioxirane and dimethyldioxirane/Mn(III) salen system," XP002397131.

Database CA (ONLINE), Chemical Abstracts Service, Columbus, OH, 2001. Ferraz, Helena et al., "The reaction of 1-tetralones with thallium trinitrate supported on clay : ring contraction vs. .alpha.-oxidation," XP002397132.

Database CA (ONLINE), Chemical Abstracts Services, Columbus, OH, 1994. Srivastava, J.N. et al., "Syntheisis of 7-methoxy- and 6-mthoxytatralino[3,4-c]isocumarins and 7-methoxy- and 6-methoxytetralino[3,4-c]isoquinolones," XP002397133.

Database CA (ONLINE), Chemical Abstracts Service, Columbus, OH, 1983. Thiem, Joachim et al., "2, 6-dideoxy sacchride glycosides of .alpha.-hydroxy ketones: synthesis and configurational assignment of glycosides with the tetralone substructure of olivomycin," XP 002397135.

Chemical Abstracts 138:385424, 138:287411, 143:193936, 141:218306, 140:357328, 134:326287, 134:71375, 126:34370, 89:42860.

Cecil Textbook of Medicine, edited by Bennet, J.C., and Plum F., $20^{th}$ edition, vol. 1m 1004-1010, 1996.

Smoak et al., Mechanism of Ageing and Development, 125 697-706, 2004.

Saklavaia et al., Arthritis Research 4(3), 146-150, 2002.

Barnes, P.J., Eur. Respir. J., 27(2), 413-426, 2006.

Bellucci et al., Tetrahedron Asymmetry, 8, 895-902, 1997.

Hachisu et al. Thiazolium ylide—catalyzed intramolecular aldehyde-ketone benzoin-forming reactionsl Advanced Synthesis & Catalysis, 2004, col. 346 (9+ 10), pp. 1097-1100: HCAPLUS abstract, Doc. No. 142:260997.

Dehmlow et al. Monodeazacinchona Alkaloid Derivatives: Synthesis and Preliminary Applications as Phase-Transfer Catalyst European Journal of Organic Chemistry, 2002 (13), pp. 2087-2093.

Nagao et al. New Ring-Expansion Reactions of Hydroxy Propenoyl Cyclic Compounds under Palladium (O)/Phosine-Catalyzed Conditions. Organic Letters, 2004, vol. 6 (13), pp. 2133-2136.

Greene, Protective Groups in Organic Synthesis, 1999, pp. 17-23.

Warner-Lambert. Expert Opinion on Therapeutic Patents, 2000, 10 (1), 121-23.

Int'l Search Report dated issued Feb. 8, 2002 in PCT/EP2007/002432.

Tchilibon et al., Biochemical Pharmacology, 70 (2005), 381-393.

Office Action dated Oct. 3, 2007 in related U.S. Appl. No. 10/962,169, filed Oct. 12, 2004.

Office Action dated Oct. 2, 2007 in related U.S. Appl. No. 10/961,406, filed Oct. 12, 2004.

Office Action dated Apr. 24, 2007 in related U.S. Appl. No. 11/222,250, filed Sep. 9, 2005.

* cited by examiner

MULTIPLY-SUBSTITUTED TETRAHYDRONAPHTHALENE DERIVATIVES, PROCESS FOR THEIR PRODUCTION AND THEIR USE AS ANTI-INFLAMMATORY AGENTS

This application is a Continuation of U.S. application Ser. No. 12/036,635, filed. Feb. 25, 2008 now abandoned, which is a Continuation of U.S. application Ser. No. 10/961,375, filed Oct. 12, 2004 now abandoned, which is a Continuation-In-Part of U.S. application Ser. No. 10/960,754, filed Oct. 8, 2004 now U.S. Pat. No. 7,659,297, which claims the benefit of U.S. Application Ser. No. 60/560,014, filed Apr. 7, 2004, all of which are incorporated by reference herein.

The invention relates to multiply-substituted tetrahydronaphthalene derivatives, process for their production and their use as anti-inflammatory agents.

Open-chain, non-steroidal anti-inflammatory agents are known from the prior art (DE 100 38 639 and WO02/10143). In the experiment, these compounds show dissociations of action between anti-inflammatory and undesirable metabolic actions and are superior to the previously described nonsteroidal glucocorticoids or exhibit at least just as good an action.

The selectivity as well as the pharmacokinetic parameters of the compounds of the prior art are still in need of improvement, however.

It was therefore the object of this invention to make available compounds whose selectivity compared to the other steroid receptors as well as their pharmacokinetic properties are at least just as good or better than the compounds of the prior art.

This object is achieved by the compounds of this invention, explained in the claims.

This invention therefore relates to stereoisomers of general formula (I)

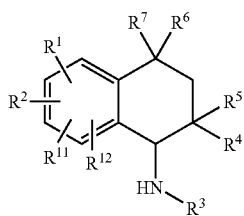

in which
R$^1$ and R$^2$, independently of one another, mean a hydrogen atom, a hydroxy group, a halogen atom, an optionally substituted (C$_1$-C$_{10}$)-alkyl group, an optionally substituted (C$_1$-C$_{10}$)-alkoxy group, a (C$_1$-C$_{10}$)-alkylthio group, a (C$_1$-C$_5$)-perfluoroalkyl group, a cyano group, or a nitro group,
or R$^1$ and R$^2$ together mean a group that is selected from the groups —O—(CH$_2$)$_n$—O—, —O—(CH$_2$)$_n$—CH$_2$—, —O—CH=CH—, —(CH$_2$)$_{n+2}$—, —NH—(CH$_2$)$_{n+1}$, N(C$_1$-C$_3$-alkyl)-(CH$_2$)$_{n+1}$, or —NH—N=CH—,
whereby n=1 or 2, and the terminal oxygen atoms and/or carbon atoms and/or nitrogen atoms are linked to directly adjacent ring-carbon atoms, or NR$^8$R$^9$, whereby R$^8$ and R$^9$, independently of one another, can be hydrogen, C$_1$-C$_5$-alkyl or (CO)—C$_1$-C$_5$-alkyl,
R$^{11}$ means a hydrogen atom, a hydroxy group, a halogen atom, a cyano group, an optionally substituted (C$_1$-C$_{10}$)-alkyl group, a (C$_1$-C$_{10}$)-alkoxy group, a (C$_1$-C$_{10}$)-alkylthio group, or a (C$_1$-C$_5$)-perfluoroalkyl group,
R$^{12}$ means a hydrogen atom, a hydroxy group, a halogen atom, a cyano group, an optionally substituted (C$_1$-C$_{10}$)-alkyl group, or a (C$_1$-C$_{10}$)-alkoxy group,
R$^3$ means a C$_1$-C$_{10}$-alkyl group that optionally is substituted by 1-3 hydroxy groups, halogen atoms, 1-3 (C$_1$-C$_5$)-alkoxy groups, an optionally substituted (C$_3$-C$_7$)-cycloalkyl group, an optionally substituted heterocyclyl group, an optionally substituted aryl group, a monocyclic or bicyclic heteroaryl group that optionally contains 1-4 nitrogen atoms and/or 1-2 oxygen atoms and/or 1-2 sulfur atoms and/or 1-2 keto groups and that optionally is substituted, independently of one another, by one or more groups selected from (C$_1$-C$_5$)-alkyl groups (which optionally can be substituted by 1-3 hydroxy groups or 1-3 COOR$^{13}$ groups, whereby R$^{13}$ means hydrogen or (C$_1$-C$_5$)-alkyl); (C$_1$-C$_5$)-alkoxy groups, halogen atoms, hydroxy groups, NR$^8$R$^9$ groups, exomethylene groups, or oxygen, whereby this group can be linked via any position to the amine of the tetrahydronaphthalene system and optionally can be hydrogenated at one or more locations,
R$^4$ means a hydroxy group, a group OR$^{10}$, or an O(CO)R$^{10}$ group, whereby R$^{10}$ means any hydroxy protective group or a C$_1$-C$_{10}$-alkyl group,
R$^5$ means a (C$_1$-C$_{10}$)-alkyl group or an optionally partially or completely fluorinated (C$_1$-C$_{10}$)-alkyl group, a (C$_3$-C$_7$)cycloalkyl group, a (C$_1$-C$_8$)alkyl(C$_3$-C$_7$)cycloalkyl group, a (C$_2$-C$_8$)alkenyl(C$_3$-C$_7$)cycloalkyl group, a heterocyclyl group, a (C$_1$-C$_8$)alkylheterocyclyl group, a (C$_2$-C$_8$)-alkenylheterocyclyl group, an aryl group, a (C$_1$-C$_8$)alkylaryl group, a (C$_2$-C$_8$)alkenylaryl group, (C$_2$-C$_8$)alkinylaryl groups,
a monocyclic or bicyclic heteroaryl group that contains 1-3 nitrogen atoms and/or 1-2 oxygen atoms and/or 1-2 sulfur atoms and that optionally is substituted by 1-2 keto groups, 1-2 (C$_1$-C$_5$)-alkyl groups, 1-2 (C$_1$-C$_5$)-alkoxy groups, 1-3 halogen atoms or 1-2 exomethylene groups; a (C$_1$-C$_8$)alkylheteroaryl group or a (C$_2$-C$_8$)alkenylheteroaryl group, or a (C$_2$-C$_8$)alkinylheteroaryl group, whereby these groups can be linked via any position to the tetrahydronaphthalene system and optionally can be hydrogenated at one or more locations,
R$^6$ and R$^7$, independently of one another, mean a hydrogen atom, a methyl or ethyl group or together with the carbon atom of the tetrahydronaphthalene system mean a (C$_3$-C$_6$)-cycloalkyl ring,
provided that at least three of radicals R$^1$, R$^2$, R$^{11}$ and R$^{12}$ are not hydrogen.

Stereoisomers of general formula (I), in which
R$^1$ and R$^2$, independently of one another, mean a hydrogen atom, a hydroxy group, a halogen atom, an optionally substituted (C$_1$-C$_{10}$)-alkyl group, a (C$_1$-C$_{10}$)-alkoxy group, a (C$_1$-C$_{10}$)-alkylthio group, a (C$_1$-C$_5$)-perfluoroalkyl group, a cyano group, or a nitro group, or R$^1$ and R$^2$ together mean a group that is selected from the groups —O—(CH$_2$)$_n$—O—, —O—(CH$_2$)$_n$—CH$_2$—, —O—CH=CH—, —(CH$_2$)$_{n+2}$—, —NH—(CH$_2$)$_{n+1}$, —N(C$_1$-C$_3$-alkyl)-(CH$_2$)$_{n+1}$—, and —NH—N=CH—,
whereby n=1 or 2, and the terminal oxygen atoms and/or carbon atoms and/or nitrogen atoms are linked to directly adjacent ring-carbon atoms, or NR$^8$R$^9$,
whereby R$^8$ and R$^9$, independently of one another, can be hydrogen, C$_1$-C$_5$-alkyl or (CO)—C$_1$-C$_5$-alkyl, $R^{11}$ means a hydrogen atom, a hydroxy group, a halogen atom, a cyano group, an optionally substituted ($C_1$-$C_{10}$)-alkyl group, a ($C_1$-$C_{10}$)-alkoxy group, a ($C_1$-$C_{10}$)-alkylthio group, or a ($C_1$-$C_5$)-perfluoroalkyl group, $R^{12}$ means a hydrogen atom, a hydroxy group, a halogen atom, a cyano group, an optionally substituted ($C_1$-$C_{10}$)-alkyl group, or a ($C_1$-$C_{10}$)-alkoxy group, $R^3$ means a $C_1$-$C_{10}$-alkyl group that optionally is substituted by 1-3 hydroxy groups, halogen atoms, or 1-3 ($C_1$-$C_5$)-alkoxy groups, an optionally substituted ($C_3$-$C_7$)-cycloalkyl group, an optionally substituted heterocyclyl group, an optionally substituted aryl group, a monocyclic or bicyclic heteroaryl group that optionally contains 1-3 nitrogen atoms and/or 1-2 oxygen atoms and/or 1-2 sulfur atoms and/or 1-2 keto groups and that optionally is substituted by one or more groups that are selected from ($C_1$-$C_5$)-alkyl groups (which optionally can be substituted by 1-3 hydroxy groups or 1-3 $COOR^{13}$ groups, whereby $R^{13}$ means hydrogen or ($C_1$-$C_5$)-alkyl), ($C_1$-$C_5$)-alkoxy groups, halogen atoms, or exomethylene groups, whereby this group can be linked via any position to the amine of the tetrahydronaphthalene system and optionally can be hydrogenated at one or more locations, $R^4$ means a hydroxy group, a group $OR^{10}$ or an $O(CO)R^{10}$ group, whereby $R^{10}$ means any hydroxy protective group or a $C_1$-$C_{10}$-alkyl group, $R^5$ means a ($C_1$-$C_5$)-alkyl group or an optionally partially or completely fluorinated ($C_1$-$C_5$)-alkyl group, a ($C_3$-$C_7$)cycloalkyl group, a ($C_1$-$C_8$)alkyl($C_3$-$C_7$)cycloalkyl group, a ($C_2$-$C_8$)alkenyl($C_3$-$C_7$)cycloalkyl group, a heterocyclyl group, a ($C_1$-$C_8$)alkylheterocyclyl group, a ($C_2$-$C_8$)-alkenylheterocyclyl group, ($C_2$-$C_8$)alkinylaryl groups, an aryl group, a ($C_1$-$C_8$)alkylaryl group, a ($C_2$-$C_8$)alkenylaryl group, a monocyclic or bicyclic heteroaryl group that contains 1-3 nitrogen atoms and/or 1-2 oxygen atoms and/or 1-2 sulfur atoms and that optionally is substituted by 1-2 keto groups, 1-2 ($C_1$-$C_5$)-alkyl groups, 1-2 ($C_1$-$C_5$)-alkoxy groups, 1-3 halogen atoms, or 1-2 exomethylene groups; a ($C_1$-$C_8$)alkylheteroaryl group or a ($C_2$-$C_8$)alkenylheteroaryl group, whereby these groups can be linked via any position to the tetrahydronaphthalene system and optionally can be hydrogenated at one or more locations, $R^6$ and $R^7$, independently of one another, mean a hydrogen atom, a methyl or ethyl group or together with the carbon atom of the tetrahydronaphthalene system mean a ($C_3$-$C_6$)-cycloalkyl ring, provided that at least three of radicals $R^1$, $R^2$, $R^{11}$ and $R^{12}$ are not hydrogen, are another subject of this invention.

In addition, this invention relates to compounds of general formula (I),

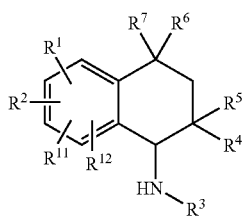

(I)

in which $R^1$ and $R^2$, independently of one another, mean a hydrogen atom, a hydroxy group, a halogen atom, an optionally substituted ($C_1$-$C_{10}$)-alkyl group, a ($C_1$-$C_{10}$)-alkoxy group, a ($C_1$-$C_{10}$)-alkylthio group, a ($C_1$-$C_5$)-perfluoroalkyl group, a cyano group, or a nitro group, or $R^1$ and $R^2$ together mean a group that is selected from the groups —O—$(CH_2)_n$—O—, —O—$(CH_2)_n$—$CH_2$—, —O—CH=CH—, —$(CH_2)_{n+2}$—, —NH—$(CH_2)_{n+1}$, N($C_1$-$C_3$-alkyl)-$(CH_2)_{n+1}$, and —NH—N=CH—, whereby n=1 or 2, and the terminal oxygen atoms and/or carbon atoms and/or nitrogen atoms are linked to directly adjacent ring-carbon atoms, or $NR^8R^9$, whereby $R^8$ and $R^9$, independently of one another, can be hydrogen, $C_1$-$C_5$-alkyl or (CO)—$C_1$-$C_5$-alkyl, $R^{11}$ means a hydrogen atom, a hydroxy group, a halogen atom, a cyano group, an optionally substituted ($C_1$-$C_{10}$)-alkyl group, a ($C_1$-$C_{10}$)-alkoxy group, a ($C_1$-$C_{10}$)-alkylthio group, or a ($C_1$-$C_5$)-perfluoroalkyl group, $R^{12}$ means a hydrogen atom, a hydroxy group, a halogen atom, a cyano group, an optionally substituted ($C_1$-$C_{10}$)-alkyl group, or a ($C_1$-$C_{10}$)-alkoxy group, $R^3$ means a $C_1$-$C_{10}$-alkyl group, which optionally can be substituted by a group that is selected from 1-3 hydroxy groups, halogen atoms, or 1-3 ($C_1$-$C_5$)-alkoxy groups, an optionally substituted ($C_3$-$C_7$)-cycloalkyl group, an optionally substituted heterocyclyl group, an optionally substituted aryl group, a monocyclic or bicyclic heteroaryl group that optionally contains 1-3 nitrogen atoms and/or 1-2 oxygen atoms and/or 1-2 sulfur atoms and/or 1-2 keto groups and that optionally is substituted by one or more groups that are selected from ($C_1$-$C_5$)-alkyl groups (which optionally can be substituted by 1-3 hydroxy groups or 1-3 $COOR^{13}$ groups, whereby $R^{13}$ means hydrogen or ($C_1$-$C_5$)-alkyl), ($C_1$-$C_5$)-alkoxy groups, halogen atoms, or exomethylene groups, whereby this group can be linked via any position to the amine of the tetrahydronaphthalene system and optionally can be hydrogenated at one or more locations, $R^4$ means a hydroxy group, a group $OR^{10}$ or an $O(CO)R^{10}$ group, whereby $R^{10}$ means any hydroxy protective group or a $C_1$-$C_{10}$-alkyl group, $R^5$ means a ($C_1$-$C_5$)-alkyl group or an optionally partially or completely fluorinated ($C_1$-$C_5$)-alkyl group, a ($C_3$-$C_7$)cycloalkyl group, a ($C_1$-$C_8$)alkyl($C_3$-$C_7$)cycloalkyl group, a ($C_2$-$C_8$)alkenyl($C_3$-$C_7$)cycloalkyl group, a heterocyclyl group, a ($C_1$-$C_8$)alkylheterocyclyl group, a ($C_2$-$C_8$)-alkenylheterocyclyl group, an aryl group, a ($C_1$-$C_8$)alkylaryl group, a ($C_2$-$C_8$)alkenylaryl group, ($C_2$-$C_8$)alkinylaryl groups, a monocyclic or bicyclic heteroaryl group that contains 1-3 nitrogen atoms and/or 1-2 oxygen atoms and/or 1-2 sulfur atoms and that optionally is substituted by 1-2 keto groups, 1-2 ($C_1$-$C_5$)-alkyl groups, 1-2 ($C_1$-$C_5$)-alkoxy groups, 1-3 halogen atoms, or 1-2 exomethylene groups; a ($C_1$-$C_8$)alkylheteroaryl group or a ($C_2$-$C_8$)alkenylheteroaryl group, whereby these groups can be linked via any position to the tetrahydronaphthalene system and optionally can be hydrogenated at one or more locations, $R^6$ and $R^7$, independently of one another, mean a hydrogen atom, a methyl or ethyl group or together with the carbon atom of the tetrahydronaphthalene system mean a ($C_3$-$C_6$)-cycloalkyl ring, provided that at least three of radicals $R^1$, $R^2$, $R^{11}$ and $R^{12}$ are not hydrogen.

Stereoisomers of general formula (I), in which $R^1$ and $R^2$, independently of one another, mean a hydrogen atom, a hydroxy group, a halogen atom, an optionally substituted ($C_1$-$C_{10}$)-alkyl group, an optionally substituted ($C_1$-$C_{10}$)-alkoxy group, a ($C_1$-$C_{10}$)-alkylthio group, a ($C_1$-$C_5$)-perfluoroalkyl group, a cyano group, or a nitro group, or $R^1$ and $R^2$ together mean a group that is selected from the groups —O—$(CH_2)_n$—O—, —O—$(CH_2)_n$—$CH_2$—, —O—CH=CH—, —$(CH_2)_{n+2}$—, —NH—$(CH_2)_{n+1}$, —N($C_1$-$C_3$-alkyl)-$(CH_2)_{n+1}$, and —NH—N=CH—, whereby n=1 or 2, and the terminal oxygen atoms and/or carbon atoms and/or nitrogen atoms are linked to directly adjacent ring-carbon atoms, or $NR^8R^9$, whereby $R^8$ and $R^9$, independently of one another, can be hydrogen, $C_1$-$C_5$-alkyl, or (CO)—$C_1$-$C_5$-alkyl, $R^{11}$ means a hydrogen atom, a hydroxy group, a halogen atom, a cyano group, an optionally substituted ($C_1$-$C_{10}$)-alkyl group, a ($C_1$-$C_{10}$)-alkoxy group, a ($C_1$-$C_{10}$)-alkylthio group, or a ($C_1$-$C_5$)-perfluoroalkyl group, $R^{12}$ means a hydrogen atom, a hydroxy group, a halogen atom, a cyano group, an optionally substituted ($C_1$-$C_{10}$)-alkyl group, or a ($C_1$-$C_{10}$)-alkoxy group, $R^3$ means a $C_1$-$C_{10}$-alkyl group that optionally is substituted by 1-3 hydroxy groups, halogen atoms, 1-3 ($C_1$-$C_5$)-alkoxy groups, an optionally substituted ($C_3$-$C_7$)-cycloalkyl group, an optionally substituted heterocyclyl group, an optionally substituted aryl group, a monocyclic or bicyclic heteroaryl group that optionally contains 1-3 nitrogen atoms and/or 1-2 oxygen atoms and/or 1-2 sulfur atoms and/or 1-2 keto groups and that optionally is substituted, independently of one another, by one or more groups selected from ($C_1$-$C_5$)-alkyl groups (which optionally can be substituted by 1-3 hydroxy groups or 1-3 $COOR^{13}$ groups, whereby $R^{13}$ means hydrogen or ($C_1$-$C_5$)-alkyl), ($C_1$-$C_5$)-alkoxy groups, halogen atoms, hydroxy groups, $NR^8R^9$ groups, exomethylene groups, or oxygen, whereby this group can be linked via any position to the amine of the tetrahydronaphthalene system and optionally can be hydrogenated at one or more locations, $R^4$ means a hydroxy group, a group $OR^{10}$ or an $O(CO)R^{10}$ group, whereby $R^{10}$ means any hydroxy protective group or a $C_1$-$C_{10}$-alkyl group, $R^5$ means a ($C_1$-$C_{10}$)-alkyl group or an optionally partially or completely fluorinated ($C_1$-$C_{10}$)-alkyl group, $R^6$ and $R^7$, independently of one another, mean a hydrogen atom, a methyl or ethyl group, or together with the carbon atom of the tetrahydronaphthalene system mean a ($C_3$-$C_6$)-cycloalkyl ring, provided that at least three of radicals $R^1$, $R^2$, $R^{11}$ and $R^{12}$ are not hydrogen, are another subject of this invention.

Stereoisomers of general formula (I) according to claim 1,

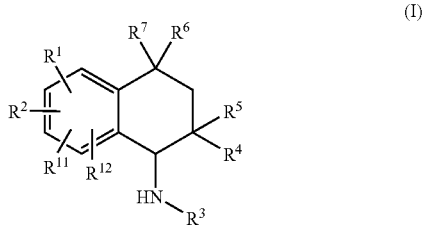

(I)

in which $R^1$ and $R^2$, independently of one another, mean a hydrogen atom, a hydroxy group, a halogen atom, a ($C_1$-$C_{10}$)-alkyl group, a ($C_1$-$C_{10}$)-alkoxy group, a ($C_1$-$C_{10}$)-alkylthio group, a ($C_1$-$C_5$)-perfluoroalkyl group, a cyano group, a nitro group, or $R^1$ and $R^2$ together mean a group that is selected from the groups —O—$(C_2)_n$—O—, —O—$(CH_2)_n$—$CH_2$—, —O—CH=CH—, or —$(CH_2)_{n+2}$—, whereby n=1 or 2, and the terminal oxygen atoms and/or carbon atoms are linked to directly adjacent ring-carbon atoms, or $NR^8R^9$, whereby $R^8$ and $R^9$, independently of one another, can be hydrogen, $C_1$-$C_5$-alkyl or (CO)—$C_1$-$C_5$-alkyl, $R^{11}$ means a hydrogen atom, a hydroxy group, a halogen atom, a cyano group, an optionally substituted ($C_1$-$C_{10}$)-alkyl group, a ($C_1$-$C_{10}$)-alkoxy group, a ($C_1$-$C_{10}$)-alkylthio group, or a ($C_1$-$C_5$)-perfluoroalkyl group, $R^{12}$ means a hydrogen atom, a hydroxy group, a halogen atom, a cyano group, an optionally substituted ($C_1$-$C_{10}$)-alkyl group, or a ($C_1$-$C_{10}$)-alkoxy group, $R^3$ means a $C_1$-$C_{10}$-alkyl group, which optionally can be substituted by a group that is selected from 1-3 hydroxy groups, halogen atoms or 1-3 ($C_1$-$C_5$)-alkoxy groups, an optionally substituted phenyl group or a naphthyl group, a monocyclic or bicyclic heteroaryl group that contains 1-3 nitrogen atoms and/or 1-2 oxygen atoms and/or 1-2 sulfur atoms and that optionally is substituted by 1-2 keto groups, 1-2 ($C_1$-$C_5$)-alkyl groups, 1-2 ($C_1$-$C_5$)-alkoxy groups, 1-3 halogen atoms, or 1-2 exomethylene groups, whereby these groups can be linked via any position to the amine of the tetrahydronaphthalene system and optionally can be hydrogenated at one or more locations, $R^4$ means a hydroxy group, $R^5$ means a ($C_1$-$C_5$)-alkyl group or an optionally partially or completely fluorinated ($C_1$-$C_5$)-alkyl group, an aryl group, a ($C_1$-$C_8$)alkylaryl group, a ($C_2$-$C_8$)alkenylaryl group, a ($C_3$-$C_7$)cycloalkyl group, a ($C_1$-$C_8$)alkyl($C_3$-$C_7$)cycloalkyl group, or a ($C_2$-$C_8$)alkenyl($C_3$-$C_7$)cycloalkyl group, $R^6$ and $R^7$, independently of one another, mean a hydrogen atom, a methyl or ethyl group, or together with the carbon atom of the tetrahydronaphthalene system mean a ($C_3$-$C_6$)-cycloalkyl ring, provided that at least three of radicals $R^1$, $R^2$, $R^{11}$ and $R^{12}$ are not hydrogen, are another subject.

Compounds of general formula (I)

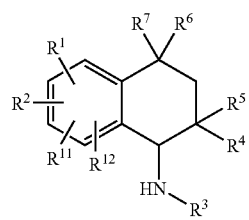

(I)

in which $R^1$ and $R^2$, independently of one another, mean a hydrogen atom, a hydroxy group, a halogen atom, a ($C_1$-$C_{10}$)-alkyl group, a ($C_1$-$C_{10}$)-alkoxy group, a ($C_1$-$C_{10}$)-alkylthio group, a ($C_1$-$C_5$)-perfluoroalkyl group, a cyano group, a nitro group, or $R^1$ and $R^2$ together mean a group that is selected from the groups —O—(CH$_2$)$_n$—O—, —O—(CH$_2$)$_n$—CH$_2$—, —O—CH=CH—, or —(CH$_2$)$_{n+2}$—,
whereby n=1 or 2, and the terminal oxygen atoms and/or carbon atoms are linked to directly adjacent ring-carbon atoms,
or NR$^8$R$^9$,
whereby $R^8$ and $R^9$, independently of one another, can be hydrogen, C$_1$-C$_5$-alkyl or (CO)—C$_1$-C$_5$-alkyl,
$R^{11}$ means a hydrogen atom, a hydroxy group, a halogen atom, a cyano group, an optionally substituted (C$_1$-C$_{10}$)-alkyl group, a (C$_1$-C$_{10}$)-alkoxy group, a (C$_1$-C$_{10}$)-alkylthio group, or a (C$_1$-C$_5$)-perfluoroalkyl group,
$R^{12}$ means a hydrogen atom, a hydroxy group, a halogen atom, a cyano group, an optionally substituted (C$_1$-C$_{10}$)-alkyl group, or a (C$_1$-C$_{10}$)-alkoxy group,
$R^3$ means a C$_1$-C$_{10}$-alkyl group that optionally can be substituted by a group that is selected from 1-3 hydroxy groups, halogen atoms, or 1-3 (C$_1$-C$_5$)-alkoxy groups,
an optionally substituted phenyl group,
a monocyclic or bicyclic heteroaryl group that contains 1-3 nitrogen atoms and/or 1-2 oxygen atoms and/or 1-2 sulfur atoms and that optionally is substituted by 1-2 keto groups, 1-2 (C$_1$-C$_5$)-alkyl groups, 1-2 (C$_1$-C$_5$)-alkoxy groups, 1-3 halogen atoms, or 1-2 exomethylene groups,
whereby these groups can be linked via any position to the amine of the tetrahydronaphthalene system and optionally can be hydrogenated at one or more locations,
$R^4$ means a hydroxy group,
$R^5$ means a (C$_1$-C$_5$)-alkyl group or an optionally partially or completely fluorinated (C$_1$-C$_5$)-alkyl group, an aryl group, a (C$_1$-C$_8$)alkylaryl group, a (C$_2$-C$_8$)alkenylaryl group, a (C$_3$-C$_7$)cycloalkyl group, a (C$_1$-C$_8$)alkyl(C$_3$-C$_7$)cycloalkyl group, or a (C$_2$-C$_8$)alkenyl(C$_3$-C$_7$)cycloalkyl group,
$R^6$ and $R^7$, independently of one another, mean a hydrogen atom, a methyl or ethyl group, or together with the carbon atom of the tetrahydronaphthalene system mean a (C$_3$-C$_6$)-cycloalkyl ring,
provided that at least three of radicals $R^1$, $R^2$, $R^{11}$ and $R^{12}$ are not hydrogen,
are another subject of the invention.
Compounds of general formula (I) according to claim 4,

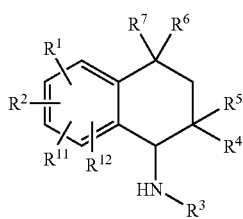

(I)

in which
$R^1$ and $R^2$, independently of one another, mean a hydrogen atom, a hydroxy group, a halogen atom, a (C$_1$-C$_{10}$)-alkyl group, a (C$_1$-C$_{10}$)-alkoxy group, a (C$_1$-C$_{10}$)-alkylthio group, a (C$_1$-C$_5$)-perfluoroalkyl group, a cyano group, or a nitro group, or $R^1$ and $R^2$ together mean a group that is selected from the groups —O—(CH$_2$)$_n$—O—, —O—(CH$_2$)$_n$—CH$_2$—, —O—CH=CH—, or —(CH$_2$)$_{n+2}$—,
whereby n=1 or 2, and the terminal oxygen atoms and/or carbon atoms are linked to directly adjacent ring-carbon atoms,
or NR$^8$R$^9$,
whereby $R^8$ and $R^9$, independently of one another, can be hydrogen, C$_1$-C$_5$-alkyl or (CO)—C$_1$-C$_5$-alkyl,
$R^3$ means a C$_1$-C$_{10}$-alkyl group, which optionally can be substituted by a group that is selected from 1-3 hydroxy groups, halogen atoms, or 1-3 (C$_1$-C$_5$)-alkoxy groups,
an optionally substituted phenyl group or a naphthyl group,
a monocyclic or bicyclic heteroaryl group that contains 1-3 nitrogen atoms and/or 1-2 oxygen atoms and/or 1-2 sulfur atoms and that optionally is substituted by 1-2 keto groups, 1-2 (C$_1$-C$_5$)-alkyl groups, 1-2 (C$_1$-C$_5$)-alkoxy groups, 1-3 halogen atoms, or 1-2 exomethylene groups,
whereby these groups can be linked via any position to the amine of the tetrahydronaphthalene system and optionally can be hydrogenated at one or more locations,
$R^4$ means a hydroxy group,
$R^5$ means a (C$_1$-C$_5$)-alkyl group or an optionally partially or completely fluorinated (C$_1$-C$_5$)-alkyl group, an aryl group, a (C$_1$-C$_8$)alkylaryl group, a (C$_2$-C$_8$)alkenylaryl group, a (C$_3$-C$_7$)cycloalkyl group, a (C$_1$-C$_8$)alkyl(C$_3$-C$_7$)cycloalkyl group, or a (C$_2$-C$_8$)alkenyl(C$_3$-C$_7$)cycloalkyl group,
$R^6$ and $R^7$, independently of one another, mean a hydrogen atom, a methyl or ethyl group, or together with the carbon atom of the tetrahydronaphthalene system mean a (C$_3$-C$_6$)-cycloalkyl ring,
provided that at least three of radicals $R^1$, $R^2$, $R^{11}$ and $R^{12}$ are not hydrogen,
are another subject of the invention.
Compounds of general formula (I) according to claim 4,

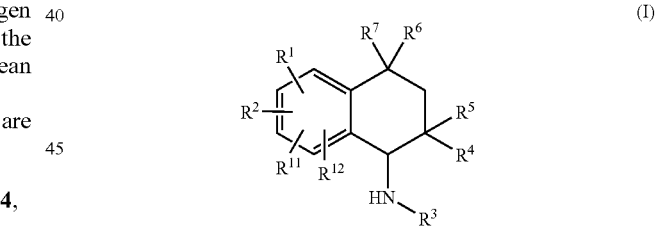

(I)

in which
$R^1$ and $R^2$, independently of one another, mean a hydrogen atom, a hydroxy group, a halogen atom, a (C$_1$-C$_{10}$)-alkyl group, a (C$_1$-C$_{10}$)-alkoxy group, a (C$_1$-C$_{10}$)-alkylthio group, a (C$_1$-C$_5$)-perfluoroalkyl group, a cyano group, a nitro group, or $R^1$ and $R^2$ together mean a group that is selected from the groups —O—(CH$_2$)$_n$—O—, —O—(CH$_2$)$_n$—CH$_2$—, —O—CH=CH—, or —(CH$_2$)$_{n+2}$—,
whereby n=1 or 2, and the terminal oxygen atoms and/or carbon atoms are linked to directly adjacent ring-carbon atoms,
or NR$^8$R$^9$,
whereby $R^8$ and $R^9$, independently of one another, can be hydrogen, C$_1$-C$_5$-alkyl or (CO)—C$_1$-C$_5$-alkyl,
$R^3$ means a C$_1$-C$_{10}$-alkyl group, which optionally can be substituted by a group that is selected from 1-3 hydroxy groups, halogen atoms, or 1-3 (C$_1$-C$_5$)-alkoxy groups,
an optionally substituted phenyl group, a monocyclic or bicyclic heteroaryl group that contains 1-3 nitrogen atoms and/or 1-2 oxygen atoms and/or 1-2 sulfur atoms and that optionally is substituted by 1-2 keto groups, 1-2 ($C_1$-$C_5$)-alkyl groups, 1-2 ($C_1$-$C_5$)-alkoxy groups, 1-3 halogen atoms or 1-2 exomethylene groups, whereby these groups can be linked via any position to the amine of the tetrahydronaphthalene system and optionally can be hydrogenated at one or more locations, $R^4$ means a hydroxy group, $R^5$ means a ($C_1$-$C_5$)-alkyl group or an optionally partially or completely fluorinated ($C_1$-$C_5$)-alkyl group, an aryl group, a ($C_1$-$C_8$)alkylaryl group, a ($C_2$-$C_8$)alkenylaryl group, a ($C_3$-$C_7$)cycloalkyl group, a ($C_1$-$C_8$)alkyl($C_3$-$C_7$)cycloalkyl group, or a ($C_2$-$C_8$)alkenyl($C_3$-$C_7$)cycloalkyl group, $R^6$ and $R^7$, independently of one another, mean a hydrogen atom, a methyl or ethyl group, or together with the carbon atom of the tetrahydronaphthalene system, mean a ($C_3$-$C_6$)-cycloalkyl ring, provided that at least three of radicals $R^1$, $R^2$, $R^{11}$ and $R^{12}$ are not hydrogen, are another subject of the invention.

Compounds of general formula (I)

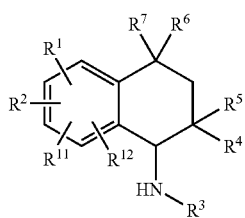

(I)

in which $R^1$ and $R^2$, independently of one another, mean a hydrogen atom, a hydroxy group, a halogen atom, a ($C_1$-$C_5$)-alkyl group, a ($C_1$-$C_5$)-alkoxy group, a ($C_1$-$C_5$)-perfluoroalkyl group, a cyano group, or $R^1$ and $R^2$ together mean a group that is selected from the groups —O—$(CH_2)_n$—O—, —O—$(CH_2)_n$—$CH_2$—, —O—CH=CH—, or —$(CH_2)_{n+2}$—, whereby n=1 or 2, and the terminal oxygen atoms and/or carbon atoms are linked to directly adjacent ring-carbon atoms, $R^{11}$ means a hydrogen atom, a hydroxy group, a halogen atom, a cyano group, an optionally substituted ($C_1$-$C_{10}$)-alkyl group, a ($C_1$-$C_{10}$)-alkoxy group, a ($C_1$-$C_{10}$)-alkylthio group, or a ($C_1$-$C_5$)-perfluoroalkyl group, $R^{12}$ means a hydrogen atom, a hydroxy group, a halogen atom, a cyano group, an optionally substituted ($C_1$-$C_{10}$)-alkyl group, or a ($C_1$-$C_{10}$)-alkoxy group, $R^3$ means a $C_1$-$C_{10}$-alkyl group, which optionally can be substituted by 1-3 hydroxy groups, halogen atoms, a phenyl, phthalidyl, isoindolyl, dihydroindolyl, dihydroisoindolyl, dihydroisoquinolinyl, thiophthalidyl, benzoxazinonyl, phthalazinonyl, quinolinyl, isoquinolinyl, quinolonyl, isoquinolonyl, indazolyl, benzothiazolyl, quinazolinyl, quinoxalinyl, cinnolinyl, phthalazinyl, 1,7- or 1,8-naphthyridinyl, dihydroindolonyl, dihydroisoindolonyl, benzimidazolyl or indolyl group that optionally is substituted with $C_1$-$C_5$-alkyl, halogen, hydroxy, or $C_1$-$C_5$-alkoxy, whereby these groups can be linked via any position to the amine of the tetrahydronaphthalene system and optionally can be substituted in one or more places with 1-2 keto groups, 1-2 ($C_1$-$C_3$)-alkyl groups, 1-2 ($C_1$-$C_3$)-alkoxy groups, 1-3 halogen atoms, or 1-2 exomethylene groups, and optionally can be hydrogenated at one or more locations, $R^4$ means a hydroxy group, $R^5$ means a ($C_1$-$C_5$)-alkyl group or an optionally partially or completely fluorinated ($C_1$-$C_5$)-alkyl group, $R^6$ and $R^7$, independently of one another, mean a hydrogen atom, a methyl or ethyl group or together with the carbon atom of the tetrahydronaphthalene system mean a ($C_3$-$C_6$)-cycloalkyl ring, provided that at least three of radicals $R^1$, $R^2$, $R^{11}$ and $R^{12}$ are not hydrogen, are another subject of the invention.

Compounds of general formula (I)

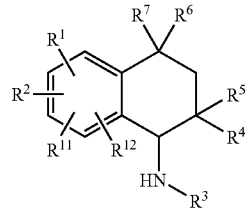

(I)

in which $R^1$ and $R^2$, independently of one another, mean a hydrogen atom, a hydroxy group, a halogen atom, a ($C_1$-$C_5$)-alkyl group, a ($C_1$-$C_5$)-perfluoroalkyl group, a cyano group, a ($C_1$-$C_5$)-alkoxy group, or together mean a ($C_1$-$C_2$)-alkylenedioxy group, whereby then $R^1$ and $R^2$ must be directly adjacent, $R^{11}$ means a hydrogen atom, a hydroxy group, a halogen atom, a cyano group, an optionally substituted ($C_1$-$C_{10}$)-alkyl group, a ($C_1$-$C_{10}$)-alkoxy group, a ($C_1$-$C_{10}$)-alkylthio group, or a ($C_1$-$C_5$)-perfluoroalkyl group, $R^{12}$ means a hydrogen atom, a hydroxy group, a halogen atom, a cyano group, an optionally substituted ($C_1$-$C_{10}$)-alkyl group, or a ($C_1$-$C_{10}$)-alkoxy group, $R^3$ means a phenyl, phthalidyl, isoindolyl, dihydroindolyl, dihydroisoindolyl, dihydroisoquinolinyl, thiophthalidyl, benzoxazinonyl, phthalazinonyl, quinolinyl, isoquinolinyl, quinolonyl, isoquinolonyl, indazolyl, benzothiazolyl, quinazolinyl, quinoxalinyl, cinnolinyl, phthalazinyl, 1,7- or 1,8-naphthyridinyl, dihydroindolonyl, dihydroisoindolonyl, benzimidazolyl or indolyl group that optionally is substituted with $C_1$-$C_5$-alkyl, halogen, hydroxy, or $C_1$-$C_5$-alkoxy, whereby these groups can be linked via any position to the amine of the tetrahydronaphthalene system and optionally can be substituted in one or more places with 1-2 keto groups, 1-2 ($C_1$-$C_3$)-alkyl groups, or 1-2 exomethylene groups, and optionally can be hydrogenated at one or more locations, $R^4$ means a hydroxy group, $R^5$ means a ($C_1$-$C_5$)-alkyl group or an optionally partially or completely fluorinated ($C_1$-$C_5$)-alkyl group, $R^6$ and $R^7$, independently of one another, mean a hydrogen atom, a methyl or ethyl group or together with the carbon atom of the tetrahydronaphthalene system mean a ($C_3$-$C_6$)-cycloalkyl ring, provided that at least three of radicals $R^1$, $R^2$, $R^{11}$ and $R^{12}$ are not hydrogen,
are another subject of the invention.

Compounds of general formula (I) according to claim 4,

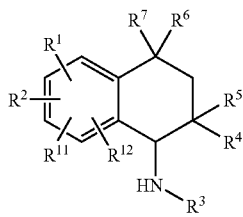

(I)

in which
$R^1$ and $R^2$, independently of one another, mean a hydrogen atom, a hydroxy group, a halogen atom, a ($C_1$-$C_5$)-alkyl group, a ($C_1$-$C_5$)-alkoxy group, a ($C_1$-$C_5$)-perfluoroalkyl group, a cyano group, or $R^1$ and $R^2$ together mean a group that is selected from the groups —O—$(CH_2)_n$—O—, —O—$(CH_2)_n$—$CH_2$—, —O—CH=CH—, or —$(CH_2)_{n+2}$—,
whereby n=1 or 2, and the terminal oxygen atoms and/or carbon atoms are linked to directly adjacent ring-carbon atoms,
$R^3$ means a $C_1$-$C_{10}$-alkyl group, which optionally can be substituted by 1-3 hydroxy groups, halogen atoms; a phenyl, phthalidyl, isoindolyl, dihydroindolyl, dihydroisoindolyl, dihydroisoquinolinyl, thiophthalidyl, benzoxazinonyl, phthalazinonyl, quinolinyl, isoquinolinyl, quinolonyl, isoquinolonyl, indazolyl, benzothiazolyl, quinazolinyl, quinoxalinyl, cinnolinyl, phthalazinyl, 1,7- or 1,8-naphthyridinyl, dihydroindolonyl, dihydroisoindolonyl, benzimidazolyl or indolyl group that optionally is substituted with $C_1$-$C_5$alkyl, halogen, hydroxy, or $C_1$-$C_5$-alkoxy,
whereby these groups can be linked via any position to the amine of the tetrahydronaphthalene system and optionally can be substituted in one or more places with 1-2 keto groups, 1-2 ($C_1$-$C_3$)-alkyl groups, 1-2 ($C_1$-$C_3$)-alkoxy groups, 1-3 halogen atoms, or 1-2 exomethylene groups, and optionally can be hydrogenated at one or more locations,
$R^4$ means a hydroxy group,
$R^5$ means a ($C_1$-$C_5$)-alkyl group or an optionally partially or completely fluorinated ($C_1$-$C_5$)-alkyl group,
$R^6$ and $R^7$, independently of one another, mean a hydrogen atom, a methyl or ethyl group or together with the carbon atom of the tetrahydronaphthalene system mean a ($C_3$-$C_6$)-cycloalkyl ring,
provided that at least three of radicals $R^1$, $R^2$, $R^{11}$ and $R^{12}$ are not hydrogen,
are another subject of the invention.

Compounds of general formula (I) according to claim 4,

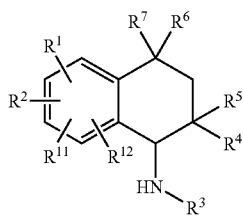

(I)

in which
$R^1$ and $R^2$, independently of one another, mean a hydrogen atom, a hydroxy group, a halogen atom, a ($C_1$-$C_5$)-alkyl group, a ($C_1$-$C_5$)-perfluoroalkyl group, a cyano group, a ($C_1$-$C_5$)-alkoxy group, or together mean a ($C_1$-$C_2$)-alkylenedioxy group, whereby then $R^1$ and $R^2$ must be directly adjacent,
$R^3$ means a phenyl, phthalidyl, isoindolyl, dihydroindolyl, dihydroisoindolyl, dihydroisoquinolinyl, thiophthalidyl, benzoxazinonyl, phthalazinonyl, quinolinyl, isoquinolinyl, quinolonyl, isoquinolonyl, indazolyl, benzothiazolyl, quinazolinyl, quinoxalinyl, cinnolinyl, phthalazinyl, 1,7- or 1,8-naphthyridinyl, dihydroindolonyl, dihydroisoindolonyl, benzimidazolyl or indolyl group that optionally is substituted with $C_1$-$C_5$-alkyl, halogen, hydroxy, or $C_1$-$C_5$-alkoxy,
whereby these groups can be linked via any position to the amine of the tetrahydronaphthalene system and optionally can be substituted in one or more places with 1-2 keto groups, 1-2 ($C_1$-$C_3$)-alkyl groups, or 1-2 exomethylene groups, and optionally can be hydrogenated at one or more locations,
$R^4$ means a hydroxy group,
$R^5$ means a ($C_1$-$C_5$)-alkyl group or an optionally partially or completely fluorinated ($C_1$-$C_5$)-alkyl group,
$R^6$ and $R^7$, independently of one another, mean a hydrogen atom, a methyl or ethyl group or together with the carbon atom of the tetrahydronaphthalene system mean a ($C_3$-$C_5$)-cycloalkyl ring,
provided that at least three of radicals $R^1$, $R^2$, $R^{11}$ and $R^{12}$ are not hydrogen,
are another subject of the invention.

Stereoisomers according to claims 1 to 9 that on the aromatic ring of the tetrahydronaphthalene system carry substituents, selected from the group $C_1$-$C_5$-alkyl, $C_1$-$C_5$-alkoxy, $COOR^{13}$, $NR^8R^9$, C1-$C_5$-perfluoroalkyl, halogen, hydroxy, cyano, nitro, —O—$(CH_2)_n$—O—, —O—$(CH_2)_n$—$CH_2$—, —O—CH=CH—, —$(CH_2)_{n+2}$—, —NH—$(CH_2)_{n+1}$, N($C_1$-$C_3$-alkyl)-$(CH_2)_{n+1}$, or —NH—N=CH—,
whereby n=1 or 2, and the terminal oxygen atoms and/or carbon atoms and/or nitrogen atoms are linked to directly adjacent ring-carbon atoms, are a special subject of the invention. Then, the divalent radicals can be counted as two substituents in terms of the invention.

Compounds according to claims 1 to 9 that on the aromatic ring of the tetrahydronaphthalene system carry three substituents, selected from the group $C_1$-$C_5$-alkyl, $C_1$-$C_5$-alkoxy, $C_1$-$C_5$-perfluoroalkyl, halogen, hydroxy, cyano, nitro, —O—$(CH_2)_n$—O—, —O—$(CH_2)_n$—$CH_2$—, —O—CH=CH—, —$(CH_2)_{n+2}$—, —NH—$(CH_2)_{n+1}$—, —N($C_1$-$C_3$-alkyl)-$(CH_2)_{n+1}$—, or —NH—N=CH—,
whereby n=1 or 2, and the terminal oxygen atoms and/or carbon atoms and/or nitrogen atoms are linked to directly adjacent ring-carbon atoms, are a special subject of the invention. Then, the divalent radicals can be counted as two substituents in terms of the invention.

Another subject of the invention is if $R^3$ is formed by a radical that contains $COOR^{13}$ as a substituent, whereby $R^{13}$ means $C_1$-$C_{10}$-alkyl or $C_1$-$C_5$-alkyl.

The compounds according to claim 1, in which $R^1$ and $R^2$ together mean the radicals —O—$(CH_2)_n$—O—, —O—$(CH_2)_n$—$CH_2$—, —O—CH=CH—, —$(CH_2)_{n+2}$—, —NH—$(CH_2)_{n+1}$—, N($C_1$-$C_3$-alkyl)-$(CH_2)_{n+1}$—, and —NH—N=CH—, are a subgroup of these compounds. The respective terminal atoms of the above-indicated divalent groups are linked to directly adjacent carbon atoms of the tetrahydronaphthalene system.

The stereoisomers according to claims 1 to 9, in which $R^1$, $R^2$, $R^{11}$ or $R^{12}$ are selected from the group that consist of optionally substituted $C_1$-$C_5$-alkyl, optionally substituted $C_1$-$C_5$-alkoxy, halogen, hydroxy, or cyano, are another subgroup.

The compounds according to claim 4, in which $R^1$, $R^2$, $R^{11}$ or $R^{12}$ are selected from the group that consists of $C_1$-$C_5$-alkyl, $C_1$-$C_5$alkoxy, $C_1$-$C_5$-perfluoroalkyl, halogen, hydroxy, cyano, or nitro, are a subgroup.

The compounds according to claim 1, in which alkyl radicals $R^1$ and $R^2$ have the meaning —$(CH_2)_{n+2}$— and thus form a 5- to 6-membered ring together with the carbon atom of the chain, represent another subgroup.

Compounds of general formula I according to claim 1, in which $R^3$ means a $C_1$-$C_{10}$-alkyl group, which optionally can be substituted by 1-3 hydroxy groups, halogen atoms, 1-3 ($C_1$-$C_5$)-alkoxy groups, an optionally substituted ($C_3$-$C_7$)-cycloalkyl group, an optionally substituted heterocyclyl group, a monocyclic or bicyclic heteroaryl group that optionally contains 1-3 nitrogen atoms and/or 1-2 oxygen atoms and/or 1-2 sulfur atoms and/or 1-2 keto groups and that optionally is substituted by one or more groups that are selected from ($C_1$-$C_5$)-alkyl groups, ($C_1$-$C_5$)-alkoxy groups, halogen atoms, or exomethylene groups, whereby these groups can be linked via any position to the amine of the tetrahydronaphthalene system and optionally can be hydrogenated at one or more locations, are another subject of the invention.

Compounds of formula I, in which $R^3$ means a $C_1$-$C_{10}$-alkyl group, which optionally can be substituted by 1-3 hydroxy groups, halogen atoms, an optionally substituted phenyl group, a monocyclic or bicyclic heteroaryl group that contains 1-3 nitrogen atoms and/or 1-2 oxygen atoms and/or 1-2 sulfur atoms and that optionally is substituted by 1-2 keto groups, 1-2 ($C_1$-$C_5$)-alkyl groups, 1-2 ($C_1$-$C_5$)-alkoxy groups, 1-3 halogen atoms, or 1-2 exomethylene groups, whereby these groups can be linked via any position to the nitrogen atom and optionally can be hydrogenated at one or more locations, are another subject of the invention.

Stereoisomers of general formula I, in which $R^3$ means a phenyl group or a naphthyl group that optionally is substituted with one or more radicals from the group $C_1$-$C_5$-alkyl, $C_1$-$C_5$-alkoxy, hydroxy, halogen, cyano, $CF_3$, nitro, $COOR^{13}$, or $NR^8R^9$, are a subject of the invention.

Compounds of general formula I according to claims 1-9, in which $R^3$ means a monocyclic or bicyclic heteroaryl group that optionally contains 1-4 nitrogen atoms and/or 1-2 oxygen atoms and/or 1-2 sulfur atoms and/or 1-2 keto groups and that optionally is substituted by one or more groups, independently of one another, selected from ($C_1$-$C_5$)-alkyl groups, which themselves optionally can be substituted by 1-3 hydroxy groups or 1-3 $COOR^{13}$ groups, whereby $R^{13}$ means hydrogen or ($C_1$-$C_5$)-alkyl; ($C_1$-$C_5$)-alkoxy groups, halogen atoms, hydroxy groups, $NR^8R^9$ groups, exomethylene groups, or oxygen, whereby this group can be linked via any position to the amine of the tetrahydronaphthalene system and optionally can be hydrogenated at one or more locations, are a preferred subject of this invention.

Compounds of general formula I or II according to claims 1-6, in which $R^3$ means a monocyclic or bicyclic heteroaryl group that optionally contains 1-4 nitrogen atoms and/or 1-2 oxygen atoms and/or 1-2 sulfur atoms and/or 1-2 keto groups and that optionally is substituted by one or more groups, independently of one another, selected from ($C_1$-$C_5$)-alkyl groups, which themselves optionally can be substituted by 1-3 hydroxy groups or 1-3 $COOR^{13}$ groups, whereby $R^{13}$ means hydrogen or ($C_1$-$C_5$)-alkyl; ($C_1$-$C_5$)-alkoxy groups, halogen atoms, hydroxy groups, $NR^8R^9$ groups, exomethylene groups, or oxygen, whereby this group can be linked via any position to the amine of the tetrahydronaphthalene system and optionally can be hydrogenated at one or more locations, and $R^5$ means an optionally partially or completely fluorinated ($C_1$-$C_5$)-alkyl group, are another preferred subject of this invention.

Compounds of general formula I, in which $R^3$ means a $C_1$-$C_{10}$-alkyl group, which optionally can be substituted by 1-3 hydroxy groups, halogen atoms, a phenyl, naphthyl, phthalidyl, isoindolyl, dihydroindolyl, dihydroisoindolyl, dihydroisoquinolinyl, dihydroquinolinyl, thiophthalidyl, benzoxazinonyl, phthalazinonyl, quinolinyl, isoquinolinyl, quinolonyl, isoquinolonyl, indazolyl, benzothiazolyl, quinazolinyl, quinoxalinyl, cinnolinyl, phthalazinyl, 1,7- or 1,8-naphthyridinyl, dihydroindolonyl, dihydroisoindolonyl, benzimidazolyl or indolyl group that optionally is substituted with $C_1$-$C_5$-alkyl, halogen, hydroxy, or $C_1$-$C_5$-alkoxy, are a preferred subject of the invention.

Compounds of general formula I, in which $R^3$ a phenyl or naphthyl that optionally is substituted with $C_1$-$C_5$-alkyl, halogen, hydroxy or $C_1$-$C_5$-alkoxy; phthalidyl, thiophthalidyl, benzoxazinonyl, phthalazinonyl, quinolinyl, isoquinolinyl, quinolonyl, isoquinolonyl, indazolyl, benzothiazolyl, quinazolinyl, quinoxalinyl, cinnolinyl, phthalazinyl, 1,7- or 1,8-naphthyridinyl, dihydroindolonyl, dihydroisoindolonyl, benzimidazolyl or indolyl group, are an also preferred subject.

Compounds of general formula I, in which $R^3$ a phenyl, phthalidyl, thiophthalidyl, benzoxazinonyl, phthalazinonyl, quinolinyl, isoquinolinyl, quinolonyl, isoquinolonyl, indazolyl, benzothiazolyl, quinazolinyl, quinoxalinyl, cinnolinyl, phthalazinyl, 1,7- or 1,8-naphthyridinyl, dihydroindolonyl, dihydroisoindolonyl, benzimidazolyl or indolyl group that optionally is substituted with $C_1$-$C_5$-alkyl, halogen, hydroxy or $C_1$-$C_5$-alkoxy are an especially preferred subject.

Compounds of formula (I), in which $R^3$ means phthalidyl, isoindolyl, dihydroindolyl, dihydroisoindolyl, thiophthalidyl, indazolyl, benzothiazolyl, dihydroindolonyl, dihydroisoindolonyl, benzimidazolyl or indolyl group, are another subject of the invention.

Compounds of formula (I), in which $R^3$ means dihydroisoquinolinyl, dihydroquinolinyl, benzoxazinonyl, phthalazinonyl, quinolinyl, isoquinolinyl, quinolonyl, isoquinolonyl, quinazolinyl, quinoxalinyl, cinnolinyl, phthalazinyl, 1,7- or 1,8-naphthyridinyl, are another subject of the invention.

Compounds of general formula I, in which $R^3$ means an isoquinolonyl, quinolonyl, quinazolinyl or phthalazinyl group, are another subject of the invention.

Stereoisomers of general formula I, in which $R^3$ means an optionally substituted isoquinolonyl, quinolonyl, quinazolinyl, phthalazinyl, indazolyl, quinolinyl, isoquinolinyl, isoquinolonyl, dihydroindolonyl, dihydroindolyl, dihydroindolonyl, naphthyl, pyridyl, or phthalidyl group, especially preferably if $R^3$ means an optionally substituted isoquinolonyl, quinolonyl, quinolinyl, quinazolinyl, phthalazinyl, phthalazinonyl, dihydrophthalazinyl, dihydrophthalazinonyl, dihydroindolonyl, dihydroquinolinyl, or dihydroquinolonyl, are a special subject of the invention.

The meanings of $R^3$ that are mentioned in the paragraph above combined with the usual radicals, as they are defined in claims 1-9, are a special subject of the invention.

Compounds of general formula I in which $R^3$ means isoquinolin-1(2H)on-5yl, quinolin-2(1H)-on-5-yl-, 8- or 7-fluoro-2-methyl-quinazoline, 7,8-difluoro-4-methyl-quinazoline, 7,8-difluoro-2-methyl-quinazoline or 2-methyl-phthalazin-1-one are another subject of the invention.

Radical $R^3$ is bonded via the amine to the tetrahydronaphthalene system. If radical $R^3$ exhibits several positions that are chemically possible to be bonded to the ring system, then this invention comprises all these possibilities.

Radical $R^3$ is also part of this invention when it is hydrogenated at one or more locations.

As substituents of the monocyclic or bicyclic heteroaryl groups (heterocyclic groups) $R^3$, just as it was first defined, for example, hydroxy, halogen atoms, in particular fluorine and chlorine, $(C_1-C_5)$-alkyl groups (which themselves optionally can be substituted by hydroxy groups, $(C_1-C_5)$-alkoxy groups or $COOR^{13}$ groups, whereby $R^{13}$ means hydrogen or $(C_1-C_5)$-alkyl), in particular methyl, $(C_2-C_5)$-alkenyl groups, completely or partially fluorinated $(C_1-C_5)$-alkyl groups, in particular $CF_3$, $CFH_2$ or $C_2F_5$, $(C_1-C_5)$-alkoxy groups, in particular methoxy and ethoxy, $NR^8R^9$ groups, in particular $NH_2$, $N(CH_3)_2$ or $NH(CH_3)$, cyano groups as well as keto groups, which are formed with a carbon atom of a ring of the heteroaryl group, and oxygen, which forms an N-oxide with an optionally present nitrogen atom of the ring, are suitable at chemically suitable positions. The group that consists of fluorine, chlorine, OH, $CH_3$, $CF_3$, $CFH_2$, or $C_2F_5$, $OCH_3$, $OC_2H_5$, $NH_2$, $N(CH_3)_2$ and $NH(CH_3)$, cyano, keto and oxygen follows from the above as a preferred group of substituents for radical $R^3$ as it is defined in claim 1 and for all additional claims. Especially preferred are halogen, in particular fluorine and chlorine, hydroxy, $C_1$-$C_5$-alkyl, in particular $CH_3$, $C_2H_5$ or keto-oxygen.

As a subgroup of the substituents of the heterocyclic group $R^3$, as it was first defined in the above-mentioned subjects of the invention, for example, halogen atoms, $(C_1-C_5)$-alkyl groups (which themselves are substituted by hydroxy groups or COOH groups or $COOR^{13}$ groups, whereby $R^{13}$ means hydrogen or $(C_1-C_5)$-alkyl), $(C_2-C_5)$-alkenyl groups, fluorinated $(C_1-C_5)$-alkyl groups, $(C_1-C_5)$-alkoxy groups or cyano groups are suitable at suitable positions.

Heterocyclyl group $R^3$ is not aromatic and can be, for example, pyrrolidine, imidazolidine, pyrazolidine, or piperidine.

The hydroxy group in $R^4$ can be protected by one of the common hydroxy protective groups that are known to one skilled in the art, such as, for example, silyl ether or ester of organic $C_1$-$C_{10}$ acids or can be present as $C_1$-$C_5$-ether or benzyl ether, preferably as one of the common hydroxy protective groups or as $C_1$-$C_5$-ether. The hydroxy group is preferred as radical $R^4$.

The common hydroxy protective groups are described in detail in T. W. Greene, P. G. M. Wuts "Protective Groups in Organic Synthesis," $2^{nd}$ Edition, John Wiley & Sons, 1991).

The protective groups are preferably alkyl, aryl- or mixed alkylaryl-substituted silyl groups, e.g., the trimethylsilyl (TMS), triethylsilyl (TES), tert-butyldimethylsilyl (TBDMS), tert-butyldiphenylsilyl (TBDPS) or triisopropylsilyl groups (TIPS) or another conventional hydroxy protective group (methoxymethyl, methoxyethoxymethyl, ethoxyethyl, tetrahydrofuranyl, and tetrahydropyranyl groups).

Radical $R^5$ is bonded directly to the tetrahydronaphthalene system. If radical $R^5$ has several positions that are chemically possible to be bonded to the ring system, this invention then encompasses all these possibilities.

Stereoisomers of general formula I according to claim 1, in which $R^5$ means a $(C_3-C_7)$cycloalkyl group, a $(C_1-C_8)$alkyl$(C_3-C_7)$cycloalkyl group, a $(C_2-C_8)$alkenyl$(C_3-C_7)$cycloalkyl group, a heterocyclyl group, a $(C_1-C_8)$alkylheterocyclyl group, a $(C_2-C_8)$alkenylheterocyclyl group, an aryl group, a $(C_1-C_8)$alkylaryl group, a $(C_2-C_8)$alkenylaryl group, a monocyclic or bicyclic heteroaryl group that contains 1-3 nitrogen atoms and/or 1-2 oxygen atoms and/or 1-2 sulfur atoms and that optionally is substituted by 1-2 keto groups, 1-2 $(C_1-C_5)$-alkyl groups, 1-2 $(C_1-C_5)$-alkoxy groups, 1-3 halogen atoms, 1-2 exomethylene groups; a $(C_1-C_8)$alkylheteroaryl group or a $(C_2-C_8)$alkenylheteroaryl group, or a $(C_2-C_8)$alkinylheteroaryl group, whereby these groups can be linked via any position to the tetrahydronaphthalene system and optionally can be hydrogenated at one or more locations, are another subgroup of the invention.

Compounds of general formula I in which $R^5$ means a $(C_1-C_5)$-alkyl group or an optionally partially or completely fluorinated $(C_1-C_5)$-alkyl group, a $(C_3-C_7)$cycloalkyl group, a $(C_1-C_8)$alkyl$(C_3-C_7)$cycloalkyl group, a $(C_2-C_8)$alkenyl$(C_3-C_7)$cycloalkyl group, a heterocyclyl group, a $(C_1-C_8)$alkylheterocyclyl group, a $(C_2-C_8)$alkenylheterocyclyl group, an aryl group, a $(C_1-C_8)$alkylaryl group, or a $(C_2-C_8)$alkenylaryl group are another subject of the invention.

Compounds of general formula I in which $R^5$ means a $(C_1-C_5)$-alkyl group or an optionally partially or completely fluorinated $(C_1-C_5)$-alkyl group, an aryl group, a $(C_1-C_8)$ alkylaryl group, a $(C_2-C_8)$alkenylaryl group, a $(C_3-C_7)$cycloalkyl group, a $(C_1-C_8)$alkyl$(C_3-C_7)$cycloalkyl group, or a $(C_2-C_8)$alkenyl$(C_3-C_7)$cycloalkyl group are a special subject of the invention.

Stereoisomers of general formula I according to claims 1 to 6, in which $R^5$ represents a $(C_1-C_{10})$-alkyl group or an optionally partially or completely fluorinated $(C_1-C_{10})$-alkyl group, preferably represents a $(C_1-C_5)$-alkyl group or an optionally partially or completely fluorinated $(C_1-C_5)$-alkyl group, especially preferably represents a $(C_1-C_3)$-alkyl group or an optionally partially or completely fluorinated $(C_1-C_3)$-alkyl group, in particular an optionally or partially or completely fluorinated $(C_1-C_3)$-alkyl group, or quite especially represents $CF_3$ or $C_2F_5$, are another subject of the invention.

Preferred are stereoisomers according to claims 1 to 9 whose radical $R^5$ means an optionally partially or completely fluorinated $(C_1-C_5)$-alkyl group, in particular an optionally partially or completely fluorinated $(C_1-C_3)$-alkyl group.

The radicals and all their subcombinations, which are confirmed by the examples, represent an especially preferred subgroup, as it was disclosed for this invention.

The designation halogen atom or halogen means a fluorine, chlorine, bromine or iodine atom. A fluorine, chlorine or bromine atom is preferred.

The $C_1$-$C_{10}$- or $C_1$-$C_5$-alkyl groups $R^1$, $R^2$, $R^4$, $R^5$, $R^6$, $R^7$, $R^{11}$ and $R^{12}$ can be straight-chain or branched and stand for, for example, a methyl, ethyl, n-propyl, iso-propyl, n-butyl, iso-butyl, tert.-butyl or n-pentyl, 2,2-dimethylpropyl, 2-methylbutyl or 3-methylbutyl group, as well as hexyl, heptyl, nonyl, or decyl group, and any of their branched derivatives. A methyl or ethyl group is preferred.

The above-mentioned alkyl groups optionally can be substituted by 1-5 groups, independently of one another, selected from hydroxy, cyano, nitro, $COOR^{13}$, $C_1$-$C_5$-alkoxy groups, halogen, $NR^8R^9$, a partially or completely fluorinated $C_1$-$C_3$-alkyl group; the substituents 1-3 halogen atoms and/or 1-3 hydroxy groups and/or 1-3 cyano groups and/or 1-3 $COOR^{13}$ groups represent a subgroup. Fluorine atom, hydroxy, methoxy and/or cyano groups represent a preferred subgroup.

They can optionally also only be substituted by 1-3 hydroxy groups and/or 1-3 $COOR^{13}$ groups. Hydroxy groups are preferred.

For a partially or completely fluorinated $C_1$-$C_3$-alkyl group, for example, the following partially or completely fluorinated groups are considered: fluoromethyl, difluoromethyl, trifluoromethyl, fluoroethyl, 1,1-difluoroethyl, 1,2-difluoroethyl, 1,1,1-trifluoroethyl, tetrafluoroethyl, and pentafluoroethyl. Of the latter, the trifluoromethyl group or the pentafluoroethyl group is preferred, and the completely fluorinated group is also named perfluoroalkyl group.

The reagents, which optionally are used during the synthesis, are commercially available, or the published syntheses of the corresponding reagents are part of the prior art, or published syntheses can be used analogously.

The $C_1$-$C_{10}$- or $C_1$-$C_5$-alkoxy groups can be straight-chain or branched and stand for, for example, a methoxy, ethoxy, n-propoxy, iso-propoxy-, n-butoxy, iso-butoxy, tert.-butoxy or n-pentoxy, 2,2-dimethylpropoxy, 2-methylbutoxy or 3-methylbutoxy group. $C_1$-$C_5$-Alkoxy groups are preferred. A methoxy or ethoxy group is especially preferred.

The above-mentioned alkoxy groups optionally can be substituted with 1-3 groups that are selected from halogen, in particular fluorine, chlorine, hydroxy and cyano.

The $C_1$-$C_5$-alkylthio groups can be straight-chain or branched and stand for, for example, a methylthio, ethylthio, n-propylthio, iso-propylthio, n-butylthio, iso-butylthio, tert.-butylthio or n-pentylthio, 2,2-dimethylpropylthio, 2-methylbutylthio or 3-methylbutylthio group. A methylthio or ethylthio group is preferred.

Substituent $NR^8R^9$ means, for example, $NH_2$, $NH(CH_3)$, $N(CH_3)_2$, $NH(C_2H_5)$, $N(C_2H_5)_2$, $NH(C_3H_7)$, $N(C_3H_7)_2$, $NH(C_4H_9)$, $N(C_4H_9)_2$, $NH(C_5H_{11})$, $N(C_5H_{11})_2$, $NH(CO)CH_3$, $NH(CO)C_2H_5$, $NH(CO)C_3H_7$, $NH(CO)C_4H_9$, or $NH(CO)C_5H_{11}$.

The cycloalkyl group means a saturated cyclic group that optionally is substituted by one or more groups selected from hydroxy groups, halogen atoms, ($C_1$-$C_5$)-alkyl groups, ($C_1$-$C_5$)-alkoxy groups, $NR^8R^9$ groups, $COOR^{13}$ groups, CHO, and cyano, and said group has 3 to 7 ring-carbon atoms, such as, for example, cyclopropyl, methylcyclopropyl, cyclobutyl, methylcyclobutyl, cyclopentyl, methylcyclopentyl, cyclohexyl, methylcyclohexyl, cycloheptyl, and methylcycloheptyl.

A ($C_1$-$C_8$)alkyl($C_3$-$C_7$)cycloalkyl group $R^5$ is defined as a cycloalkyl group that is linked to the ring system via a straight-chain or branched ($C_1$-$C_8$)-alkyl unit.

A ($C_2$-$C_8$)alkenyl($C_3$-$C_7$)cycloalkyl group $R^5$ is defined as a cycloalkyl group that is linked to the ring system via a straight-chain or branched ($C_2$-$C_8$)-alkenyl unit.

The heterocyclyl group is not aromatic and can be, for example, pyrrolidine, pyrazolidine, or piperidine. Perhydroquinoline and perhydroisoquinoline are also part of the included heterocyclyl groups. As substituents for heterocyclyl and heteroaryl groups, for example, substituents from the group optionally substituted $C_1$-$C_5$-alkyl group, hydroxy-, $C_1$-$C_5$-alkoxy-, $NR^8R^9$—, halogen, cyano-, $COOR^{13}$—, and CHO— are suitable. The substituents can optionally also be bonded to the nitrogen atom; then N-oxides are also included in the definition.

Aryl groups in terms of the invention are the aromatic carbocyclic groups with 6 to 14 carbon atoms, which exhibit a ring, such as, e.g., phenyl or phenylene, or several condensed rings, such as, e.g., naphthyl or anthranyl. By way of example, phenyl, naphthyl, anthranyl, indanyl, tetralinyl and indenyl can be mentioned.

The aryl groups can be substituted at any suitable position that results in a stable compound by one or more radicals from the group hydroxy, halogen; $C_1$-$C_5$-alkyl that optionally is substituted by 1-3 hydroxy groups or $COOR^{13}$ groups; $C_1$-$C_5$-alkoxy, cyano, $CF_3$, and nitro. The optionally substituted phenyl group and the naphthyl group are preferred.

A ($C_1$-$C_8$)alkylaryl group is an aryl group, as it is already described above, that is linked to the ring system via a straight-chain or branched ($C_1$-$C_8$)-alkyl unit.

A ($C_2$-$C_8$)alkenylaryl group is an aryl group, as it is already described above, that is linked to the ring system via a straight-chain or branched ($C_2$-$C_8$)-alkenyl unit.

A ($C_2$-$C_8$)alkinylaryl group is an aryl group, as it is already described above, that is linked to the ring system via a straight-chain or branched ($C_2$-$C_8$)-alkinyl unit.

The monocyclic or bicyclic heteroaryl group can optionally be substituted by one or more substituents that are selected from $C_1$-$C_5$-alkyl group, $C_1$-$C_5$-alkoxy group, halogen or exomethylene that optionally are substituted by 1-3 hydroxy groups or 1-3 $COOR^{13}$ groups. The substituents optionally also can be directly bonded to the heteroatom. N-oxides are also included in this invention.

The monocyclic or bicyclic heteroaryl group optionally can contain 0-9 groups from the group nitrogen atoms, oxygen atoms, sulfur atoms or keto groups, of which at most 4 nitrogen atoms, at most 2 oxygen atoms, at most 2 sulfur atoms and at most 2 keto groups can be contained. Any subcombination of these groups is possible. The heteroaryl group can be hydrogenated at one or more locations.

Monocyclic heteroaryl groups can be, for example, pyridine, pyrazine, pyrimidine, pyridazine, triazine, azaindolizine, 2H- and 4H-pyran, 2H- and 4H-thiopyran, furan, thiophene, 1H- and 4H-pyrazole, 1H- and 2H-pyrrole, oxazole, thiazole, furazan, 1H- and 4H-imidazole, isoxazole, isothiazole, oxadiazole, triazole, tetrazole, or thiadiazole.

Bicyclic heteroaryl groups can be, for example, a phthalidyl, thiophthalidyl, indolyl, isoindolyl, dihydroindolyl, dihydroisoindolyl, indazolyl, benzothiazolyl, indolonyl, dihydroindolonyl, isoindolonyl, dihydroisoindolonyl, benzofuranyl, benzimidazolyl, dihydroisoquinolinyl, dihydroquinolinyl, benzoxazinonyl, phthalazinonyl, dihydrophthalazinonyl, quinolinyl, isoquinolinyl, quinolonyl, isoquinolonyl, quinazolinyl, quinoxalinyl, cinnolinyl, phthalazinyl, dihydrophthalazinyl, 1,7- or 1,8-naphthyridinyl, cumarinyl, isocumarinyl, indolizinyl, isobenzofuranyl, azaindolyl, azaisoindolyl, furanopyridyl, furanopyrimidinyl, furanopyrazinyl, furanopyridazinyl, dihydrobenzofuranyl, dihydrofuranopyridyl, dihydrofuranopyrimidinyl, dihydrofuranopyrazinyl, dihydrofuranopyridazinyl, or dihydrobenzofuranyl group.

If the heteroaryl groups are partially or completely hydrogenated, stereoisomers of formula I or II, in which $R^3$ means tetrahydropyranyl, 2H-pyranyl, 4H-pyranyl, piperidyl, tetrahydropyridyl, dihydropyridyl, 1H-pyridin-2-onyl, 1H-pyridin-4-onyl, 4-aminopyridyl, 1H-pyridin-4-ylidenaminyl, chromanyl, isochromanyl, thiochromanyl, decahydroquinolinyl, tetrahydroquinolinyl, dihydroquinolinyl, 5,6,7,8-tetrahydro-1H-quinolin-4-onyl, decahydroisoquinolinyl, tetrahydroisoquinolinyl, dihydroisoquinolinyl, 3,4-dihydro-2H-benz[1,4]oxazinyl, 1,2-dihydro[1,3]benzoxazin-4-onyl, 3,4-dihydrobenz[1,4]oxazin-4-only, 3,4-dihydro-2H-benzo[1,4]thiazinyl, 4H-benzo[1,4]thiazinyl, 1,2,3,4-tetrahydroquinoxalinyl, 1H-cinnolin-4-onyl, 3H-quinazolin-4-onyl, 1H-quinazolin-4-onyl, 3,4-dihydro-1H-quinoxalin-2-onyl, 2,3-1,2,3,4-tetrahydro[1,5]naphthyridinyl, dihydro-1H-[1,5]naphthyridyl, 1H-[1,5]naphthyrid-4-onyl, 5,6,7,8-tetrahydro-1H-naphthyridin-4-onyl, 1,2-dihydropyrido[3,2-d][1,3]oxazin-4-onyl, octahydro-1H-indolyl, 2,3-dihydro-1H-indolyl, octahydro-2H-isoindolyl, 1,3-dihydro-2H-isoindolyl, 1,2-dihydroindazolyl, 1H-pyrrolo[2,3-b]pyridyl, 2,3-dihydro-1H-pyrrolo[2,3-b]pyridyl, 2,2-dihydro-1H-pyrrolo[2,3-b]pyridin-3-onyl, are part of this invention.

A ($C_1$-$C_8$)alkylheteroaryl group is a heteroaryl group, as it is already described above, which is linked to the ring system via a straight-chain or branched ($C_1$-$C_8$)-alkyl unit.

A (C$_2$-C$_8$)alkenylheteroaryl group is a heteroaryl group, as it is already described above, which is linked to the ring system via a straight-chain or branched (C$_2$-C$_8$)-alkenyl unit.

A (C$_2$-C$_8$)alkinylheteroaryl group is a heteroaryl group, as it is already described above, which is linked to the ring system via a straight-chain or branched (C$_2$-C$_8$)-alkinyl unit.

A (C$_1$-C$_8$)alkylheterocyclyl group is a heterocyclyl group, as it is already described above, which is linked to the ring system via a straight-chain or branched (C$_1$-C$_8$)-alkyl unit.

A (C$_2$-C$_8$)alkenylheterocyclyl group is a heterocyclyl group, as it is already described above, which is linked to the ring system via a straight-chain or branched (C$_2$-C$_8$)-alkenyl unit.

The compounds of general formula I according to the invention can be present as stereoisomers because of the presence of asymmetry centers. All possible diastereomers (e.g.: RR, RS, SR, SS) both as racemates and in enantiomer-pure form are subjects of this invention. The term stereoisomers also comprises all possible diastereomers and regioisomers and tautomers (e.g., keto-enol tautomers), in which the stereoisomers according to the invention can be present, which thus are also the subject of the invention.

The compounds according to the invention can also be present in the form of salts with physiologically compatible anions, for example in the form of hydrochloride, sulfate, nitrate, phosphate, pivalate, maleate, fumarate, tartrate, benzoate, mesylate, citrate or succinate.

The compounds according to the invention are produced by the open-chain precursors of general formula II, in which radicals R$^1$, R$^{11}$, R$^{12}$, R$^3$, R$^4$, R$^5$, R$^6$ and R$^7$ have the above-indicated meanings,

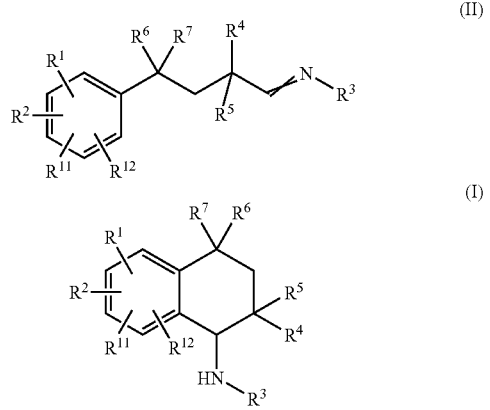

optionally acid or Lewis acid being generated according to methods that are known in the prior art, and then being cyclized to the compounds of general formula I either without additional reagent with a solvent, preferably chlorinated hydrocarbons, such as, e.g., methylene chloride or dichloroethane or concentrated organic acids, preferably glacial acetic acid, or by adding inorganic or organic acids or Lewis acids under temperatures in the range of −70° C. to +80° C. (preferably in the range of −30° C. to +80° C.).

A method for the production of stereoisomers of general formula I, which is characterized in that imines of general formula II are cyclized to the stereoisomers of general formula I either without additional reagent in a solvent or concentrated organic acids, or by adding inorganic or organic acids or Lewis acids under temperatures in the range of −70° C. to +80° C. (preferably in the range of −30° C. to +80° C.) as well as their direct precursors of formula II, is thus also a subject of this invention.

The new imines for the cyclization are also subjects of this invention, in particular the compounds of general formula II, in which R$^1$, R$^{11}$, R$^{12}$, R$^3$, R$^4$, R$^5$, R$^6$ and R$^7$ in each case have the radicals that are defined in claims 1 to 9, quite especially those that have been disclosed by the examples.

The binding of the substances to the glucocorticoid receptor (GR) and other steroid-hormone receptors (mineral corticoid receptor (MR), progesterone receptor (PR) and androgen receptor (AR)) is examined with the aid of recombinantly produced receptors. Cytosol preparations of Sf9 cells, which had been infected with recombinant baculoviruses that code for the GR, are used for the binding studies. In comparison to the reference substance [$^3$H]-dexamethasone, the substances show a high affinity to the GR. IC$_{50}$(GR)=86 nM and IC$_{50}$(PR)=>1000 were thus measured for the compound from Example 3.

The GR-mediated inhibition of the transcription of cytokines, adhesion molecules, enzymes and other pro-inflammatory factors is considered to be an essential, molecular mechanism for the anti-inflammatory action of glucocorticoids. This inhibition is produced by an interaction of the GR with other transcription factors, e.g., AP-1 and NF-kappa-B (for a survey, see Cato, A. C. B. and Wade, E., BioEssays 18, 371-378, 1996).

The compounds of general formula I according to the invention inhibit the secretion of cytokine IL-8 into the human monocyte cell line THP-1 that is triggered by lipopolysaccharide (LPS). The concentration of the cytokines was determined in the supernatant by means of commercially available ELISA kits. The compound of Example 3 showed an inhibition IC$_{50}$(IL8)=40 nm (79% eff).

The anti-inflammatory action of the compounds of general formula I was tested in the animal experiment by tests in the croton oil-induced inflammation in rats and mice (J. Exp. Med. (1995), 182, 99-108). To this end, croton oil in ethanolic solution was applied topically to the animals' ears. The test substances were also applied topically or systemically at the same time or two hours before the croton oil. After 16-24 hours, the ear weight was measured as a yardstick for inflammatory edema, the peroxidase activity as a yardstick for the invasions of granulocytes, and the elastase activity as a yardstick for the invasion of neutrophilic granulocytes. In this test, the compounds of general formula I inhibit the three above-mentioned inflammation parameters both after topical administration and after systemic administration.

One of the most frequent undesirable actions of a glucocorticoid therapy is the so-called "steroid diabetes" [cf. Hatz, H. J., Glucocorticoide: Immunologische Grundlagen, Pharmakologie and Therapierichtlinien, [Glucocorticoids: Immunological Bases, Pharmacology and Therapy Guidelines], Wissenschaftliche Verlagsgesellschaft mbH, Stuttgart, 1998]. The reason for this is the stimulation of gluconeogenesis in the liver by induction of the enzymes responsible in this respect and by free amino acids, which are produced from the degradation of proteins (catabolic action of glucocorticoids). A key enzyme of the catabolic metabolism in the liver is tyrosinamino transferase (TAT). The activity of this enzyme can be determined from liver homogenates by photometry and represents a good measurement of the undesirable metabolic actions of glucocorticoids. To measure the TAT induction, the animals are sacrificed 8 hours after the test substances are administered, the livers are removed, and the TAT activity is measured in the homogenate. In this test, at doses in which they have an anti-inflammatory action, the compounds of general formula I induce little or no tyrosinamino transferase.

Because of their anti-inflammatory action, and, in addition, anti-allergic, immunosuppressive and antiproliferative action, the compounds of general formula I according to the invention can be used as medications for treatment or prophylaxis of the following pathologic conditions in mammals and humans: In this case, the term "DISEASE" stands for the following indications:

(i) Lung diseases that are accompanied by inflammatory, allergic and/or proliferative processes:
    Chronic, obstructive lung diseases of any origin, primarily bronchial asthma
    Bronchitis of different origins
    All forms of restrictive lung diseases, primarily allergic alveolitis,
    All forms of pulmonary edema, primarily toxic pulmonary edema
    Sarcoidoses and granulomatoses, especially Boeck's disease (ii) Rheumatic diseases/autoimmune diseases/joint diseases that are accompanied by inflammatory, allergic and/or proliferative processes:
    All forms of rheumatic diseases, especially rheumatoid arthritis, acute rheumatic fever, polymyalgia rheumatica
    Reactive arthritis
    Inflammatory soft-tissue diseases of other origins
    Arthritic symptoms in the case of degenerative joint diseases (arthroses)
    Traumatic arthritides
    Collagenoses of any origin, e.g., systemic lupus erythematodes, sclerodermia, polymyositis, dermatomyositis, Sjögren's syndrome, Still's syndrome, Felty's syndrome (iii) Allergies that are accompanied by inflammatory and/or proliferative processes:
    All forms of allergic reactions, e.g., Quincke's edema, hay fever, insect bites, allergic reactions to pharmaceutical agents, blood derivatives, contrast media, etc., anaphylactic shock, urticaria, contact dermatitis (iv) Vascular inflammations (vasculitides)
    Panarteritis nodosa, temporal arteritis, erythema nodosum (v) Dermatological diseases that are accompanied by inflammatory, allergic and/or proliferative processes:
    Atopic dermatitis (primarily in children)
    Psoriasis
    Pityriasis rubra pilaris
    Erythematous diseases, triggered by different noxae, e.g., radiation, chemicals, burns, etc.
    Bullous dermatoses
    Diseases of the lichenoid group,
    Pruritis (e.g., of allergic origin)
    Seborrheal eczema
    Rosacea
    Pemphigus vulgaris
    Erythema exudativum multiforme
    Balanitis
    Vulvitis
    Hair loss such as alopecia areata
    Cutaneous T-cell lymphoma (vi) Kidney diseases that are accompanied by inflammatory, allergic and/or proliferative processes:
    Nephrotic syndrome
    All nephritides (vii) Liver diseases that are accompanied by inflammatory, allergic and/or proliferative processes:
    Acute liver cell decomposition
    Acute hepatitis of different origins, e.g., viral, toxic, pharmaceutical agent-induced
    Chronic aggressive hepatitis and/or chronic intermittent hepatitis (viii) Gastrointestinal diseases that are accompanied by inflammatory, allergic and/or proliferative processes:
    Regional enteritis (Crohn's disease)
    Colitis ulcerosa
    Gastritis
    Reflux esophagitis
    Ulcerative colitis of other origins, e.g., native sprue (ix) Proctologic diseases that are accompanied by inflammatory, allergic and/or proliferative processes:
    Anal eczema
    Fissures
    Hemorrhoids
    Idiopathic proctitis (x) Eye diseases that are accompanied by inflammatory, allergic and/or proliferative processes:
    Allergic keratitis, uveitis, iritis
    Conjunctivitis
    Blepharitis
    Optic neuritis
    Chorioiditis
    Sympathetic ophthalmia (xi) Diseases of the ear-nose-throat area that are accompanied by inflammatory, allergic and/or proliferative processes:
    Allergic rhinitis, hay fever
    Otitis externa, e.g., caused by contact dermatitis, infection, etc.
    Otitis media (xii) Neurological diseases that are accompanied by inflammatory, allergic and/or proliferative processes:
    Cerebral edema, primarily tumor-induced cerebral edema
    Multiple sclerosis
    Acute encephalomyelitis
    Meningitis
    Various forms of convulsions, e.g., infantile nodding spasms (xiii) Blood diseases that are accompanied by inflammatory, allergic and/or proliferative processes:
    Acquired hemolytic anemia
    Idiopathic thrombocytopenia (xiv) Tumor diseases that are accompanied by inflammatory, allergic and/or proliferative processes:
    Acute lymphatic leukemia
    Malignant lymphoma
    Lymphogranulomatoses
    Lymphosarcoma
    Extensive metastases, mainly in breast, bronchial and prostate cancers (xv) Endocrine diseases that are accompanied by inflammatory, allergic and/or proliferative processes:
    Endocrine orbitopathy
    Thyreotoxic crisis
    De Quervain's thyroiditis
    Hashimoto's thyroiditis
    Basedow's disease (xvi) Organ and tissue transplants, graft-versus-host disease (xvii) Severe shock conditions, e.g., anaphylactic shock, systemic inflammatory response syndrome (SIRS)

(xviii) Substitution therapy in:
    Innate primary suprarenal insufficiency, e.g., congenital adrenogenital syndrome Acquired primary suprarenal insufficiency, e.g., Addison's disease, autoimmune adrenalitis, meta-infective tumors, metastases, etc.

Innate secondary suprarenal insufficiency, e.g., congenital hypopituitarism

Acquired secondary suprarenal insufficiency, e.g., meta-infective tumors, etc.

(xix) Vomiting that is accompanied by inflammatory, allergic and/or proliferative processes:

e.g., in combination with a 5-HT3 antagonist in cytostatic-agent-induced vomiting (xx) Pains of inflammatory origins, e.g., lumbago.

Moreover, the compounds of general formula I according to the invention can be used for treatment and prophylaxis of additional pathologic conditions that are not mentioned above, for which synthetic glucocorticoids are now used (see in this respect Hatz, H. J., Glucocorticoide: Immunologische Grundlagen, Pharmakologie and Therapierichtlinien, Wissenschaftliche Verlagsgesellschaft mbH, Stuttgart, 1998).

All previously mentioned indications (i) to (xx) are described in more detail in Hatz, H. J., Glucocorticoide: Immunologische Grundlagen, Pharmakologie and Therapierichtlinien, Wissenschaftliche Verlagsgesellschaft mbH, Stuttgart, 1998.

For the therapeutic actions in the above-mentioned pathologic conditions, the suitable dose varies and depends on, for example, the active strength of the compound of general formula I, the host, the type of administration, and the type and severity of the conditions that are to be treated, as well as the use as a prophylactic agent or therapeutic agent.

The invention relates to the use of the claimed compounds for the production of a pharmaceutical agent.

In addition, the invention provides:

(i) The use of one of the compounds of general formula I according to the invention or mixture thereof for the production of a medication for treating a DISEASE;

(ii) A process for treating a DISEASE, said process comprises an administration of an amount of the compound according to the invention, whereby the amount suppresses the disease and whereby the amount of compound is given to a patient who requires such a medication;

(iii) A pharmaceutical composition for treating a DISEASE, said treatment comprises one of the compounds according to the invention or mixture thereof and at least one pharmaceutical adjuvant and/or vehicle.

In general, satisfactory results can be expected in animals when the daily doses comprise a range of 1 µg to 100,000 µg of the compound according to the invention per kg of body weight. In the case of larger mammals, for example the human, a recommended daily dose lies in the range of 1 µg to 100,000 µg per kg of body weight. Preferred is a dose of 10 to 30,000 µg per kg of body weight, and more preferred is a dose of 10 to 10,000 µg per kg of body weight. For example, this dose is suitably administered several times daily. For treating acute shock (e.g., anaphylactic shock), individual doses can be given that are significantly above the above-mentioned doses.

The formulation of the pharmaceutical preparations based on the new compounds is carried out in a way that is known in the art by the active ingredient being processed with the vehicles, fillers, substances that influence decomposition, binding agents, moisturizers, lubricants, absorbents, diluents, flavoring correctives, coloring agents, etc., that are commonly used in galenicals and converted into the desired form of administration. In this case, reference is made to Remington's Pharmaceutical Science, 15$^{th}$ Edition, Mack Publishing Company, East Pennsylvania (1980).

For oral administration, especially tablets, coated tablets, capsules, pills, powders, granulates, lozenges, suspensions, emulsions or solutions are suitable.

For parenteral administration, injection and infusion preparations are possible.

For intra-articular injection, correspondingly prepared crystal suspensions can be used.

For intramuscular injection, aqueous and oily injection solutions or suspensions and corresponding depot preparations can be used.

For rectal administration, the new compounds can be used in the form of suppositories, capsules, solutions (e.g., in the form of enemas) and ointments both for systemic and for local treatment.

For pulmonary administration of the new compounds, the latter can be used in the form of aerosols and inhalants.

For local application to eyes, outer ear channels, middle ears, nasal cavities, and paranasal sinuses, the new compounds can be used as drops, ointments and tinctures in corresponding pharmaceutical preparations.

For topical application, formulations in gels, ointments, fatty ointments, creams, pastes, powders, milk and tinctures are possible. The dosage of the compounds of general formula I should be 0.01%-20% in these preparations to achieve a sufficient pharmacological action.

The invention also comprises the compounds of general formula I according to the invention as therapeutic active ingredients. In addition, the compounds of general formula I according to the invention are part of the invention as therapeutic active ingredients together with pharmaceutically compatible and acceptable adjuvants and vehicles.

The invention also comprises a pharmaceutical composition that contains one of the pharmaceutically active compounds according to the invention or mixtures thereof or a pharmaceutically compatible salt thereof and a pharmaceutically compatible salt or pharmaceutically compatible adjuvants and vehicles.

EXPERIMENTS

Example 1 rac.) 5-{[6-Fluoro-2,5-dihydroxy-4,4,7-trimethyl-2-(trifluoromethyl)-1,2,3,4-tetrahydronaphthalen-1-yl] amino}-isoquinolin-1(2H)-one 5-Amino-isoquinolin-1(2H)-one 2-Methyl-3-nitrobenzoic acid methyl ester 30 g (165.6 mmol) of 2-methyl-3-nitrobenzoic acid is added to 150 ml of methanol, and it is refluxed for two days after 2.9 ml of concentrated sulfuric acid is added. After cooling, the crystallizate (25.55 g=79%) is suctioned off and used in the next stage.

$^1$H-NMR (300 MHz, DMSO-$d_6$): δ=2.50 (3H), 3.85 (3H), 7.56 (1H), 8.00 (1H), 8.05 (1H).

2-(Bromomethyl)-3-nitrobenzoic acid methyl ester 25.55 g (130.9 mmol) of 2-methyl-3-nitrobenzoic acid methyl ester is added to 300 ml of carbon tetrachloride, and mixed with 25.6 g (141.7 mmol) of N-bromosuccinimide and 62.8 mg of benzoyl peroxide. After seven days of refluxing, the succinimide is suctioned off after cooling, and then the filtrate is spun in until a dry state is reached. The desired compound that is incorporated in crude form into the next stage remains.

$^1$H-NMR (300 MHz, CDCl$_3$): δ=4.00 (3H), 5.66 (2H), 7.55 (1H), 7.95 (1H), 8.10 (1H).

5-Nitroisocoumarin 16.4 g (84.03 mmol) of 2-methyl-3-nitrobenzoic acid methyl ester is stirred with 26.8 g (225.1 mmol) of N,N-dimethylformamide dimethylacetal in 85 ml of dimethylformamide for 12 hours at 130° C. The solvent is drawn off in a rotary evaporator, the residue is taken up in methyl-tert-butyl ether and washed three times with water. After washing with saturated NaCl solution, the organic phase is dried. After the desiccant is filtered off and the solvent is spun off, the remaining residue is chromatographed on silica gel (mobile solvent ethyl acetate/hexane). 8.73 g (54.4%) of the desired compound is isolated.

$^1$H-NMR (300 MHz, CDCl$_3$): δ=7.39 (1H), 7.45 (1H), 7.68 (1H), 8.49 (1H), 8.65 (1H).

5-Nitroisoquinolin-1(2H)-one 2.51 g (13.13 mmol) of 5-nitroisocoumarin is added in 100 ml of ethanol. Ammonia is pressure-forced in an autoclave. The product precipitates and is suctioned off. 1.98 g (79.7%) of the desired compound is isolated.

$^1$H-NMR (300 MHz, DMSO-d$_6$): δ=6.97 (1H), 7.45 (1H), 7.65 (1H), 8.43 (1H), 8.57 (1H), 11.5 (1H).

5-Aminoisoquinolin-1(2H)-one 268.3 mg (1.51 mmol) of 5-nitroisoquinolin-1(2H)-one is added with 376.5 mg of ammonium chloride and 2.6 ml of water in 14 ml of ethanol and 5.4 ml of tetrahydrofuran. After addition in portions of 1.23 g of zinc powder (heating to 30 to 35° C.), it is stirred for two hours. The reaction mixture is suctioned off through a gas fiber filter and rewashed with ethyl acetate. After the filtrate is washed with water and saturated sodium chloride solution, the organic phase is dried as usual. Filtering off the desiccant and spinning off the solvent produce 196.5 mg (88.1%) of the desired amine.

$^1$H-NMR (300 MHz, DMSO-d$_6$): δ=5.6 (2H), 6.68 (1H), 6.87.45 (1H), 7.00 (1H), 7.17 (1H), 7.39 (1H), 11.7 (1H).

2-(3-Fluoro-2-methoxy-4-methylphenyl)-2-methyl-propanenitrile 14.48 g (91.56 mmol) of 2,6-difluoro-3-methylanisole is dissolved in 800 ml of toluene. After 272.2 ml (137.35 mmol) of a 0.5 molar solution of potassium hexamethyl disilazide in toluene is added, 25.31 g (366.26 mmol) of isobutyronitrile is added in drops. The batch is stirred for 10 days at room temperature and then added to a 1 M HCl solution. After being extracted three times with methyl-tert-butyl ether, the combined organic extracts are washed with saturated NaCl solution and dried. After spinning-in and chromatography on silica gel (mobile solvent ethyl acetate/hexane), 10.32 g (49.5%) of the desired compound is obtained.

$^1$H-NMR (300 MHz, CDCl$_3$): δ=1.77 (6H), 2.29 (3H), 4.09 (3H), 6.86 (1H), 6.95 (1H).

2-(3-Fluoro-2-methoxy-4-methylphenyl)-2-methyl-propanal 10.32 g (45.33 mmol) of the above-described nitrile is dissolved in 138 ml of toluene. 37.4 ml of a 1.2 molar solution of DIBAH in toluene is added in drops under a cover gas at −70° C. After three hours of stirring, 7.92 ml of isopropanol is added in drops, and after a brief stirring, 516 ml of a 10% L-(+)-tartaric acid solution is added in drops. The temperature increases, and the batch is vigorously stirred overnight at room temperature. The reaction mixture is shaken twice with methyl-tert-butyl ether. The combined organic extracts are shaken with brine, dried, and the solvent is spun off. Since the residue that is obtained (11.61 g>100%) still contains approximately 30% starting material, it is subjected one more time to the reduction conditions with the difference that during working-up, the isopropanol is eliminated. 9.94 g of a product, which in addition to the desired aldehyde also contains the starting material and the corresponding alcohol, is isolated. This mixture is mixed again with a 1.2 M DIBAH solution in toluene, but this time at −20° C. and with subsequent stirring at −10 to 0° C. to obtain a uniform compound. After the usual working-up and chromatography on silica gel (mobile solvent ethyl acetate/hexane), 5.82 g of the corresponding alcohol and 1.50 g of the aldehyde are ultimately obtained. The alcohol (5.82 g=27.42 mmol) is oxidized to aldehyde according to Swern at −78° C. After the usual working-up and chromatography on silica gel (mobile solvent ethyl acetate/hexane), 5.22 g (90.6%) of the desired aldehyde is isolated.

$^1$H-NMR (300 MHz, CDCl$_3$): δ=1.38 (6H), 2.29 (31-1), 3.85 (3H), 6.83-6.98 (2H), 9.59 (1H).

(E/Z)-4-(3-Fluoro-2-methoxy-4-methylphenyl)-4-methylpent-2-enoic acid ethyl ester 17.1 ml of a 2 molar LDA solution in THF is added in drops to a solution of 8.62 g (32.96 mmol) of 2-ethoxy-phosphonoacetic acid triethyl ester in 20 ml of absolute THF at 0° C. After 40 minutes of stirring at 0° C., 6.72 g (31.96 mmol) of 2-(3-fluoro-2-methoxy-4-methylphenyl)-2-methylpropanal, dissolved in 20 ml of THF, is added in drops at 0° C. After stirring overnight at room temperature, the reaction mixture is carefully mixed with 80 ml of water and extracted three times with methyl-tert-butyl ether. The combined organic extracts are washed with brine, dried, and the solvent is spun off after desiccant is filtered off. The residue is chromatographed on silica gel (mobile solvent ethyl acetate/hexane). 8.74 g (84.3%) of a mixture that in addition to the desired compound also contains starting material (aldehyde), which is separated in the next stage, is isolated.

(E/Z)-4-(3-Fluoro-2-methoxy-4-methylphenyl)-4-methylpent-2-enoic acid 8.74 g (26.95 mmol) of (E/Z)-4-(3-fluoro-2-methoxy-4-methylphenyl)-4-methylpent-2-enoic acid ethyl ester is mixed with 245 ml of 1N NaOH in ethanol/water (2:1) and stirred overnight at room temperature. The ethanol is drawn off in a rotary evaporator, and the residue is diluted with water and extracted twice with methyl-tert-butyl ether. The combined organic extracts contain the unreacted aldehyde from the previously described reaction. While being cooled in an ice bath, the aqueous phases are carefully acidified with concentrated hydrochloric acid to a pH of 3 and extracted three times with 300 ml each of methyl-tert-butyl ether. These ether extracts are washed with brine, dried, the solvent is spun off, and the residue (6.41 g=80.3%) is incorporated in crude form into the next stage. The recovered aldehyde is again subjected to the sequence of Horner-Wittig reaction and subsequent saponification. As a result, another 2.29 g of the desired compound (E/Z)-4-(3-fluoro-2-methoxy-4-methylphenyl)-

4-methylpent-2-enoic acid is obtained. Since the compound is an E/Z mixture (no 1:1 ratio), only the location of signals is indicated in the NMR spectrum.

$^1$H-NMR (300 MHz, CDCl$_3$): δ=0.98, 1.40, 1.53, 2.21, 3.38, 3.75-3.88, 6.72-6.85, 7.00.

4-(3-Fluoro-2-methoxy-4-methylphenyl)-4-methyl-2-oxo-pentanoic acid 8.70 g (29.36 mmol) of the (E/Z)-4-(3-fluoro-2-methoxy-4-methylphenyl)-4-methylpent-2-enoic acid that is obtained from the previous batch is mixed with 139 ml of a 1 molar sulfuric acid and 13.9 ml of glacial acetic acid, and it is stirred for two days at a bath temperature of 90° C. After cooling, the batch is made basic with solid potassium carbonate (caution, foaming). It is extracted three times with methyl-tert-butyl ether, and the combined organic extracts are discarded while being monitored by TLC. The aqueous phase is acidified with concentrated hydrochloric acid and shaken three times with methyl-tert-butyl ether. The ether extracts are washed with brine, dried, and the solvent is spun off. The remaining residue (6.04 g=76.6%) is incorporated in crude form into the next stage.

$^1$H NMR (300 MHz, CDCl$_3$): δ=1.48 (6H), 2.25 (3H), 3.50 (2H), 3.93 (3H), 6.82 (1H), 6.95 (1H).

4-(3-Fluoro-2-methoxy-4-methylphenyl)-4-methyl-2-oxo-pentanoic acid ethyl ester 6.04 g (22.52 mmol) of 4-(3-fluoro-2-methoxy-4-methylphenyl)-4-methyl-2-oxo-pentanoic acid is dissolved in 140 ml of ethanol, mixed with 2.5 ml of sulfuric acid, and refluxed for six hours. The ethanol is drawn off in a rotary evaporator, and the residue is carefully mixed with 300 ml of saturated sodium bicarbonate solution. It is extracted three times with ethyl acetate. The combined organic extracts are washed once with saturated sodium bicarbonate solution and once with brine. After drying, and after the desiccant is filtered off and the solvent is spun in, the residue is chromatographed on silica gel (mobile solvent ethyl acetate/hexane). 5.58 g (83.7%) of the desired compound is isolated.

$^1$H-NMR (300 MHz, CDCl$_3$): δ=1.29 (3H), 1.47 (6H), 2.23 (3H), 3.40 (2H), 3.95 (3H), 4.17 (2H), 6.79 (1H), 6.90 (1H).

4-(3-Fluoro-2-methoxy-4-methylphenyl)-4-methyl-2-trifluoromethyl-2-trimethylsilyloxy-pentanoic acid ethyl ester 5.58 g (18.83 mmol) of 4-(3-fluoro-2-methoxy-4-methylphenyl)-4-methyl-2-oxo-pentanoic acid ethyl ester is dissolved in 30 ml of THF and mixed at 0° C. with 3.21 g (22.6 mmol) of (trifluoromethyl)-trimethylsilane and 46.1 mg of tetrabutylammonium fluoride. After six hours of stirring between 0 and 5° C., the batch is added to ice water. It is extracted three times with methyl-tert-butyl ether, and the combined organic extracts are washed with brine. After chromatography on silica gel (mobile solvent ethyl acetate/hexane), 7.5 g (90.8%) of the desired compound is obtained.

4-(3-Fluoro-2-methoxy-4-methylphenyl)-4-methyl-2-(trifluoromethyl)-pentane-1,2-diol 7.5 g (17.1 mmol) of 4-(3-fluoro-2-methoxy-4-methylphenyl)-4-methyl-2-(trifluoromethyl)-2-trimethylsilyloxy-pentanoic acid ethyl ester is dissolved in 60 ml of diethyl ether, and it is mixed at 0 to 5° C. in portions with 1.3 g (34.2 mmol) of LiAlH$_4$. After five hours of stirring at room temperature, 60 ml of saturated NaHCO$_3$ is carefully added in drops to the reaction mixture while being cooled in an ice bath. It is stirred vigorously for one hour at room temperature. After extraction with methyl-tert-butyl ether, the organic phases are shaken with brine, dried, and the solvent is spun off. After chromatography on silica gel (mobile solvent ethyl acetate/hexane), 3.65 g (65.8%) of the desired diol is obtained.

MS (Cl): 342 (100%), 181 (18%).

4-(3-Fluoro-2-methoxy-4-methylphenyl)-2-hydroxy-4-methyl-2-trifluoromethyl)pentanal 1.57 g (12.31 mmol) of oxalyl chloride is introduced into 27 ml of dichloromethane and cooled to −78° C. After 1.93 g of DMSO, dissolved in 5.2 ml of dichloromethane, is added in drops, the batch is stirred for five more minutes. Then, 3.65 (11.26 mmol) of 4-(3-fluoro-2-methoxy-4-methylphenyl)-4-methyl-2-(trifluoromethyl)-pentane-1,2-diol, dissolved in 11.5 milliliters of dichloromethane, is added in drops. After two hours of stirring, the batch is carefully mixed with 6.61 ml (56.28 mmol) of triethylamine. After one and one-half hours of vigorous stirring at room temperature, water is added, and the batch is shaken twice with dichloromethane. The combined organic extracts are washed with 1% sulfuric acid, saturated sodium bicarbonate solution and brine. After the organic phase is dried, the solvent is spun off. 2.79 g (76.9%) of the aldehyde, which is further used in crude form, remains.

$^1$H-NMR (300 MHz, CDCl$_3$): δ=1.41 (3H), 1.45 (3H), 2.15-2.30 (5H), 3.29 (1H), 3.60 (1H), 4.02 (3H), 6.70-6.82 (2H), 9.10 (1H).

(rac.)-5-{[4-(3-Fluoro-2-methoxy-4-methylphenyl)-2-hydroxy-4-methyl-2-trifluoromethyl)pentylidene]amino}isoquinolin-1(2H)-one 150 mg (0.465 mmol) of 4-(3-fluoro-2-methoxy-4-methylphenyl)-2-hydroxy-4-methyl-2-(trifluoromethyl)pentanal, 74.5 mg (0.465 mmol) of 5-amino-isoquinolin-1(2H)-one and 264.4 mg (0.930 mmol) of titanium tetraisopropylate are stirred in 2.5 ml of xylene for five hours at 120° C. The mixture is diluted with ethyl acetate and washed once with brine. The solvent is spun off, and the residue is chromatographed on a Flashmaster. 98.6 mg (45.6%) of the desired compound is isolated.

$^1$H-NMR (300 MHz, CDCl$_3$): δ=1.40 (3H), 1.58 (3H), 1.89 (3H), 2.29 (1H), 3.30 (1H), 4.00 (3H), 4.79 (1H), 6.38 (1H), 6.67-6.78 (2H), 6.80 (1H), 7.20 (1H), 7.38 (1H), 7.55 (1H), 8.32 (1H), 11.0 (1H).

(rac.) 5-{[6-Fluoro-2-hydroxy-5-methoxy-4,4,7-trimethyl-2-(trifluoromethyl)-1,2,3,4-tetrahydronaphthalen-1-yl]amino}-isoquinolin-1(2H)-one)

1.39 ml (1.27 mmol) of titanium tetrachloride is carefully added in drops at 0° C. to 98.6 mg (0.212 mmol) of the compound rac-5-{[4-(3-fluoro-2-methoxy-4-methylphenyl)-2-hydroxy-4-methyl-2-trifluoromethyl)pentylidene]amino}isoquinolin-1-(2H)-one that is described in the previous paragraph, and then it is stirred for three hours at room temperature. The reaction mixture is carefully mixed at 0° C. with saturated sodium bicarbonate solution. After being extracted three times with ethyl acetate, the combined organic extracts are washed with saturated NaCl solution. After drying on sodium sulfate, the solvent is spun off, and the remaining residue is chromatographed on a Flashmaster. 63.3 mg (64.2%) of the desired compound is isolated.

¹H-NMR (300 MHz, CD₃OD): δ=1.52 (3H), 1.67 (3H), 2.05-2.20 (5H), 3.98 (3H), 5.10 (1H), 6.80-6.95 (2H), 7.08 (1H), 7.19 (1H), 7.40 (1H), 7.70 (1H).

(rac.) 5-{[6-Fluoro-2-,5-dihydroxy-4,4,7-trimethyl-2-(trifluoromethyl)-1,2,3,4-tetrahydronaphthalen-1-yl]amino}-isoquinolin-1(2H)-one 59.7 mg (0.128 mmol) of (rac.) 5-{[6-fluoro-2-hydroxy-5-methoxy-4,4,7-trimethyl-2-(trifluoromethyl)-1,2,3,4-tetrahydronaphthalen-1-yl]amino}-isoquinolin-1-(2H)-one is mixed at 0° C. with 1.3 ml of a 1 molar solution of boron tribromide in dichloromethane, and it is stirred for one hour at 0 to 5° C. At −10° C., saturated sodium bicarbonate solution is now carefully added in drops. After 10 minutes of vigorous stirring at room temperature, the batch is extracted three times with methyl-tert-butyl ether. The organic phases are dried, and the residue is chromatographed on a Flashmaster after the solvent is spun off. 46.5 mg (80.3%) of the desired compound is isolated.

¹H-NMR (300 MHz, CD₃OD): δ=1.56 (3H), 1.70 (3H), 2.00-2.20 (5H), 5.09 (1H), 6.65 (1H), 6.85 (1H), 7.05 (1H), 7.18 (1H), 7.39 (1H), 7.68 (1H).

Example 2

(rac.) 5-{[6-Fluoro-2,5-dihydroxy-4,4,7-trimethyl-2-(trifluoromethyl)-1,2,3,4-tetrahydronaphthalen-1-yl]amino}-quinolin-2(1H)-one 5-Aminoquinolin-2(1H)-one 4.5 g of 5-nitroquinolin-2(1H)-one (Chem. Pharm. Bull., 29, 651 (1981)) is hydrogenated in 200 ml of ethyl acetate and 500 ml of methanol in the presence of 450 mg of palladium on activated carbon as a catalyst under normal pressure with hydrogen until the reaction is completed. The catalyst is removed by filtration through diatomaceous earth, and the reaction solution is concentrated by evaporation in a vacuum. 3.8 g of the title compound is obtained as a yellow solid.

¹H-NMR (DMSO): δ=5.85 (bs, 2H), 6.27 (d, 1H), 6.33 (d, 1H), 6.43 (d, 1H), 7.10 (t, 1H), 8.07 (d, 1H), 11.39 (bs, 1H)

rac-5-{[4-(3-Fluoro-2-methoxy-4-methylphenyl)-2-hydroxy-4-methyl-2-trifluoromethyl)pentylidene]amino}isoquinolin-2(1H)-one 150 mg (0.465 mmol) of 4-(3-fluoro-2-methoxy-4-methylphenyl)-2-hydroxy-4-methyl-2-(trifluoromethyl)pentanal (described in Example 1), 74.5 mg (0.465 mmol) of 5-amino-isoquinolin-2(1H)-one and 264.4 mg (0.930 mmol) of titanium tetraisopropylate are stirred in 2.5 ml of xylene for five hours at 120° C. The mixture is diluted with ethyl acetate and washed once with brine. The solvent is spun off, and the residue is chromatographed on a Flashmaster. 132.2 mg (61.2%) of the desired compound is isolated.

¹H-NMR (300 MHz, CDCl₃): δ=1.40 (3H), 1.56 (3H), 1.82 (3H), 2.29 (1H), 3.28 (1H), 3.98 (3H), 4.70 (1H), 6.30-6.45 (2H), 6.70-6.80 (2H), 7.30 (1H), 7.40 (1H), 7.63 (1H), 8.07 (1H), 12.27 (1H).

(rac.) 5-{[6-Fluoro-2-hydroxy-5-methoxy-4,4,7-trimethyl-2-(trifluoromethyl)-1,2,3,4-tetrahydronaphthalen-1-yl]amino}-isoquinolin-2(1H)-one 1.86 ml (1.708 mmol) of titanium tetrachloride is carefully added in drops at 0° C. to 132.2 mg (0.285 mmol) of the compound rac-5-{[4-(3-fluoro-2-methoxy-4-methylphenyl)-2-hydroxy-4-methyl-2-(trifluoromethyl)pentylidene]amino}isoquinolin-2(1H)-one that is described in the preceding paragraph, and then it is stirred for three hours at room temperature. The reaction mixture is carefully mixed with saturated sodium bicarbonate solution at 0° C. After being extracted three times with ethyl acetate, the combined organic extracts are washed with saturated NaCl solution. After drying on sodium sulfate, the solvent is spun off, and the remaining residue is chromatographed on a Flashmaster. 106.7 mg (80.7%) of the desired compound is isolated.

¹H-NMR (300 MHz, CDCl₃): δ=1.52 (3H), 1.68 (3H), 1.98-2.25 (5H), 3.95 (3H), 4.60 (1H), 4.99 (1H), 5.49 (1H), 6.49-6.62 (3H), 6.80 (1H), 7.35 (1H), 8.16 (1H), 10.40 (1H).

(rac.) 5-{[6-Fluoro-2,5-dihydroxy-4,4,7-trimethyl-2-(trifluoromethyl)-1,2,3,4-tetrahydronaphthalen-1-yl]amino}-isoquinolin-2(1H)-one)

101.4 mg (0.218 mmol) of (rac.) 5-{[6-fluoro-2-hydroxy-5-methoxy-4,4,7-trimethyl-2-(trifluoromethyl)-1,2,3,4-tetrahydronaphthalen-1-yl]amino}-isoquinolin-2(1H)-one is mixed at 0° C. with 2.2 ml of a 1 molar solution of boron tribromide in dichloromethane, and it is stirred for one hour at 0 to 5° C. At −10° C., saturated sodium bicarbonate solution is now carefully added in drops. After 10 minutes of vigorous stirring at room temperature, the batch is extracted three times with methyl-tert-butyl ether. The organic phases are dried, and the residue is chromatographed on a Flashmaster after the solvent is spun off. 93.7 mg (95.3%) of the desired compound is isolated.

¹H-NMR (300 MHz, CD₃OD): δ=1.58 (3H), 1.69 (3H), 2.00-2.20 (5H), 5.10 (1H), 6.51 (1H), 6.55-6.74 (3H), 7.39 (1H), 8.22 (1H).

Example 3

(rac.) 6-Fluoro-1-[(8-fluoro-2-methylquinazolin-5-yl)amino]-4,4,7-trimethyl-2-(trifluoromethyl)-1,2,3,4-tetrahydronaphthalene-2,5-diol 5-Amino-8-fluoro-2-methylquinazoline A solution of 2.4 g (18.6 mmol) of 2,5-difluoroaniline in 11 ml of water and 1.6 ml of concentrated hydrochloric acid (37%) that is 50° C. and that was previously stirred for one hour at this temperature is added to a solution of 3.35 g (20.25 mmol) of chloral hydrate and 21.27 g (149.7 mmol) of sodium sulfate in 72 ml of water. It is stirred for another 30 minutes at room temperature, and after 4.09 g (58.9 mmol) of hydroxylammonium chloride in 19 ml of water is added over 45 minutes, it is heated to 125° C. and kept at this temperature for 5 minutes. After cooling and after another hour, the deposited light brown precipitate is filtered off, washed with water and dried. 3.0 g (15.0 mmol) of the hydroxylimine is obtained as an intermediate product that is dissolved in portions in 15 ml of concentrated sulfuric acid at 60° C. After addition is completed, it is heated for 2 hours to 80° C. and for 4 hours to 90° C. It is allowed to cool, and the solution is poured onto 100 g of ice. It is extracted with ethyl acetate, the organic phase is washed with water, dried on sodium sulfate and concentrated by evaporation. After chromatography on silica gel with hexane-ethyl acetate (0-45%), 1.2 g (7.1 mmol) of the 4,7-difluoroisatin is obtained. 1.8 ml of a 30% hydrogen peroxide solution is added in drops to isatin in 30 ml of a 1 molar sodium hydroxide solution over 10 minutes. After 2 hours of stirring at room temperature, it is cooled to 0° C., and 5 ml of a 4 molar hydrochloric acid is added and diluted with 50 ml of water. It is extracted with ethyl acetate, dried on sodium sulfate, concentrated by evaporation, and 1.27 g of 3,6-difluoroanthranilic acid, which is reacted without further purification, is thus quantitatively obtained. The 3,6-difluoroanthranilic acid is heated, in 8 ml of acetic acid anhydride for 45 minutes to 100° C. After cooling, the acetic acid that is produced and excess acetic acid anhydride are removed azeotropically with toluene in a vacuum. The residue is mixed with 40 ml of a 25% ammonia solution while being cooled with ice, and it is stirred for 72 hours. It is diluted with water and acidified with acetic acid. It is extracted with ethyl acetate, the organic phase is washed with water, dried on sodium sulfate and concentrated by evaporation. The thus obtained 1.03 g (5.25 mmol) of 5,8-difluoro-2-methyl-3H-quinazolin-4-one and 6 g of phosphorus pentachloride are heated in 20 ml of phosphoryl chloride over 12 hours to 125° C. After cooling, it is poured into saturated $NaHCO_3$ solution and extracted with ethyl acetate. The organic phase is dried, and the solvent is removed. 1.7 g of 4-chloro-5,8-difluoro-2-methylquinazoline, which is dissolved in 60 ml of ethyl acetate and 5 ml of triethylamine, is obtained quantitatively. 600 mg of palladium on carbon is added and shaken for 2 hours (480 ml of hydrogen absorption) under a hydrogen atmosphere at normal pressure. Catalyst is removed from the solution by means of filtration on Celite, whereby it is rewashed with 100 ml of ethanol and concentrated by evaporation. After chromatography on silica gel with hexane-ethyl acetate-ethanol (0-40%), 550 mg of 5,8-difluoro-2-methylquinazoline is obtained. 890 mg (13.7 mmol) of sodium azide is added to 240 mg (1.3 mmol) of 5,8-difluoro-2-methylquinazoline, 300 mg (1.13 mmol) of 18-crown-6 in 10 ml of DMF, and the mixture is heated over 8 hours to 125° C. The solvent is removed in a vacuum, and it is chromatographed on silica gel with ethyl acetate, and 52 mg of product is obtained.

$^1$H-NMR (300 MHz, $CDCl_3$); δ=2.92 (s, 3H), 4.31 (br., 2H), 6.67 (dd, 1H), 7.38 (dd, 1H), 9.37 (s, 1H).

1,1,1-Trifluoro-4-(3-fluoro-2-methoxy-3-methylphenyl)-2-[(8-fluoro-2-methyl-quinazolyl-5-yl)iminomethyl]-4-methylpentan-2-ol 150 mg (0.465 mmol) of 4-(3-fluoro-2-methoxy-4-methylphenyl)-2-hydroxy-4-methyl-2-(trifluoromethyl)pentanal (described in Example 1), 83.7 mg (0.465 mmol) of 5-amino-8-fluoro-2-methylquinazoline and 264.4 mg (0.930 mmol) of titanium tetraisopropylate are stirred in 2.5 ml of xylene for five hours at 120° C. The mixture is diluted with ethyl acetate and washed once with brine. The solvent is spun off, and the residue is chromatographed on a Flashmaster. 152.8 mg (68.2%) of the desired compound is isolated.

$^1$H-NMR (300 MHz, $CDCl_3$): δ=1.40 (3H), 1.55-1.66 (6H), 2.29 (1H), 3.00 (3H), 3.30 (1H), 3.98 (3H), 4.60 (1H), 6.29 (1H), 6.67 (1H), 6.78 (1H), 7.43 (1H), 7.71 (1H), 9.49 (1H).

(rac.) 6-Fluoro-1-[(8-fluoro-2-methylquinazolin-5-yl)amino]-5-methoxy-4,4,7-trimethyl-2-(trifluoromethyl)-1,2,3,4-tetrahydronaphthalen-2-ol 2.1 ml (1.902 mmol) of titanium tetrachloride is carefully added in drops at 0° C. to 152.8 mg (0.317 mmol) of the compound 1,1,1-trifluoro-4-(3-fluoro-2-methoxy-3-methylphenyl)-2-[(8-fluoro-2-methyl-quinazolyl-5-yl)iminomethyl]-4-methylpentan-2-ol that is described in the preceding paragraph, and then it is stirred for three hours at room temperature. The reaction mixture is carefully mixed at 0° C. with saturated sodium bicarbonate solution. After being extracted three times with ethyl acetate, the combined organic extracts are washed with saturated NaCl solution. After drying on sodium sulfate, the solvent is spun off, and the remaining residue is chromatographed on a Flashmaster. 121.8 mg (79.7%) of the desired compound is isolated.

$^1$H-NMR (300 MHz, $CDCl_3$): δ=1.57 (3H), 1.72 (3H), 2.05-2.29 (5H), 2.95 (3H), 3.97 (3H), 4.93 (1H), 5.63 (1H), 5.90 (1H), 6.68 (1H), 6.90 (1H), 7.50 (1H), 9.35 (1H).

(rac.) 6-Fluoro-1-[(8-fluoro-2-methylquinazolin-5-yl)amino]-4,4,7-trimethyl-2-(trifluoromethyl)-1,2,3,4-tetrahydronaphthalene-2,5-diol 111.2 mg (0.231 mmol) of (rac.) 6-fluoro-1-[(8-fluoro-2-methylquinazolin-5-yl)-amino]-5-methoxy-4,4,7-trimethyl-2-(trifluoromethyl)-1,2,3,4-tetrahydronaphthalen-2-ol is mixed at 0° C. with 3.2 ml of a 1 molar solution of boron tribromide in dichloromethane, and it is stirred for one and one-half hours at 0 to 5° C. At 0° C., the now carefully saturated sodium bicarbonate solution is added in drops. After 10 minutes of vigorous stirring at room temperature, the batch is extracted three times with ethyl acetate. The organic phases are dried, and the residue is chromatographed on a Flashmaster after the solvent is spun off. 66.4 mg (61.5%) of the desired compound is isolated.

$^1$H-NMR (300 MHz, $CD_3OD$): δ=1.59 (3H), 1.70 (3H), 2.00-2.20 (5H), 2.88 (3H), 5.20 (1H), 6.68 (1H), 6.85 (1H), 7.58 (1H), 9.65 (1H).

Example 4

(rac.) 5-{[6-Fluoro-2,5-dihydroxy-4,4,7-trimethyl-2-(trifluoromethyl)-1,2,3,4-tetrahydronaphthalen-1-yl]amino}-2-methylphthalazin-1-one 5-Amino-2-methyl-phthalazin-1-one 3-Bromo-4-nitro-phthalide 5.37 g of 4-nitrophthalide (Tetrahedron Lett. (2001), 42, pp. 1647-50), 8.04 g of N-bromosuccinimide, and 196 mg of benzoyl peroxide are refluxed in 80 ml of benzotrifluoride and exposed to light until the reaction is completed. It is added to water, extracted with dichloromethane, washed several times with water, dried, and the solvent is removed in a vacuum. 7.24 g of 3-bromo-4-nitro-phthalide is obtained as a solid.

$^1$H-NMR (300 MHz, $CDCl_3$), δ=7.26 (s, 1H), 7.88 (t, 1H), 8.30 (d, 1H), 8.56 (d, 1H)

5-Nitro-phthalazin-1-one 18.25 g of hydrazine sulfate and 14.88 g of sodium carbonate are stirred in 300 ml of DMF at 100° C. for one hour. Then, 7.24 g of 3-bromo-4-nitro-phthalide in 100 ml of DMF is added, and it is stirred for another 4 hours at 100° C. It is added to water, extracted several times with ethyl acetate, and the organic phase is washed with water and brine. It is dried, and the solvent is removed in a vacuum. After recrystallization from ethyl acetate, 2.35 g of 5-nitro-phthalazin-1-one is obtained as a solid.

$^1$H-NMR (300 MHz, DMSO-$d_6$), δ=8.05 (t, 1H), 8.57-8.66 (m, 2H), 8.73 (s, 1H), 13.13 (bs, 1H)

2-Methyl-5-nitro-phthalazin-1-one 1.6 g of 5-nitro-phthalazin-1-one and 2.31 g of potassium carbonate are stirred for 10 minutes at room temperature in 60 ml of DMF. 1.1 ml of methyl iodide is added, and it is stirred overnight. It is added to water, extracted several times with ethyl acetate, and the organic phase is washed with water and brine. It is dried, and the solvent is removed in a vacuum. 1.57 g of 2-methyl-5-nitro-phthalazin-1-one is obtained as a yellow solid.

$^1$H-NMR (300 MHz, DMSO-$d_6$), δ=3.73 (s, 3H), 8.05 (t, 1H), 8.62 (d, 2H), 8.75 (s, 1H)

5-Amino-2-methyl-phthalazin-1-one 1.57 g of 2-methyl-5-nitro-phthalazin-1-one and 130 mg of palladium on activated carbon are suspended in 45 ml of ethyl acetate and hydrogenated with hydrogen under normal pressure. It is filtered through diatomaceous earth, and the solvent is removed in a vacuum. 1.26 g of 5-amino-2-methyl-phthalazin-1-one is obtained as a yellow solid.

$^1$H-NMR (300 MHz, CDCl$_3$), δ=3.81 (s, 3H), 7.00 (d, 1H), 7.50 (t, 1H), 7.80 (d, 1H), 8.16 (s, 1H)

(rac.)-5-{[4-(3-Fluoro-2-methoxy-4-methylphenyl)-2-hydroxy-4-methyl-2-trifluoromethyl)pentylidene] amino}2-methyl-phthalazinon-1-one 400 mg (1.241 mmol) of (rac.) 4-(3-fluoro-2-methoxy-4-methylphenyl)-2-hydroxy-4-methyl-2-(trifluoromethyl)pentanal, 271.4 mg (1.241 mmol) of 5-amino-2-methyl-phthalazin-1-one and 705.5 mg (2.482 mmol) of titanium tetraisopropylate are stirred in seven ml of xylene for five hours at 120° C. After cooling, the mixture is diluted with ethyl acetate and washed once with brine. The aqueous phase is extracted twice with ethyl acetate. The combined organic extracts are dried, and the solvent is spun off. The residue is chromatographed on a Flashmaster. 40.9 mg (68.5%) of the desired compound is isolated.

$^1$H NMR (300 MHz, CDCl$_3$), δ=1.39 (3H), 1.60 (3H), 1.78 (3H), 2.28 (1H), 3.31 (1H), 3.90 (3H), 3.99 (3H), 4.58 (1H), 6.38 (1H), 6.78 (1H), 6.89 (1H), 7.58-7.68 (2H), 8.27-8.35 (2H).

(rac.) 5-{[6-Fluoro-2,5-dihydroxy-4,4,7-trimethyl-2-(trifluoromethyl)-1,2,3,4-tetrahydronaphthalen-1-yl] amino}-2-methylphthalazin-1-one and (rac.) 5-{[6-fluoro-2-hydroxy-5-methoxy-4,4,7-trimethyl-2-(trifluoromethyl)-1,2,3,4-tetrahydronaphthalen-1-yl] amino}-2-methylphthalazin-1-one 100 mg (0.208 mmol) of (rac.)-5-{[4-(3-fluoro-2-methoxy-4-methylphenyl)-2-hydroxy-4-methyl-2-trifluoromethyl)pentylidene]amino}2-methyl-phthalazinon-1-one is mixed at 0° C. with 2.1 ml of a 1 M solution of boron tribromide in dichloromethane, and it is stirred for two hours at 0 to 5° C. After careful mixing with saturated sodium bicarbonate solution, the batch is extracted three times with ethyl acetate. The combined organic extracts are washed with brine, dried, and the residue that remains after spinning-in is chromatographed on a Flashmaster. 38.1 mg of a mixture that consists of the desired compound and the corresponding ether is isolated. First, a separation of the ether from phenol is carried out, namely by means of HPLC (Chiralcel OD 20μ, eluants: hexane/ethanol). The respective racemates are then separated by means of chiral HPLC (Chiralpak AD 20μ, eluants: hexane/2-propanol or hexane/ethanol) into their respective enantiomers, so that the following four compounds result:

(+)-5-{[6-Fluoro-2,5-dihydroxy-4,4,7-trimethyl-2-(trifluoromethyl)-1,2,3,4-tetrahydronaphthalen-1-yl]amino}-2-methylphthalazin-1-one
(−)-5-{[6-Fluoro-2,5-dihydroxy-4,4,7-trimethyl-2-(trifluoromethyl)-1,2,3,4-tetrahydronaphthalen-1-yl]amino}-2-methylphthalazin-1-one $^1$H-NMR (300 MHz, CD$_3$OD), δ=1.59 (3H), 1.70 (3H), 2.03-2.20 (5H), 3.86 (3H), 5.20 (1H), 6.63 (1H), 7.23 (1H), 7.60-7.72 (2H), 8.58 (1H), (+)-5-{[6-Fluoro-2-hydroxy-5-methoxy-4,4,7-trimethyl-2-(trifluoromethyl)-1,2,3,4-tetrahydronaphthalen-1-yl]amino}-2-methylphthalazin-1-one $^1$H-NMR (300 MHz, CD$_3$OD), δ=1.40 (3H), 1.59 (3H), 2.09 (1H), 2.20-2.35 (4H), 152 (3H), 3.80 (3H), 5.34 (1H), 7.08 (1H), 7.52 (1H), 7.62-7.78 (2H), 8.60 (1H).

(−)-5-{[6-Fluoro-2-hydroxy-5-methoxy-4,4,7-trimethyl-2-(trifluoromethyl)-1,2,3,4-tetrahydronaphthalen-1-yl]amino}-2-methylphthalazin-1-one Example 5

(rac.) 5-{[6-Chloro-2,5-dihydroxy-4,4,7-trimethyl-2-(trifluoromethyl)-1,2,3,4-tetrahydronapthalen-1-yl] amino}-isoquinolin-1(2H)-one 2-(3-Chloro-2-methoxy-4-methylphenyl)-2-methyl-propanenitrile 17.6 g (100.8 mmol) of 2-chloro-6-fluoro-3-methylanisole is dissolved in 880 ml of toluene. After 27.8 g (403.2 mmol) of isobutyric acid nitrite is added, 302.4 ml (151.2 mmol) of a 0.5 molar solution of potassium hexamethyl disilazide in toluene is added in drops within 40 minutes (temperature increase to 27° C.). After 19 days of stirring at room temperature, the batch is mixed with 300 ml of water and 400 ml of ethyl acetate, and then acidified with 10% sulfuric acid until a pH of 4 is reached. The aqueous phase is shaken with 200 ml of ethyl acetate. The combined organic extracts are washed with water and twice with saturated NaCl solution ad then dried. After spinning-in and chromatography on silica gel (mobile solvent ethyl acetate/hexane), 12.01 g (53.4%) of the desired compound is obtained.

$^1$H-NMR (300 MHz, CDCl$_3$): δ=1.75 (6H), 2.40 (3H), 4.09 (3H), 6.99 (1H), 7.09 (1H).

2-(3-Chloro-2-methoxy-4-methylphenyl)-2-methyl-propanal 11 g (49.17 mmol) of the above-described nitrile is dissolved in 196 ml of toluene. At −65° C. to −60° C., 61.5 ml of a 1.2 molar solution of DIBAH in toluene is added in drops under nitrogen. After two hours of stirring at −65° C., 280 ml of a 20% L-(+)-tartaric acid solution is added in drops. The temperature increases to 0° C. The cold bath is removed, and the batch is vigorously stirred for two hours at room temperature. The reaction mixture is shaken twice with diethyl ether. The combined organic extracts are shaken with water and with brine, dried, and the solvent is spun off. Chromatography on silica gel (mobile solvent ethyl acetate/hexane) yields 6.12 g of the desired compound.

$^1$H-NMR (300 MHz, CDCl$_3$): δ=1.38 (6H), 2.39 (3H), 3.79 (3H), 7.03 (1H), 7.13 (1H), 9.59 (1H).

(E/Z)-4-(3-Chloro-2-methoxy-4-methylphenyl)-2-ethoxy-4-methylpent-2-enoic acid ethyl ester 14.9 ml of a 2 molar LDA solution in THF is added in drops at 0° C. within 20 minutes to a solution of 7.45 g (27.79 mmol)

of 2-ethoxy-phosphonoacetic acid triethyl ester, dissolved in 30 ml of absolute THF. After 45 minutes of stirring at 0° C., 6.3 g (27.79 mmol) of 2-(3-chloro-2-methoxy-4-methylphenyl)-2-methylpropanal, dissolved in 18 ml of THF, is quickly added in drops at 0° C. After stirring overnight at room temperature, the reaction mixture is poured into 100 ml of water and extracted twice with 250 ml each of diethyl ether. The combined organic extracts are washed with water and brine, dried, and the solvent is spun off after the desiccant is filtered off. The residue is chromatographed on silica gel (mobile solvent ethyl acetate/hexane). 8.4 g, which in addition to the desired compound also contains starting material (aldehyde), which is separated in the next stage, is isolated.

(E/Z)-4-(3-Chloro-2-methoxy-4-methylphenyl)-2-ethoxy-4-methylpent-2-enoic acid 8.4 g (24.65 mmol) of (E/Z)-4-(3-chloro-2-methoxy-4-methylphenyl)-2-ethoxy-4-methylpent-2-enoic acid ethyl ester is mixed with 246 ml of 1N NaoH in ethanol/water (2:1), and it is stirred for 19 hours at room temperature. The ethanol is drawn off in a rotary evaporator, and the residue is extracted twice with diethyl ether. The combined organic extracts are washed once with 50 ml of water. After drying, the solvent is spun off. The residue (unreacted aldehyde from the previously described reaction) is 2 g and is used again in the Horner-Wittig reaction with subsequent saponification. The combined aqueous phases are carefully acidified with concentrated hydrochloric acid to pH 3 while being cooled in an ice bath and extracted twice with 300 ml each of diethyl ether. These ether extracts are washed with water and brine, dried, the solvent is spun off, and the residue (5.62=72.9%) is incorporated in crude form into the next stage. Since the compound is an E/Z mixture in a ratio that is not 1:1, only the position of the signals is indicated in the NMR spectrum.

$^1$H-NMR (300 MHz, CDCl$_3$): δ=0.98, 1.40, 1.57, 2.31, 2.38, 3.39, 3.78, 3.80-3.90, 5.79, 6.79, 6.88-6.98, 7.18.

4-(3-Chloro-2-methoxy-4-methylphenyl)-4-methyl-2-oxo-pentanoic acid 7.30 g (23.34 mmol) of the (E/Z)-4-(3-chloro-2-methoxy-4-methylphenyl)-2-ethoxy-4-methylpent-2-enoic acid obtained from the previous batch is mixed at room temperature with 143 ml of a 1 molar sulfuric acid and 20 ml of glacial acetic acid, and it is stirred for thirty hours at a bath temperature of 90° C. After three days of stirring at room temperature, it is vigorously stirred for another two days at 90° C. While being cooled in an ice bath, the batch is made basic (pH 9) with solid potassium carbonate (caution, foaming). It is extracted twice with diethyl ether, and the combined organic extracts are discarded after TLC monitoring. While being cooled in an ice bath, the aqueous phase is acidified to pH 4 with concentrated hydrochloric acid and shaken twice with diethyl ether. The ether extracts are washed with water and brine, dried, and the solvent is spun off. The remaining residue (5.37 g=80.8%) is incorporated in crude form into the next stage.

$^1$H-NMR (300 MHz, CDCl$_3$): δ=1.50 (6H), 2.34 (3H), 3.50 (2H), 3.89 (3H), 6.97 (1H), 7.15 (1H).

4-(3-Chloro-2-methoxy-4-methylphenyl)-4-methyl-2-oxo-pentanoic acid ethyl ester 5.37 g (18.86 mmol) of 4-(3-chloro-2-methoxy-4-methylphenyl)-4-methyl-2-oxo-pentanoic acid is dissolved in 112 ml of ethanol, mixed with 2 ml of concentrated sulfuric acid and refluxed for five hours. The ethanol is drawn off in a rotary evaporator, and the residue is carefully mixed with saturated sodium bicarbonate solution after 50 ml of water is added. It is extracted twice with ethyl acetate. The combined organic extracts are washed with water and with brine. After drying, and after the desiccant is filtered off and the solvent is spun in, the residue is chromatographed on silica gel (mobile solvent ethyl acetate/hexane). 4.81 g (81.6%) of the desired compound is isolated.

$^1$H-NMR (300 MHz, CDCl$_3$): δ=1.30 (3H), 1.48 (6H), 2.36 (3H), 3.40 (2H), 3.90 (3H), 4.18 (2H), 6.92 (1H), 7.10 (1H).

(rac.) 4-(3-Chloro-2-methoxy-4-methylphenyl)-4-methyl-2-(trifluoromethyl)-2-trimethylsilyloxy-pentanoic acid ethyl ester 4.8 g (15.35 mmol) of 4-(3-chloro-2-methoxy-4-methylphenyl)-4-methyl-2-oxo-pentanoic acid ethyl ester is dissolved in 25 ml of THF, mixed at 0° C. with 2.62 g (18.41 mmol) of (trifluoromethyl)-trimethylsilane and 37.6 mg of tetrabutylammonium fluoride, and stirred for one and one-half hours between 0 and 5° C. The batch is added to 50 ml of ice water and extracted twice with diethyl ether. The combined organic extracts are washed with water and with brine. After chromatography on silica gel (mobile solvent ethyl acetate/hexane), 4.4 g (63%) of the desired compound is obtained.

$^1$H-NMR (300 MHz, CDCl$_3$): δ=0.03 (9H), 1.22 (3H), 1.38 (3H), 1.42 (3H), 2.35 (3H), 2.52 (1H), 2.69 (1H), 3.78 (1H), 3.99 (3H), 4.03 (1H), 6.90 (1H), 7.00 (1H).

(rac.) 4-(3-Chloro-2-methoxy-4-methylphenyl)-4-methyl-2-(trifluoromethyl)-2-hydroxy-pentanoic acid ethyl ester 4.4 g (9.67 mmol) of (rac.) 4-(3-chloro-2-methoxy-4-methylphenyl)-4-methyl-2-(trifluoromethyl)-2-trimethylsilyloxy-pentanoic acid ethyl ester is dissolved in 56 ml of tetrahydrofuran and mixed with 3.05 g (9.67 mmol) of tetrabutylammonium fluoride trihydrate and stirred for one and one-half hours at room temperature. The reaction mixture is diluted with water and extracted twice with diethyl ether. The organic phases are washed with water and with brine. After drying, the solvent is spun off, and the remaining residue is chromatographed on silica gel (mobile solvent ethyl acetate/hexane). 1.26 g of the desired compound is isolated.

$^1$H-NMR (300 MHz, CDCl$_3$): δ=1.20 (3H), 1.40 (3H), 1.49 (3H), 2.29-2.40 (4H), 2.82 (1H), 3.55 (1H), 3.65 (1H), 3.98 (3H), 4.08 (1H), 6.90 (1H), 7.02 (1H).

(rac.) 4-(3-Chloro-2-methoxy-4-methylphenyl)-2-hydroxy-4-methyl-2-(trifluoromethyl)pentanal and (rac.) 4-(3-chloro-2-methoxy-4-methylphenyl)-4-methyl-2-(trifluoromethyl)-pentane-1,2-diol 1.05 g (2.74 mmol) of (rac.) 4-(3-chloro-2-methoxy-4-methylphenyl)-4-methyl-2-(trifluoromethyl)-2-hydroxy-pentanoic acid ethyl ester is dissolved in 10 ml of diethyl ether and mixed at 0° C. in portions with 78 mg (2.06 mmol) of LiAlH$_4$. After one hour of stirring at 0° C. and another hour of stirring between 0 and 10° C., the reaction mixture is mixed drop by drop with 2.4 ml of saturated NaHCO$_3$ solution while being cooled in an ice bath. It is stirred for 30 minutes while being cooled in an ice bath and vigorously stirred at room temperature for one and one-half hours. The precipitate is suctioned off, washed with ethyl acetate, and the filtrate is concentrated by evaporation in a rotary evaporator. After the residue is chromatographed on silica gel (mobile solvent ethyl acetate/hexane), 425 mg (45.8%) of the aldehyde and 420.4 mg (44.9%) of the diol are obtained.

Aldehyde: $^1$H-NMR (300 MHz, CDCl$_3$): δ=1.46 (3H), 1.49 (3H), 2.28 (1H), 2.39 (3H), 3.30 (1H), 3.59 (1H), 4.00 (3H), 6.89-7.00 (2H), 9.06 (1H)

Alcohol: $^1$H-NMR (300 MHz, CDCl$_3$): δ=1.48 (3H), 1.57 (3H), 1.82 (1H), 2.20 (1H), 2.38 (3H), 2.55 (1H), 2.91 (1H), 3.29-3.46 (2H), 4.00 (3H), 6.96 (1H), 7.16 (1H).

(rac.)-5-{[4-(3-Chloro-2-methoxy-4-methylphenyl)-2-hydroxy-4-methyl-2-(trifluoromethyl)pentylidene]amino}isoquinolin-1(2H)-one 225 mg (0.664 mmol) of (rac.) 4-(3-chloro-2-methoxy-4-methylphenyl)-2-hydroxy-4-methyl-2-(trifluoromethyl)-pentanal, 106.3 mg (0.664 mmol) of 5-amino-isoquinolin-1 (2H)-one, and 0.39 ml (1.328 mmol) of titanium tetraisopropylate are stirred in 3.6 ml of o-xylene for two and one-half hours at 120° C. After cooling, the batch is poured onto 15 ml of saturated brine and diluted with ethyl acetate. After 20 minutes of vigorous stirring at room temperature, it is filtered via a column, filled with Extrelute. The residue is on silica gel (mobile solvent ethyl acetate/hexane). 224.7 mg (70.3%) of the desired compound is isolated.

$^1$H-NMR (300 MHz, DMSO-d$_6$): δ 1.49 (3H), 1.52 (3H), 1.89 (3H), 2.25 (1H), 3.04 (1H), 3.89 (3H), 6.15 (1H), 6.65 (1H), 6.72 (1H), 6.79 (1H), 6.99 (1H), 7.20 (1H), 7.37 (1H), 7.57 (1H), 8.06 (1H), 11.35 (1H).

(rac.) 5-{[6-Chloro-2-hydroxy-5-methoxy-4,4,7-trimethyl-2-(trifluoromethyl)-1,2,3,4-tetrahydronaphthalen-1-yl]amino}-isoquinolin-1(2H)-one 130 mg (0.27 mmol) of the compound (rac.)-5-{[4-(3-chloro-2-methoxy-4-methylphenyl)-2-hydroxy-4-methyl-2-trifluoromethyl)pentylidene]amino}-isoquinolin-1(2H)-one, described in the preceding paragraph, is dissolved in 1.6 ml of dichloromethane and mixed drop by drop at 0° C. with 0.8 ml (0.81 mmol) of titanium tetrachloride and then stirred for two and one-half hours at room temperature. The reaction mixture is mixed carefully with saturated sodium bicarbonate solution (pH 8) at 0° C. It is diluted with ethyl acetate, the cold bath is removed, and it is stirred vigorously for 15 minutes at room temperature. After being extracted twice with ethyl acetate, the combined organic extracts are washed with brine. After drying on sodium sulfate, the solvent is spun off, and the remaining residue is chromatographed on silica gel. 71.3 mg (54.8%) of the desired compound is isolated.

$^1$H-NMR (300 MHz, CD$_3$OD): δ=1.55 (3H), 1.65 (3H), 2.05-2.28 (5H), 3.95 (3H), 5.14 (1H), 6.85 (1H), 7.00-7.12 (2H), 7.19 (1H), 7.40 (1H), 7.70 (1H).

(rac.) 5-{[6-Chloro-2,5-dihydroxy-4,4,7-trimethyl-2-(trifluoromethyl)-1,2,3,4-tetrahydronaphthalen-1-yl]amino}-isoquinolin-1(2H)-one 40 mg (0.083 mmol) of (rac.) 5-{[6-chloro-2-hydroxy-5-methoxy-4,4,7-trimethyl-2-(trifluoromethyl)-1,2,3,4-tetrahydronaphthalen-1-yl]amino}-isoquinolin-1(2H)-one is mixed at room temperature with 0.8 ml of a 1 molar solution of boron tribromide in dichloromethane, and it is stirred for four hours at room temperature. Since starting material is still present, another 0.8 ml of boron tribromide solution is added, and it is stirred for 16 hours at room temperature. The reaction mixture is mixed drop by drop with saturated sodium bicarbonate solution (pH 8) at −30° C. The batch is mixed with ethyl acetate, and the cold bath is removed. After 10 minutes of vigorous stirring at room temperature, the batch is extracted twice with ethyl acetate. The organic phases are washed with water and with brine, dried, and the residue is chromatographed on silica gel (mobile solvent methanol/dichloromethane) after the solvent is spun off 19.9 mg (51.2%) of the desired compound is isolated.

$^1$H-NMR (300 MHz, DMSO-d$_6$): δ=1.50 (3H), 1.65 (3H), 1.92-2.20 (5H), 5.28 (1H), 5.90 (1H), 6.09 (1H), 6.69 (1H), 6.80 (1H), 7.03 (1H), 7.18 (1H), 7.25 (1H), 7.50 (1H), 8.90 (1H), 11.24 (1H).

Example 6

(rac.) 5-{[6-Chloro-2,5-dihydroxy-4,4,7-trimethyl-2-(trifluoromethyl)-1,2,3,4-tetrahydronaphthalen-1-yl]amino}-quinolin-2(1H)-one (rac.)-5-{[4-(3-Chloro-2-methoxy-4-methylphenyl)-2-hydroxy-4-methyl-2-trifluoromethyl)pentylidene]amino}isoquinolin-2(1H)-one 225 mg (0.664 mmol) of (rac.) 4-(3-chloro-2-methoxy-4-methylphenyl)-2-hydroxy-4-methyl-2-(trifluoromethyl)pentanal (described in Example 5) and 106.3 mg (0.664 mmol) of 5-amino-isoquinolin-2-(1H)-one (described in Example 2) are mixed with 3.6 ml of xylene. After 0.39 ml (1.328 mmol) of titanium tetraisopropylate is added, the batch is stirred for two and one-half hours at 120° C. The mixture is added to 15 ml of saturated brine and diluted with 20 ml of ethyl acetate. The reaction mixture is filtered over Extrelute and washed with 300 ml of a mixture that consists of ethyl acetate/dichloromethane. The solution that is obtained is spun in, and the residue is chromatographed on silica gel (mobile solvent ethyl acetate/hexane). 248.5 mg (77.8%) of the desired compound is isolated.

$^1$H-NMR (300 MHz, DMSO-d$_6$): δ=1.38 (3H), 1.53 (3H), 1.85 (3H), 2.20 (1H), 3.05 (1H), 3.85 (3H), 6.18 (1H), 6.32 (1H), 6.52 (1H), 6.65 (1H), 7.00 (1H), 7.18 (1H), 7.39 (1H), 7.58 (1H), 8.09 (1H), 11.78 (1H).

(rac.) 5-{[6-Chloro-2-hydroxy-5-methoxy-4,4,7-trimethyl-2-(trifluoromethyl)-1,2,3,4-tetrahydronaphthalen-1-yl]amino}-isoquinolin-2(1H)-one 0.8 ml (0.81 mmol) of titanium tetrachloride is added drop by drop at 0° C. to 130 mg (0.270 mmol) of the compound (rac.)-5-{[4-(3-chloro-2-methoxy-4-methylphenyl)-2-hydroxy-4-methyl-2-trifluoromethyl)pentylidene]amino}isoquinolin-2(1H)-one, dissolved in 1.6 ml of dichloromethane, that is described in the preceding paragraph, and the batch is then stirred for two hours at 0° C. and for two hours at room temperature. The reaction mixture is mixed drop by drop at 0° C. with saturated sodium bicarbonate solution and with ethyl acetate. After the cold bath is removed, it is vigorously stirred for another 15 minutes at room temperature. After being extracted twice with ethyl acetate, the combined organic extracts are washed with saturated NaCl solution. After drying on sodium sulfate, the solvent is spun off, and the remaining residue is chromatographed on silica gel (mobile solvent ethyl acetate/hexane). 82 mg (63.1%) of the desired compound is isolated.

$^1$H-NMR (300 MHz, CDCl$_3$): δ=1.53 (3H), 1.66 (3H), 2.00-2.25 (5H), 3.96 (3H), 4.80 (1H), 5.01 (1H), 5.58 (1H), 6.49-6.62 (3H), 6.92 (1H), 7.35 (1H), 8.19 (1H), 10.25 (1H).

(rac.) 5-{[6-Chloro-2,5-dihydroxy-4,4,7-trimethyl-2-
(trifluoromethyl)-1,2,3,4-tetrahydronaphthalen-1-yl]
amino}-isoquinolin-2(1H)-one 43 mg (0.089 mmol) of (rac.) 5-{[6-chloro-2-hydroxy-5-methoxy-4,4,7-trimethyl-2-(trifluoromethyl)-1,2,3,4-tetrahydronaphthalen-1-yl]amino}-isoquinolin-2(1H)-one is mixed at room temperature with 0.9 ml of a 1 molar solution of boron tribromide in dichloromethane, and it is stirred for two and one-fourth hours at room temperature. Saturated sodium bicarbonate solution is now added drop by drop at −30° C. After dilution with ethyl acetate, the cold bath is removed, and the batch is extracted twice with ethyl acetate after 10 minutes of vigorous stirring at room temperature. The combined organic phases are washed with water and brine, dried, and the residue is chromatographed on silica gel after the solvent is spun off (mobile solvent methanol/dichloromethane). 37.8 mg (90.6%) of the desired compound is isolated.

$^1$H-NMR (300 MHz, CD$_3$OD): δ=1.58 (3H), 1.70 (3H), 2.00-2.24 (5H), 5.12 (1H), 6.51 (1H), 6.62 (1H), 6.70 (1H), 6.80 (1H), 7.39 (1H), 8.22 (1H).

Example 7

(rac.) 6-Chloro-1-[(8-fluoro-2-methylquinazolin-5-yl)amino]-4,4,7-trimethyl-2-(trifluoromethyl)-1,2,3,
4-tetrahydronaphthalene-2,5-diol (rac.) 1,1,1-Trifluoro-4-(3-chloro-2-methoxy-4-methylphenyl)-2-[(8-fluoro-2-methyl-quinazolyl-5-yl)
iminomethyl]-4-methylpentan-2-ol 225 mg (0.664 mmol) of (rac.) 4-(3-chloro-2-methoxy-4-methylphenyl)-2-hydroxy-4-methyl-2-(trifluoromethyl)pentanal (described in Example 5) and 117.6 mg (0.664 mmol) of 5-amino-8-fluoro-2-methylquinazoline are mixed with 3.6 ml of o-xylene. After 0.39 ml (1.328 mmol) of titanium tetraisopropylate is added, the batch is stirred for two hours at 120° C. The mixture is added to 15 ml of saturated brine and diluted with 20 ml of ethyl acetate. The reaction mixture is filtered through Extrelute and washed with 300 m of a mixture that consists of ethyl acetate/dichloromethane. The solution that is obtained is spun in, and the residue is chromatographed on silica gel (mobile solvent ethyl acetate/hexane). 217.5 mg (65.7%) of the desired compound is isolated.

$^1$H-NMR (300 MHz, CDCl$_3$): δ=1.40 (3H), 1.52 (3H), 1.65 (3H), 2.29 (1H), 3.00 (3H), 3.35 (1H), 3.92 (3H), 4.59 (1H), 6.48 (1H), 6.77 (1H), 7.00 (1H), 7.44 (1H), 7.78 (1H), 9.39 (1H).

(rac.) 6-Chloro-1-[(8-fluoro-2-methylquinazolin-5-yl)amino]-5-methoxy-4,4,7-trimethyl-2-(trifluoromethyl)-1,2,3,4-tetrahydronaphthalen-2-ol 110 mg (0.221 mmol) of the compound (rac.) 1,1,1-trifluoro-4-(3-chloro-2-methoxy-3-methylphenyl)-2-[(8-fluoro-2-methyl-quinazolyl-5-yl)iminomethyl]-4-methyl-pentan-2-ol, described in the preceding paragraph, is dissolved in 1.3 ml of dichloromethane and carefully mixed at 0° C. with 0.66 ml (0.663 mmol) of titanium tetrachloride. Then, it is stirred for two hours at 0° C. and for two more hours at room temperature. The reaction mixture is mixed drop by drop with saturated sodium bicarbonate solution at 0° C. After dilution with ethyl acetate, the cold bath is removed, and the batch is stirred vigorously at room temperature. After being extracted twice with ethyl acetate, the combined organic extracts are washed with saturated NaCl solution. After drying on sodium sulfate, the solvent is spun off, and the remaining residue is chromatographed on silica gel (mobile solvent methanol/dichloromethane). 76.5 mg (69.5%) of the desired compound is isolated as a diastereomer mixture 9:1. The signals of the main diastereomers are indicated.

$^1$H-NMR (300 MHz, CD$_3$OD): δ=1.57 (3H), 1.69 (3H), 2.08-2.29 (5H), 2.89 (3H), 3.95 (3H), 5.28 (1H), 6.87 (1H), 7.05 (1H), 7.59 (1H), 9.65 (1H).

(rac.) 6-Chloro-1-[(8-fluoro-2-methylquinazolin-5-yl)amino]-4,4,7-trimethyl-2-(trifluoromethyl)-1,2,3,
4-tetrahydronaphthalene-2,5-diol 40 mg (0.08 mmol) of (rac.) 6-chloro-1-[(8-fluoro-2-methylquinazolin-5-yl)-amino]-5-methoxy-4,4,7-trimethyl-2-(trifluoromethyl)-1,2,3,4-tetrahydronaphthalen-2-ol is mixed at room temperature with 0.8 ml of a 1 molar solution of boron tribromide in dichloromethane, and it is stirred for four hours at room temperature. Since no reaction was carried out, another 0.8 ml of the boron tribromide solution was added. After 16 hours of stirring at room temperature, the reaction was complete. At −30° C., saturated sodium bicarbonate solution is now carefully added in drops, and the batch is diluted with ethyl acetate. After the cold bath is removed, it is stirred vigorously at room temperature for 10 minutes. The batch is extracted twice with ethyl acetate. The combined organic phases are washed with water and with brine, dried, and the residue is chromatographed on silica gel (mobile solvent methanol/dichloromethane) after the solvent is spun off. 38.2 mg (98.4%) of the desired compound is isolated.

$^1$H-NMR (300 MHz, CD$_3$OD): δ=1.60 (3H), 1.72 (3H), 2.05-2.25 (5H), 2.88 (3H), 5.22 (1H), 6.80-6.90 (2H), 7.59 (1H), 9.68 (1H).

Example 8

(rac.) 5-{[7-Chloro-6-fluoro-2,5-dihydroxy-4,4-dimethyl-2-(trifluoromethyl)-1,2,3,4-tetrahydronaphthalen-1-yl]amino}-isoquinolin-1(2H)-one 2-(4-Chloro-3-fluoro-2-methoxyphenyl)-2-methyl-propanenitrile 16.7.8 g (93.97 mmol) of 3-chloro-2,6-difluoroanisole is dissolved in 800 ml of toluene. After 25.97 g (375.88 mmol) of isobutyronitrile is added, 283.97 ml (140.95 mmol) of a 0.5 molar solution of potassium hexamethyl disilazide in toluene is added in drops. The temperature in this case increases to 28° C. The batch is stirred for seven days at 60° C. After mixing with water and ethyl acetate, the reaction mixture is brought to a pH of 4 with 1 M sulfuric acid. After being extracted twice with ethyl acetate, the combined organic extracts are washed with water and with saturated NaCl solution and dried. After spinning-in and chromatography on silica gel (mobile solvent ethyl acetate/hexane), 7.46 g (21.4%) of the desired compound is obtained.

$^1$H-NMR (300 MHz, CDCl$_3$): δ=1.75 (6H), 4.10 (3H), 6.95-7.14 (2H).

2-(4-Chloro-3-fluoro-2-methoxyphenyl)-2-methyl-propanal 7.46 g (32.78 mmol) of the above-described nitrile is dissolved in 131 ml of toluene. 41.1 ml of a 1.2 molar solution of DIBAH in toluene is added in drops at −65° C. to −60° C. under nitrogen. After two hours of stirring at −65° C., 374 ml of a 10% L-(+)-tartaric acid solution is added in drops. The batch is stirred overnight at room temperature. The reaction mixture is extracted three times with diethyl ether. The combined organic extracts are shaken with water and with brine, dried, and the solvent is spun off. 7.35 g (97.2%) of the desired compound is obtained, which is used as a crude product in the next stage.

(E/Z)-4-(4-Chloro-3-fluoro-2-methoxyphenyl)-2-ethoxy-4-methylpent-2-enoic acid ethyl ester 19.9 ml of a 2 molar LDA solution in THF (1.25 equivalents) is added in drops to a solution of 10.3 g (38.83 mmol) of 2-ethoxy-phosphonoacetic acid triethyl ester, dissolved in 34 ml of absolute THF, at 0° C. After 45 minutes of stirring at 0° C., 7.35 g (31.86 mmol) of 2-(4-chloro-3-fluoro-2-methoxyphenyl)-2-methylpropanal, dissolved in 21 ml of THF, is quickly added in drops at 0° C. After stirring over the weekend at room temperature, the reaction mixture is added to water and extracted three times with diethyl ether. The combined organic extracts are washed with water and brine, dried, and the solvent is spun off after the desiccant is filtered off. The residue is chromatographed on silica gel (mobile solvent ethyl acetate/hexane). 8.41 g, which in addition to the desired compound also contains the starting material (aldehyde) and which is separated in the next stage, is isolated.

(E/Z)-4-(4-Chloro-3-fluoro-2-methoxyphenyl)-2-ethoxy-4-methylpent-2-enoic acid 8.41 g (24.39 mmol) of (E/Z)-4-(4-chloro-3-fluoro-2-methoxyphenyl)-2-ethoxy-4-methylpent-2-enoic acid ethyl ester is mixed with 222 ml of 1N NaOH in ethanol/water (2:1) and stirred overnight at room temperature. The ethanol is drawn off in a rotary evaporator, and the residue is extracted three times with methyl-tert-butyl ether after mixing with water. Since the organic extracts, in addition to unreacted aldehyde, also contain the desired acid, it is extracted with 1 M NaOH. After the organic extracts are dried, the solvent is spun off. The residue (unreacted aldehyde from the previously described reaction) is 1.59 g and is used again in the Horner-Wittig reaction with subsequent saponification. The combined aqueous phases are carefully acidified with concentrated hydrochloric acid while being cooled in an ice bath and extracted three times with methyl-tert-butyl ether. These ether extracts are washed with brine, dried, the solvent is spun off, and the residue (5.99=77.5%) is incorporated in crude form into the next stage. Since the compound is an E/Z mixture in a non-1:1 ratio, only the position of the signals is indicated in the NMR spectrum.

$^1$H-NMR (300 MHz, CDCl$_3$): δ=0.98, 1.40, 1.49-1.59, 3.40, 3.78-3.90, 5.72, 6.70, 6.92-7.09.

4-(4-Chloro-3-fluoro-2-methoxyphenyl)-4-methyl-2-oxo-pentanoic acid 6.06 g (19.13 mmol) of the (E/Z)-4-(4-chloro-3-fluoro-2-methoxyphenyl)-2-ethoxy-4-methylpent-2-enoic acid that is obtained from the preceding paragraph is mixed at room temperature with 126 ml of a 1 molar sulfuric acid and 12.6 ml of glacial acetic acid, and it is stirred for nine days at a bath temperature of 90° C. While being cooled in an ice bath, the batch is made basic (pH 9) with solid potassium carbonate (caution, foaming) and extracted three times with methyl-tert-butyl ether. While being cooled in an ice bath, the aqueous phase is acidified to pH 4 with concentrated hydrochloric acid and shaken three times with methyl-tert-butyl ether. The ether extracts are washed with water and brine, dried, and the solvent is spun off. The remaining residue is 2.23 g. Since the first ether phase still contains product, the latter is concentrated by evaporation, and the solid residue is taken up in water and methyl-tert-butyl ether. After acidification, the aqueous phase is extracted twice more with methyl-tert-butyl ether. After the usual working-up, the combined organic extracts produce another 3.21 g of the desired product. Altogether, 5.44 g (98.5%) of acid, which is incorporated in crude form into the next stage, is obtained.

$^1$H-NMR (300 MHz, CDCl$_3$): δ=1.45 (6H), 3.55 (2H), 3.97 (3H), 6.95-7.10 (2H).

4-(4-Chloro-3-fluoro-2-methoxyphenyl)-4-methyl-2-oxo-pentanoic acid ethyl ester 5.44 g (18.84 mmol) of 4-(4-chloro-3-fluoro-2-methoxyphenyl)-4-methyl-2-oxo-pentanoic acid is dissolved in 117 ml of ethanol, mixed with 2.1 ml of concentrated sulfuric acid and refluxed for six hours. The reaction mixture is added to 250 ml of saturated sodium bicarbonate solution and extracted three times with ethyl acetate. The combined organic extracts are washed with saturated sodium bicarbonate solution and with brine. After drying and after the desiccant is filtered off and the solvent is spun in, 5.19 g (87%) of the desired compound is obtained.

$^1$H-NMR (300 MHz, CDCl$_3$): δ=1.30 (3H), 1.45 (6H), 3.40 (2H), 3.98 (3H), 4.20 (2H), 6.92-7.50 (2H).

(rac.) 4-(4-Chloro-3-fluoro-2-methoxyphenyl)-4-methyl-2-(trifluoromethyl)-2-trimethylsilyloxy-pentanoic acid ethyl ester 5.19 g (16.38 mmol) of 4-(4-chloro-3-fluoro-2-methoxyphenyl)-4-methyl-2-oxo-pentanoic acid ethyl ester is dissolved in 26 ml of THF, mixed at room temperature with 2.79 g (19.66 mmol) of (trifluoromethyl)-trimethylsilane and 40.1 mg of tetrabutylammonium fluoride, and it is stirred for two days. The reaction mixture is mixed with methyl-tert-butyl ether and washed with water and brine. The organic phase is dried, and the residue is chromatographed on silica gel (mobile solvent ethyl acetate/hexane) after the solvent is spun off. 4.71 g (62.6%) of the desired compound is obtained.

(rac.) 4-(4-Chloro-3-fluoro-2-methoxyphenyl)-4-methyl-2-(trifluoromethyl)-2-hydroxy-pentanoic acid ethyl ester 4.71 g (10.26 mmol) of (rac.) 4-(4-chloro-3-fluoro-2-methoxyphenyl)-4-methyl-2-(trifluoromethyl)-2-trimethylsilyloxy-pentanoic acid ethyl ester is dissolved in 57 ml of tetrahydrofuran and mixed with 3.24 g (10.26 mmol) of tetrabutylammonium fluoride trihydrate: after stirring over the weekend at room temperature, the reaction mixture is mixed with water and extracted three times with methyl-tert-butyl ether. The combined organic extracts are washed with brine. After drying, the solvent is spun off, and the remaining residue is chromatographed on silica gel (mobile solvent ethyl acetate/hexane). 3.07 g (77.4%) of the desired compound is isolated.

$^1$H-NMR (300 MHz, CDCl$_3$): δ=1.25 (3H), 1.38 (3H), 1.47 (3H), 2.45 (1H), 2.75 (1H), 3.50 (1H), 3.75 (1H), 4.03 (3H), 4.13 (1H), 6.89 (1H), 7.00 (1H).

(rac.) 4-(4-Chloro-3-fluoro-2-methoxyphenyl)-2-hydroxy-4-methyl-2-(trifluoromethyl)pentanal 1.00 g (2.59 mmol) of (rac.) 4-(4-chloro-3-fluoro-2-methoxyphenyl)-4-methyl-2-(trifluoromethyl)-2-hydroxy-pentanoic acid ethyl ester is dissolved in 9.5 ml of diethyl ether and mixed in portions with 73.7 mg (1.94 mmol) of LiAlH$_4$ at 0° C. Stirring is continued at 0° C. and a TLC is drawn off every one-quarter hour. After forty minutes of stirring at 0° C., the reaction mixture is mixed drop by drop with 2.4 ml of saturated NaHCO$_3$ solution while being cooled in an ice bath. It is vigorously stirred for 30 minutes while being cooled in an ice bath and overnight at room temperature. The precipitate is suctioned off, washed with ethyl acetate, and the filtrate is concentrated by evaporation in a rotary evaporator. After chromatography of the residue on a Flashmaster, 560.2 mg is obtained. This is a 3:2 mixture of the aldehyde with the starting ester.

(rac.)-5-{[4-(4-Chloro-3-fluoro-2-methoxyphenyl)-2-hydroxy-4-methyl-2-(trifluoromethyl)pentylidene]amino}isoquinolin-1(2H)-one 560 mg of the mixture that consists of (rac.) 4-(4-chloro-3-fluoro-2-methoxyphenyl)-2-hydroxy-4-methyl-2-(trifluoromethyl)pentanal and (rac.) 4-(4-chloro-3-fluoro-2-methoxyphenyl)-4-methyl-2-(trifluoromethyl)-2-hydroxypentanoic acid ethyl ester (since the aldehyde constitutes two thirds in the mixture, the 560.2 mg mixture corresponds to 336.1 mg (0.981 mmol) of aldehyde) is heated for two hours to 120° C. with 157.1 mg (0.981 mmol) of 5-amino-isoquinolin-1(2H)-one and 0.557 mg (1.962 mmol) of titanium tetraisopropylate in 6 ml of o-xylene. After cooling, the batch is diluted with ethyl acetate and mixed with brine. The organic phase is separated and worked up as usual. After chromatography on a Flashmaster, 144.7 mg (30.4%) of the desired compound is obtained (relative to the aldehyde portion in the mixture).

$^1$H NMR (300 MHz, CDCl$_3$): δ=1.40 (3H), 1.58 (3H), 2.38 (1H), 3.19 (1H), 4.03 (3H), 4.78 (1H), 6.65 (1H), 6.70-6.83 (3H), 7.20 (1H), 7.44 (1H), 7.62 (1H), 8.35 (1H), 10.95 (1H).

(rac.) 5-{[7-Chloro-6-fluoro-2,5-dihydroxy-4,4-dimethyl-2-(trifluoromethyl)-1,2,3,4-tetrahydronaphthalen-1-yl]amino}-isoquinolin-1(2H)-one 80.3 mg (0.166 mmol) of (rac.) 5-{[4-(4-chloro-3-fluoro-2-methoxyphenyl)-2-hydroxy-4-methyl-2-(trifluoromethyl)pentylidene]amino}isoquinolin-[1(2H)-one is mixed at room temperature with 1.7 ml of a 1 molar solution of boron tribromide in dichloromethane, and it is stirred for two and one-half hours at room temperature. The reaction mixture is mixed with ice, and then saturated sodium bicarbonate solution is added in drops (pH 8). After the ethyl acetate is added and after ten minutes of vigorous stirring at room temperature, the aqueous phase is extracted twice with ethyl acetate. The combined organic phases are washed with water and with brine, dried, and the residue is chromatographed on a Flashmaster after the solvent is spun off. 24.6 mg (31.6%) of the desired compound is isolated.

$^1$H-NMR (300 MHz, DMSO-d$_6$): δ=1.50 (3H), 1.60 (3H), 1.90-2.14 (2H), 5.31 (1H), 5.92 (1H), 6.18 (1H), 6.70 (1H), 6.80 (1H), 7.05 (1H), 7.19 (1H), 7.27 (1H), 7.52 (1H), 10.05 (1H), 11.25 (1H).

Example 9

(rac.) 7-Chloro-6-fluoro-1-[(8-fluoro-2-methylquinazolin-5-yl)amino]-4,4-dimethyl-2-(trifluoromethyl)-1,2,3,4-tetrahydronaphthalene-2,5-diol (rac.) 1,1,1-Trifluoro-4-(4-chloro-3-fluoro-2-methoxyphenyl)-2-[(8-fluoro-2-methyl-quinazolyl-5-yl)iminomethyl]-4-methylpentan-2-ol 457 mg of the mixture that consists of (rac.) 4-(4-chloro-3-fluoro-2-methoxyphenyl)-2-hydroxy-4-methyl-2-(trifluoromethyl)pentanal and (rac.) 4-(4-chloro-3-fluoro-2-methoxyphenyl)-4-methyl-2-(trifluoromethyl)-2-hydroxypentanoic acid ethyl ester (described in Example 8) (since the aldehyde in the mixture constitutes two thirds, the 457 mg mixture corresponds to 305.3 (0.891 mmol) of aldehyde) and 158 mg (0.891 mmol) of 5-amino-8-fluoro-2-methylquinazoline are mixed with 5.5 ml of o-xylene. After 506.6 mg (1.782 mmol) of titanium tetraisopropylate is added, the batch is stirred for two hours at 120° C. The mixture is diluted with ethyl acetate and mixed with brine. After ten minutes of vigorous stirring, the reaction mixture is filtered on Extrelute and eluted with dichloromethane. The solution that is obtained is spun in, and the residue is chromatographed on a Flashmaster. 295.8 mg (66.1%) of the desired compound is isolated.

$^1$H-NMR (300 MHz, CDCl$_3$): δ=1.40 (3H), 1.52 (3H), 2.34 (1H), 3.00 (3H), 3.21 (1H), 4.00 (3H), 4.59 (1H), 6.58 (1H), 6.70 (1H), 6.85 (1H), 7.49 (1H), 7.78 (1H), 9.49 (1H).

(rac.) 7-Chloro-6-fluoro-1-[(8-fluoro-2-methylquinazolin-5-yl)amino]-4,4,7-trimethyl-2-(trifluoromethyl)-1,2,3,4-tetrahydronaphthalene-2,5-diol 295.8 mg (0.589 mmol) of (rac.) 1,1,1-trifluoro-4-(4-chloro-3-fluoro-2-methoxyphenyl)-2-[(8-fluoro-2-methylquinazolyl-5-yl)iminomethyl]-4-methylpentan-2-ol is mixed at 0° C. with 6.1 ml of a 1 molar solution of boron tribromide in dichloromethane, and it is stirred for two hours at 0 to 5° C. The reaction mixture is mixed with ice. After saturated sodium bicarbonate solution is carefully added in drops, it is diluted with ethyl acetate and stirred vigorously for ten minutes. The aqueous phase is extracted twice with ethyl acetate. The organic phases are washed with water and brine, dried, and the residue is chromatographed several times on a Flashmaster after the solvent is spun off. 38 mg (13.2%) of the desired compound is isolated.

$^1$H-NMR (300 MHz, CD$_3$OD): δ=1.60 (3H), 1.70 (3H), 2.05-2.21 (2H), 2.83 (3H), 5.23 (1H), 6.80-6.92 (2H), 7.59 (1H), 9.68 (1H).

Example 10

(rac.) 7-Chloro-6-fluoro-1-[(7-fluoro-2-methylquinazolin-5-yl)amino]-4,4-dimethyl-2-(trifluoromethyl)-1,2,3,4-tetrahydronaphthalene-2,5-diol 5-Amino-7-fluoro-2-methylquinazoline 17 g (70.5 mmol) of 3,6-difluoro-2-N-pivaloylaminobenzaldehyde (L. Florvall, I. Fagervall, L. G. Larsson, S. B. Ross, *Eur. J. Med. Chem.* 34 (1999) 137-151), 9.2 g of acetamidine hydrochloride, 13.4 g of potassium carbonate and 10.4 g of molecular sieve (4A) are added together in 70 ml of butyronitrile. While being stirred vigorously, it is heated for 17 hours to 145° C., and the solvent is removed in a vacuum. After chromatography of the residue on silica gel with hexane/ethyl acetate (0-70%), 4.5 g of 7-fluoro-5-N-pivaloylamino-2-methylquinazoline is obtained. 1 g (3.82 mmol) of 7-fluoro-5-N-pivaloylamino-2-methylquinazoline is dissolved in 74 ml of toluene and cooled to −70° C. Over 30 minutes, 9.5 ml (11.4 mmol) of a 1.2 M diisobutylaluminum hydride solution in toluene is added in drops. The reaction mixture is allowed to heat to −40° C., and it is stirred for four hours at −40° C. Water is slowly added, and it is stirred for 30 minutes at room temperature until a precipitate forms, which is removed by means of filtration through Celite. The phases are separated, washed with saturated sodium chloride solution and dried on sodium sulfate. After chromatography on silica gel (mobile solvent ethyl acetate/hexane), 64 mg of the product is obtained.

$^1$H-NMR (CDCl$_3$): δ=2.83 (s, 3H), 4.67 (br., 2H), 6.50 (dd, 1H), 6.93 (dd, 1H), 9.23 (s, 1H).

(rac.) 1,1,1-Trifluoro-4-(4-chloro-3-fluoro-2-methoxyphenyl)-2-[(7-fluoro-2-methyl-quinazolyl-5-yl)iminomethyl]-4-methylpentan-2-ol 400 mg of the mixture that consists of (rac.) 4-(4-chloro-3-fluoro-2-methoxyphenyl)-2-hydroxy-4-methyl-2-(trifluoromethyl)pentanal and (rac.) 4-(4-chloro-3-fluoro-2-methoxyphenyl)-4-methyl-2-(trifluoromethyl)-2-hydroxy-pentanoic acid ethyl ester (described in Example 8) (since the aldehyde in the mixture constitutes two thirds, the 400 mg mixture corresponds to 266.6 (0.778 mmol) of aldehyde) and 137.8 mg (0.778 mmol) of 5-amino-7-fluoro-2-methylquinazoline are mixed with five ml of o-xylene. After 442.3 mg (1.56 mmol) of titanium tetraisopropylate is added, the batch is stirred for two hours at 120° C. The mixture is diluted with ethyl acetate and mixed with brine. After ten minutes of vigorous stirring, the reaction mixture is filtered through Extrelute and eluted with dichloromethane. The solution that is obtained is spun in, and the residue is chromatographed on a Flashmaster. 312.4 mg (80%) of the desired compound is isolated. The yield relates to the aldehyde that is contained in the mixture.

$^1$H-NMR (300 MHz, CDCl$_3$): δ=1.40 (3H), 1.60 (3H), 2.36 (1H), 2.92 (3H), 3.23 (1H), 4.01 (3H), 4.49 (1H), 6.49 (1H), 6.65 (1H), 6.89 (1H), 7.45 (1H), 7.79 (1H), 9.32 (1H).

(rac.) 7-Chloro-6-fluoro-1-[(7-fluoro-2-methylquinazolin-5-yl)amino]-4,4,7-trimethyl-2-(trifluoromethyl)-1,2,3,4-tetrahydronaphthalene-2,5-diol 312.4 mg (0.622 mmol) of (rac.) 1,1,1-trifluoro-4-(4-chloro-3-fluoro-2-methoxyphenyl)-2-[(7-fluoro-2-methyl-quinazolyl-5-yl)iminomethyl]-4-methylpentan-2-01 is mixed at 0° C. with 6.4 ml of a 1 molar solution of boron tribromide in dichloromethane, and it is stirred for two hours at 0 to 5° C. The reaction mixture is mixed with ice. After saturated sodium bicarbonate solution is carefully added in drops, it is diluted with ethyl acetate and stirred vigorously for ten minutes. The aqueous phase is extracted twice with ethyl acetate. The organic phases are washed with water and brine, dried, and the residue is chromatographed several times on a Flashmaster after the solvent is spun off. 51 mg (16.7%) of the desired compound is isolated.

$^1$H-NMR (300 MHz, CD$_3$OD): δ=1.60 (3H), 1.70 (3H), 2.15 (2H), 2.79 (3H), 5.31 (1H), 6.70-6.88 (3H), 9.58 (1H).

Analogously to the compounds of Examples 1-10 that are described in detail, the following structures were synthesized with use of the corresponding starting materials.

Example 11

1-(7,8-Difluoro-2-methylquinazolin-5-ylamino)-6-fluoro-5-methoxy-4,4,7-trim ethyl-2-trifluoromethyl)-1,2,3,4-tetrahydronaphthalen-2-ol Example 12

5-(7,8-Difluoro-2-methylquinazolin-5-ylamino)-2-fluoro-3,8,8-trimethyl-6-(trifluoromethyl)-5,6,7,8-tetrahydronaphthalene-1,6-diol Examples 13 and 14

1-(2-Ethylquinazolin-5-ylamino)-6-fluoro-5-methoxy-4,4,7-trimethyl-2-(trifluoromethyl)-1,2,3,4-tetrahydronaphthalen-2-ol, Diastereomer A and 1-(2-Ethylquinazolin-5-ylamino)-6-fluoro-5-methoxy-4,4,7-trimethyl-2-(trifluoromethyl)-1,2,3,4-tetrahydronaphthalen-2-ol, Diastereomer B Example 15

5-(2-Ethylquinazolin-5-ylamino)-2-fluoro-3,8,8-trimethyl-6-(tri fluoromethyl)-5,6,7,8-tetrahydronaphthalene-1,6-diol, Diastereomer A Example 16

5-(2-Ethylquinazolin-5-ylamino)-2-fluoro-3,8,8-trimethyl-6-(trifluoromethyl)-5,6,7,8-tetrahydronaphthalene-1,6-diol, Diastereomer B Examples 17 and 18

5-(2-Methylquinazolin-5-ylamino)-2-fluoro-3,8,8-trimethyl-6-(trifluoromethyl)-5,6,7,8-tetrahydronaphthalene-1,6-diol, Diastereomer A and 5-(2-Methylquinazolin-5-ylamino)-2-fluoro-3,8,8-trimethyl-6-(trifluoromethyl)-5,6,7,8-tetrahydronaphthalene-1,6-diol, Diastereomer B Examples 19 and 20

(+)-5-{[6-Fluoro-2,5-dihydroxy-4,4,7-trimethyl-2-(trifluoromethyl)-1,2,3,4-tetrahydronaphthalen-1-yl]amino}-quinolin-2(1H)-one and (−)-5-{[6-Fluoro-2,5-dihydroxy-4,4,7-trimethyl-2-(trifluoromethyl)-1,2,3,4-tetrahydronaphthalen-1-yl]amino}-quinolin-2(1H)-one 83 mg of racemic 5-{[6-fluoro-2,5-dihydroxy-4,4,7-trimethyl-2-(trifluoromethyl)-1,2,3,4-tetrahydronaphthalen-1-yl]amino}-quinolin-2(1H)-one is separated into its enantiomers on a chiral column (Chiralpak AD-H 5µ, eluants: hexane/ethanol). 34 mg of the (+)-enantiomer and 33 mg of the (−)-enantiomer are obtained.

[a]$_D$=+41.1±0.5 (c=0.51, methanol)

[a]$_D$=−41.8±0.4 (c=0.505, methanol)

Examples 21 and 22

(+)-6-Fluoro-1-[(8-fluoro-2-methylquinazolin-5-yl)amino]-4,4,7-trimethyl-2-(trifluoromethyl)-1,2,3,4-tetrahydronaphthalene-2,5-diol and (−)-6-Fluoro-1-[(8-fluoro-2-methylquinazolin-5-yl)amino]-4,4,7-trimethyl-2-(trifluoromethyl)-1,2,3,4-tetrahydronaphthalene-2,5-diol 50.8 mg of racemic 6-fluoro-1-[(8-fluoro-2-methylquinazolin-5-yl)amino]-4,4,7-trimethyl-2-(trifluoromethyl)-1,2,3,4-tetrahydronaphthalene-2,5-diol is separated into its enantiomers on a chiral column (Chiralpak AD-H 5µ, eluants: hexane/ethanol). 25.3 mg of the (+)-enantiomer and 23.8 mg of the (−)-enantiomer are isolated.

[a]$_D$=+57.8±1.1 (c=0.50, methanol)

[a]$_D$=−53.3±0.3 (c=0.50, methanol)

Example 23

5-[7-Chloro-6-fluoro-2,5-dihydroxy-4,4-dimethyl-2-(trifluoromethyl)-1,2,3,4-tetrahydronaphthalen-1-ylamino]-1H-quinolin-2-one

Example 24

5-[7-Chloro-6-fluoro-2-hydroxy-5-methoxy-4,4-dimethyl-2-(trifluoromethyl)-1,2,3,4-tetrahydronaphthalen-1-ylamino]-1,3-dihydroindol-2-one

Example 25

5-[7-Chloro-6-fluoro-2,5-dihydroxy-4,4-dimethyl-2-(trifluoromethyl)-1,2,3,4-tetrahydronaphthalen-1-ylamino]-1,3dihydroindol-2-one

Example 26

7-Chloro-1-(7,8-difluoro-2-methylquinazolin-5-ylamino)-6-fluoro-5-methoxy-4,4-dimethyl-2-(trifluoromethyl)-1,2,3,4-tetrahydronaphthalen-2-ol

Example 27

3-Chloro-5-(7,8-difluoro-2-methylquinazolin-5-ylamino)-2-fluoro-8,8-dimethyl-6-(trifluoromethyl)-5,6,7,8-tetrahydronaphthalene-1,6-diol

Examples 28 and 29

7-Chloro-1-(2-ethylquinazolin-5-ylamino)-6-fluoro-5-methoxy-4,4-dimethyl-2-(trifluoromethyl)-1,2,3,4-tetrahydronaphthalen-2-ol, Diastereomer A and 7-Chloro-1-(2-ethylquinazolin-5-ylamino)-6-fluoro-5-methoxy-4,4-dimethyl-2-(trifluoromethyl)-1,2,3,4-tetrahydronaphthalen-2-ol, Diastereomer B

Example 30

3-Chloro-5-(2-ethylquinazolin-5-ylamino)-2-fluoro-8,8-dimethyl-6-(trifluoromethyl)-5,6,7,8-tetrahydronaphthalene-1,6-diol

Examples 31 and 32

3-Chloro-5-(7-fluoro-2-methylquinazolin-5-ylamino)-2-fluoro-8,8-dimethyl-6-(trifluoromethyl)-5,6,7,8-tetrahydronaphthalene-1,6-diol, Enantiomer A and 3-Chloro-5-(7-fluoro-2-methylquinazolin-5-ylamino)-2-fluoro-8,8-dimethyl-6-(trifluoromethyl)-5,6,7,8-tetrahydronaphthalene-1,6-diol, Enantiomer B 22.5 mg of the racemic compound 3-chloro-5-(7-fluoro-2-methylquinazolin-5-ylamino)-2-fluoro-8,8-dimethyl-6-(trifluoromethyl)-5,6,7,8-tetrahydronaphthalene-1,6-diol is separated into its enantiomers on a chiral column (Chiralpak AD-H 5μ, eluants: hexane/ethanol). 10.5 mg of Enantiomer A (retention time 5.28 minutes) and 9.9 mg of Enantiomer B (retention time 10.79 minutes) are isolated.

Examples 33 and 34

(+)-3-Chloro-5-(8-fluoro-2-methylquinazolin-5-ylamino)-2-fluoro-8,8-dimethyl-6-(trifluoromethyl)-5,6,7,8-tetrahydronaphthalene-1,6-diol, Enantiomer A and (−)-3-Chloro-5-(8-fluoro-2-methylquinazolin-5-ylamino)-2-fluoro-8,8-dimethyl-6-(trifluoromethyl)-5,6,7,8-tetrahydronaphthalene-1,6-diol, Enantiomer B 40 mg of the racemic compound (+)-3-chloro-5-(8-fluoro-2-methylquinazolin-5-ylamino)-2-fluoro-8,8-dimethyl-6-(trifluoromethyl)-5,6,7,8-tetrahydronaphthalene-1,6-diol is separated into its enantiomers on a chiral column (Chiralpak AD 10μ, eluants: hexane/ethanol). In each case, 16 mg of the two enantiomers is obtained.

$[a]_D$=+53.1±0.6 (c=0.555, methanol)
$[a]_D$=−46.0±0.6 (c=0.58, methanol)

Example 35

3-Fluoro-4,7-dihydroxy-5,5-dimethyl-8-(2-oxo-1,2-dihydroquinolin-5-ylamino)-7-(trifluoromethyl)-5,6,7,8-tetrahydronaphthalene-2-carbonitrile IR (Microscope, matrix: diamond): 2232

Example 36

3-Fluoro-4,7-dihydroxy-5,5-dimethyl-8-(2-oxo-1,3-dihydroindol-4-ylamino)-7-(trifluoromethyl)-5,6,7,8-tetrahydronaphthalene-2-carbonitrile IR (Microscope, matrix: diamond): 2238

Example 37

6-Chloro-1-(7-fluoro-2-methylquinazolin-5-ylamino)-5-methoxy-4,4,7-trimethyl-2-(trifluoromethyl)-1,2,3,4-tetrahydronaphthalen-2-ol

Example 38

2-Chloro-5-(7-fluoro-2-methylquinazolin-5-ylamino)-3,8,8-trimethyl-6-(trifluoromethyl)-5,6,7,8-tetrahydronaphthalene-1,6-diol

Example 39

6-Chloro-1-(7,8-difluoro-2-methylquinazolin-5-ylamino)-5-methoxy-4,4,7-trimethyl-2-(trifluoromethyl)-1,2,3,4-tetrahydronaphthalen-2-ol

Example 40

2-Chloro-5-(7,8-difluoro-2-methylquinazolin-5-ylamino)-3,8,8-trimethyl-6-(trifluoromethyl)-5,6,7,8-tetrahydronaphthalene-1,6-diol

Example 41

4-[6-Chloro-2-hydroxy-5-methoxy-4,4,7-trimethyl-2-(trifluoromethyl)-1,2,3,4-tetrahydronaphthalen-1-ylamino]-1,3-dihydroindol-2-one

Example 42

4-[6-Chloro-2,5-dihydroxy-4,4,7-trimethyl-2-(trifluoromethyl)-1,2,3,4-tetrahydronaphthalen-1-ylamino]-1,3-dihydroindol-2-one

Example 43

6-Chloro-5-methoxy-4,4,7-trimethyl-1-(2-methylquinazolin-5-ylamino)-2-(trifluoromethyl)-1,2,3,4-tetrahydronaphthalen-2-ol

Example 44

2-Chloro-3,8,8-trimethyl-5-(2-methylquinazolin-5-ylamino)-6-(trifluoromethyl)-5,6,7,8-tetrahydronaphtalene-1,6-diol

Examples 45 and 46

(+)-6-Chloro-1-(7,8-difluoro-2-methylquinazolin-5-ylamino)-5-methoxy-4,4,7-trimethyl-2-(trifluoromethyl)-1,2,3,4-tetrahydronaphthalen-2-ol and (−)-6-Chloro-1-(7,8-difluoro-2-methylquinazolin-5-ylamino)-5-methoxy-4,4,7-trimethyl-2-(trifluoromethyl)-1,2,3,4-tetrahydronaphthalen-2-ol 88 mg of racemic 6-chloro-1-(7,8-difluoro-2-methylquinazolin-5-ylamino)-5-methoxy-4,4,7-trimethyl-2-(trifluoromethyl)-1,2,3,4-tetrahydronaphthalen-2-ol is separated on a chiral column (Chiralpak AD-H 5μ, eluants: hexane/ethanol). 42.6 mg of the (+)-enantiomer and 41.3 mg of the (−)-enantiomer are obtained.
[a]$_D$=+36.9±0.6 (c=0.50, methanol)
[a]$_D$=−32.8±0.3 (c=0.51, methanol)

Example 47

(+)-2-Chloro-5-(7,8-difluoro-2-methylquinazolin-5-ylamino)-3,8,8-trimethyl-6-(trifluoromethyl)-5,6,7,8-tetrahydronaphthalene-1,6-diol 33.9 mg of the ether ((+)-enantiomer) that is described in Example 45 is treated as usual with boron tribromide. 30.1 mg (91.4%) of the enantiomer-pure phenol is isolated.
[a]$_D$=+49.1±0.3 (c=0.55, methanol)

Example 48

(−)-2-Chloro-5-(7,8-difluoro-2-methylquinazolin-5-ylamino)-3,8,8-trimethyl-6-(trifluoromethyl)-5,6,7,8-tetrahydronaphthalene-1,6-diol 37.2 mg of the ether ((−)-enantiomer) that is described in Example 45 is treated as usual with boron tribromide. 30.9 mg (85.6%) of the enantiomer-pure phenol is isolated.
[a]$_D$=−44.7±0.4 (c=0.55, methanol)

Examples 49 and 50

(+)-6-Chloro-1-(7-fluoro-2-methylquinazolin-5-ylamino)-5-methoxy-4,4,7-trimethyl-2-(trifluoromethyl)-1,2,3,4-tetrahydronaphthalen-2-ol and (−)-6-Chloro-1-(7-fluoro-2-methylquinazolin-5-ylamino)-5-methoxy-4,4,7-trimethyl-2-(trifluoromethyl)-1,2,3,4-tetrahydronaphthalen-2-ol 143 mg of racemic 6-chloro-1-(7-fluoro-2-methylquinazolin-5-ylamino)-5-methoxy-4,4,7-trimethyl-2-(trifluoromethyl)-1,2,3,4-tetrahydronaphthalen-2-ol is separated on a chiral column (Chiralcel OD-H 5μ, eluants: hexane/ethanol). 58.4 mg of the (+)-enantiomer and 51.2 mg of the (−)-enantiomer are obtained.
[a]$_D$=+30.5±0.7 (c=0.50, methanol)
[a]$_D$=−27.3±0.8 (c=0.51, methanol)

Example 51

(+)-2-Chloro-5-(7-fluoro-2-methylquinazolin-5-ylamino)-3,8,8-trimethyl-6-(trifluoromethyl)-5,6,7,8-tetrahydronaphthalene-1,6-dial 51 mg of the ether ((+)-enantiomer) that is described in Example 49 is treated as usual with boron tribromide. 47.3 mg (95.5%) of the enantiomer-pure phenol is isolated.
[a]$_D$=+41.6±0.8 (c=0.55, methanol)

Example 52

(−)-2-Chloro-5-(7-fluoro-2-methylquinazolin-5-ylamino)-3,8,8-trimethyl-6-(trifluoromethyl)-5,6,7,8-tetrahydronaphthalene-1,6-diol 44.5 mg of the ether ((−)-enantiomer) that is described in Example 49 is treated as usual with boron tribromide. 41.4 mg (95.8%) of the enantiomer-pure phenol is isolated.
[a]$_D$=−40.2±0.6 (c=0.57, methanol)

Examples 53 and 54

(+)-5-[6-Chloro-2-hydroxy-5-methoxy-4,4,7-trimethyl-2-(trifluoromethyl)-1,2,3,4-tetrahydronaphthalen-1-ylamino]-1H-quinolin-2-one and (−)-5-[6-Chloro-2-hydroxy-5-methoxy-4,4,7-trimethyl-2-(trifluoromethyl)-1,2,3,4-tetrahydronaphthalen-1-ylamino]-1H-quinolin-2-one 124 mg of racemic 5-[6-chloro-2-hydroxy-5-methoxy-4,4,7-trimethyl-2-(trifluoromethyl)-1,2,3,4-tetrahydronaphthalen-1-ylamino]-1H-quinolin-2-one is separated on a chiral column (Chiralcel OJ-H 5μ, eluants: hexane/ethanol). 54.7 mg of the (+)-enantiomer and 47.8 mg of the (−)-enantiomer are obtained.
[a]$_D$=+37.0±0.6 (c=0.57, methanol)
[a]$_D$=−46.6±0.4 (c=0.54, methanol)

Example 55

(+)-5-[6-Chloro-2,5-dihydroxy-4,4,7-trimethyl-2-(trifluoromethyl)-1,2,3,4-tetrahydronaphthalen-1-ylamino]-1H-quinolin-2-one 47.3 mg of the ether ((+)-enantiomer) that is described in Example 53 is treated as usual with boron tribromide. 42.6 mg (92.8%) of the enantiomer-pure phenol is isolated.
[a]$_D$=+53.3±0.4 (c=0.52, methanol)

Example 56

(−)-5-[6-Chloro-2,5-dihydroxy-4,4,7-trimethyl-2-(trifluoromethyl)-1,2,3,4-tetrahydronaphthalen-1-ylamino]-1H-quinolin-2-one 42.4 mg of the ether ((−)-enantiomer) that is described in Example 53 is treated as usual with boron tribromide. 39.4 mg (95.8%) of the enantiomer-pure phenol is isolated.
[a]$_D$=−56.3±0.4 (c=0.54, methanol)

Example 57

1,6-Dihydroxy-3,8,8-trimethyl-5-(2-oxo-2,3-dihydroindol-4-ylamino)-6-(trifluoromethyl)-5,6,7,8-tetrahydronaphthalene-2-carbonitrile IR (Microscope, matrix: diamond): 2235

Example 58

5-(7-Fluoro-2-methylquinazolin-5-ylamino)-1,6-dihydroxy-3,8,8-trimethyl-6-(trifluoromethyl)-5,6,7,8-tetrahydronaphthalene-2-carbonitrile IR (Microscope, matrix: diamond): 2228

Analogously to the described compounds, the following structures can be synthesized with use of the corresponding starting materials.

3-Fluoro-4,7-dihydroxy-5,5-dimethyl-8-(1-oxo-1,2-dihydroisoquinolin-5-ylamino)-7-(trifluoromethyl)-5,6,7,8-tetrahydronaphthalene-2-carbonitrile 3-Fluoro-4,7-dihydroxy-5,5-dimethyl-8-(2-methyl-1-oxo-1,2-dihydroisoquinolin-5-ylamino)-7-(trifluoromethyl)-5,6,7,8-tetrahydronaphthalene-2-carbonitrile 3-Fluoro-4,7-dihydroxy-5,5-dimethyl-8-(2-methyl-1-oxo-1,2-dihydrophthalazin-5-ylamino)-7-(trifluoromethyl)-5,6,7,8-tetrahydronaphthalene-2-carbonitrile 3-Fluoro-4,7-dihydroxy-5,5-dimethyl-8-(1-oxo-1,2-dihydrophthalazin-5-ylamino)-7-(trifluoromethyl)-5,6,7,8-tetrahydronaphthalene-2-carbonitrile 3-Fluoro-8-(7-fluoro-2-methylquinazolin-5-ylamino)-4,7-dihydroxy-5,5-dimethyl-7-(trifluoromethyl)-5,6,7,8-tetrahydronaphthalene-2-carbonitrile 3-Fluoro-8-(8-fluoro-2-methylquinazolin-5-ylamino)-4,7-dihydroxy-5,5-dimethyl-7-(trifluoromethyl)-5,6,7,8-tetrahydronaphthalene-2-carbonitrile 3-Fluoro-8-(7,8-difluoro-2-methyl quinazolin-5-ylamino)-4,7-dihydroxy-5,5-dimethyl-7-(trifluoromethyl)-5,6,7,8-tetrahydronaphthalene-2-carbonitrile 3-Fluoro-8-(2-methylquinazolin-5-ylamino)-4,7-dihydroxy-5,5-dimethyl-7-(trifluoromethyl)-5,6,7,8-tetrahydronaphthalene-2-carbonitrile 3-Fluoro-8-(2-ethylquinazolin-5-ylamino)-4,7-dihydroxy-5,5-dimethyl-7-(trifluoromethyl)-5,6,7,8-tetrahydronaphthalene-2-carbonitrile 3-Fluoro-8-(2-methylquinolin-5-ylamino)-4,7-dihydroxy-5,5-dimethyl-7-(trifluoromethyl)-5,6,7,8-tetrahydronaphthalene-2-carbonitrile 3-Fluoro-8-(2,6-dimethylquinolin-5-ylamino)-4,7-dihydroxy-5,5-dimethyl-7-(trifluoromethyl)-5,6,7,8-tetrahydronaphthalene-2-carbonitrile 3-Fluoro-8-(6-chloro-2-methylquinolin-5-ylamino)-4,7-dihydroxy-5,5-dimethyl-7-(trifluoromethyl)-5,6,7,8-tetrahydronaphthalene-2-carbonitrile 3-Fluoro-8-(6-fluoro-2-methylquinolin-5-ylamino)-4,7-dihydroxy-5,5-dimethyl-7-(trifluoromethyl)-5,6,7,8-tetrahydronaphthalene-2-carbonitrile 3-Fluoro-4,7-dihydroxy-8-(1H-indazol-4-ylamino)-5,5-dimethyl-7-(trifluoromethyl)-5,6,7,8-tetrahydronaphthalene-2-carbonitrile 3-Fluoro-4,7-dihydroxy-5,5-dimethyl-8-(naphthalen-1-ylamino)-7-(trifluoromethyl)-5,6,7,8-tetrahydronaphthalene-2-carbonitrile 3-Fluoro-4,7-dihydroxy-5,5-dimethyl-8-(naphthalen-2-ylamino)-7-(trifluoromethyl)-5,6,7,8-tetrahydronaphthalene-2-carbonitrile 3-Fluoro-4,7-dihydroxy-5,5-dimethyl-8-(6-hydroxynaphthalen-1-ylamino)-7-(trifluoromethyl)-5,6,7,8-tetrahydronaphthalene-2-carbonitrile 3-Fluoro-4,7-dihydroxy-5,5-dimethyl-8-(5-hydroxynaphthalen-1-ylamino)-7-(trifluoromethyl)-5,6,7,8-tetrahydronaphthalene-2-carbonitrile 3-Chloro-2-fluoro-5-(6-hydroxynaphthalen-1-ylamino)-8,8-dimethyl-6-(trifluoromethyl)-5,6,7,8-tetrahydronaphthalene-1,6-diol 3-Chloro-2-fluoro-5-(5-hydroxynaphthalen-1-ylamino)-8,8-dimethyl-6-(trifluoromethyl)-5,6,7,8-tetrahydronaphthalene-1,6-diol 3-Chloro-2-fluoro-5-(naphthalen-1-ylamino)-8,8-dimethyl-6-(trifluoromethyl)-5,6,7,8-tetrahydronaphthalene-1,6-diol 3-Chloro-2-fluoro-5-(naphthalene-2-ylamino)-8,8-dimethyl-6-(trifluoromethyl)-5,6,7,8-tetrahydronaphthalene-1,6-diol 3-Chloro-2-fluoro-5-(1H-indazol-4-ylamino)-8,8-dimethyl-6-(trifluoromethyl)-5,6,7,8-tetrahydronaphthalene-1,6-diol 3-Chloro-2-fluoro-5-(5-chloro-1H-indazol-4-ylamino)-8,8-dimethyl-6-(trifluoromethyl)-5,6,7,8-tetrahydronaphthalene-1,6-diol 5-(7,8-Difluoro-2-methylquinazolin-5-ylamino)-1,6-dihydroxy-3,8,8-trimethyl-6-(trifluoromethyl)-5,6,7,8-tetrahydronaphthalene-2-carbonitrile 5-(8-Fluoro-2-methylquinazolin-5-ylamino)-1,6-dihydroxy-3,8,8-trimethyl-6-(trifluoromethyl)-5,6,7,8-tetrahydronaphthalene-2-carbonitrile 5-(2-Methylquinazolin-5-ylamino)-1,6-dihydroxy-3,8,8-trimethyl-6-(trifluoromethyl)-5,6,7,8-tetrahydronaphthalene-2-carbonitrile 5-(2-Ethylquinazolin-5-ylamino)-1,6-dihydroxy-3,8,8-trimethyl-6-(trifluoromethyl)-5,6,7,8-tetrahydronaphthalene-2-carbonitrile 1,6-Dihydroxy-3,8,8-trimethyl-5-(2-oxo-1,2-dihydroquinolin-5-ylamino)-6-(trifluoromethyl)-5,6,7,8-tetrahydronaphthalene-2-carbonitrile 1,6-Dihydroxy-3,8,8-trimethyl-5-(1-oxo-1,2-dihydroisoquinolin-5-ylamino)-6-(trifluoromethyl)-5,6,7,8-tetrahydronaphthalene-2-carbonitrile 1,6-Dihydroxy-3,8,8-trimethyl-5-(2-methyl-1-oxo-1,2-dihydroisoquinolin-5-ylamino)-6-(trifluoromethyl)-5,6,7,8-tetrahydronaphthalene-2-carbonitrile 1,6-Dihydroxy-3,8,8-trimethyl-5-(1-oxo-1,2-dihydrophthalazin-5-ylamino)-6-(trifluoromethyl)-5,6,7,8-tetrahydronaphthalene-2-carbonitrile 1,6-Dihydroxy-3,8,8-trimethyl-5-(2-methyl-1-oxo-1,2-dihydrophthalazin-5-ylamino)-6-(trifluoromethyl)-5,6,7,8-tetrahydronaphthalene-2-carbonitrile 1,6-Dihydroxy-3,8,8-trimethyl-5-(2-methylquinolin-5-ylamino)-6-(trifluoromethyl)-5,6,7,8-tetrahydronaphthalene-2-carbonitrile 1,6-Dihydroxy-3,8,8-trimethyl-5-(2,6-dimethylquinolin-5-ylamino)-6-(trifluoromethyl)-5,6,7,8-tetrahydronaphthalene-2-carbonitrile 1,6-dihydroxy-3,8,8-trimethyl-5-(6-chloro-2-methylquinolin-5-ylamino)-6-(trifluoromethyl-5,6,7,8-tetrahydronaphthalene-2-carbonitrile 1,6-Dihydroxy-3,8,8-trimethyl-5-(6-fluoro-2-methylquinolin-5-ylamino)-6-(trifluoromethyl)-5,6,7,8-tetrahydronaphthalene-2-carbonitrile 1,6-Dihydroxy-5-(1H-indazolyl-4-ylamino)-3,8,8-trimethyl-6-(trifluoromethyl)-5,6,7,8-tetrahydronaphthalene-2-carbonitrile 1,6-Dihydroxy-5-(5-chloro-1H-indazolyl-4-ylamino)-3,8,8-trimethyl-6-(trifluoromethyl)-5,6,7,8-tetrahydronaphthalene-2-carbonitrile 1,6-Dihydroxy-3,8,8-trimethyl-5-(naphthalen-1-ylamino)-6-(trifluoromethyl)-5,6,7,8-tetrahydronaphthalene-2-carbonitrile 1,6-Dihydroxy-3,8,8-trimethyl-5-(naphthalen-2-ylamino)-6-(trifluoromethyl)-5,6,7,8-tetrahydronaphthalene-2-carbonitrile 1,6-Dihydroxy-3,8,8-trimethyl-5-(6-hydroxy-naphthalen-1-ylamino)-6-(trifluoromethyl)-5,6,7,8-tetrahydronaphthalene-2-carbonitrile 1,6-Dihydroxy-3,8,8-trimethyl-5-(5-hydroxy-naphthalen-1-ylamino)-6-(trifluoromethyl)-5,6,7,8-tetrahydronaphthalene-2-carbonitrile 2-Chloro-5-(1H-indazol-4-ylamino)-3,8,8-trimethyl-6-(trifluoromethyl)-5,6,7,8-tetrahydronaphthalene-1,6-diol 2-Fluoro-5-(1H-indazol-4-ylamino)-3,8,8-trimethyl-6-(trifluoromethyl)-5,6,7,8-tetrahydronaphthalene-1,6-diol 2-Chloro-3,8,8-trimethyl-5-(naphthalen-1-ylamino 6-(trifluoromethyl)-5,6,7,8-tetrahydronaphthalene-1,6-diol 2-Fluoro-3,8,8-trimethyl-5-(naphthalen-1-ylamino 6-(trifluoromethyl)-5,6,7,8-tetrahydronaphthalene-1,6-diol 2-Chloro-3,8,8-trimethyl-5-(6-hydroxynaphthalen-1-ylamino)-6-(trifluoromethyl)-5,6,7,8-tetrahydronaphthalene-1,6-diol 2-Fluoro-3,8,8-trimethyl-5-(6-hydroxynaphthalen-1-ylamino)-6-(trifluoromethyl)-5,6,7,8-tetrahydronaphthalene-1,6-diol 2-Chloro-3,8,8-trimethyl-5-(5-hydroxynaphthalen-1-ylamino)-6-(trifluoromethyl)-5,6,7,8-tetrahydronaphthalene-1,6-diol 2-Fluoro-3,8,8-trimethyl-5-(5-hydroxynaphthalen-1-ylamino)-6-(trifluoromethyl)-5,6,7,8-tetrahydronaphthalene-1,6-diol 1,6-Dihydroxy-8,8-dimethyl-5-(2-methylquinazolin-5-ylamino)-6-(trifluoromethyl)-5,6,7,8-tetrahydronaphthalene-2-carbonitrile 1,6-Dihydroxy-8,8-dimethyl-5-(2-ethylquinazolin-5-ylamino)-6-(trifluoromethyl)-5,6,7,8-tetrahydronaphthalene-2-carbonitrile 1,6-Dihydroxy-8,8-dimethyl-5-(7-fluoro-2-methylquinazolin-5-ylamino)-6-(trifluoromethyl)-5,6,7,8-tetrahydronaphthalene-2-carbonitrile 1,6-Dihydroxy-8,8-dimethyl-5-(7,8-difluoro-2-methylquinazolin-5-ylamino)-6-(trifluoromethyl)-5,6,7,8-tetrahydronaphthalene-2-carbonitrile 1,6-Dihydroxy-8,8-dimethyl-5-(8-fluoro-2-methylquinazolin-5-ylamino) 6-(trifluoromethyl)-5,6,7,8-tetrahydronaphthalene-2-carbonitrile 1,6-Dihydroxy-8,8-dimethyl-5-(2-oxo-1,2-dihydroquinolin-5-ylamino)-6-(trifluoromethyl)-5,6,7,8-tetrahydronaphthalene-2-carbonitrile The entire disclosures of all applications, patents and publications, cited herein and of corresponding German Application No. 10 2004 017 662.0, filed Oct. 8, 2003 are incorporated by reference herein.

The invention claimed is:
1. Stereoisomers of general formula (I)

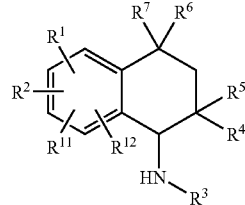

in which
R$^1$ and R$^2$, independently of one another, mean a hydrogen atom, a hydroxy group, a halogen atom, an optionally substituted (C$_1$-C$_{10}$)-alkyl group, an optionally substituted (C$_1$-C$_{10}$)-alkoxy group, a (C$_1$-C$_{10}$)-alkylthio group, a (C$_1$-C$_5$)-perfluoroalkyl group, a cyano group, or a nitro group,
or R$^1$ and R$^2$ together mean a group that is —O—(CH$_2$)$_n$—O—, —O—(CH$_2$)$_n$—CH$_2$—, —O—CH═CH—, —(CH$_2$)$_{n+2}$—, —NH—(CH$_2$)$_{n+1}$, N(C$_1$-C$_3$-alkyl)-(CH$_2$)$_{n+1}$, or —NH—N═CH—,
wherein n=1 or 2, and the terminal oxygen atoms and/or carbon atoms and/or nitrogen atoms are linked to directly adjacent ring-carbon atoms, or NR$^8$R$^9$,
wherein R$^8$ and R$^9$, independently of one another, are hydrogen, C$_1$-C$_5$-alkyl or (CO)—C$_1$-C$_5$-alkyl,
R$^{11}$ means a hydrogen atom, a hydroxy group, a halogen atom, a cyano group, an optionally substituted (C$_1$-C$_{10}$)-alkyl group, a (C$_1$-C$_{10}$)-alkoxy group, a (C$_1$-C$_{10}$)-alkylthio group, or a (C$_1$-C$_5$)-perfluoroalkyl group,
R$^{12}$ means a hydrogen atom, a hydroxy group, a halogen atom, a cyano group, an optionally substituted (C$_1$-C$_{10}$)-alkyl group, or a (C$_1$-C$_{10}$)-alkoxy group,
R$^3$ means a C$_1$-C$_{10}$-alkyl group that optionally is substituted by 1-3 hydroxy groups, halogen atoms, 1-3 (C$_1$-C$_5$)-alkoxy groups; an optionally substituted (C$_3$-C$_7$)-cycloalkyl group, an optionally substituted heterocyclyl group, an optionally substituted aryl group, a monocyclic or bicyclic heteroaryl group that optionally contains 1-4 nitrogen atoms and/or 1-2 oxygen atoms and/or 1-2 sulfur atoms and/or 1-2 keto groups and that optionally is substituted, independently of one another, by one or more groups selected from (C$_1$-C$_5$)-alkyl groups (which optionally is substituted by 1-3 hydroxy groups or 1-3 COOR$^{13}$ groups, wherein R$^{13}$ means hydrogen or (C$_1$-C$_5$)-alkyl); (C$_1$-C$_5$)-alkoxy groups, halogen atoms, hydroxy groups, NR$^8$R$^9$ groups, exomethylene groups, or oxygen, wherein this group can be linked via any position to the amine of the tetrahydronaphthalene system and optionally is hydrogenated at one or more locations,
R$^4$ means a hydroxy group, a group OR$^{10}$, or an O(CO)R$^{10}$ group, wherein R$^{10}$ means any hydroxy protective group or a C$_1$-C$_{10}$-alkyl group,
R$^5$ means a (C$_1$-C$_{10}$)-alkyl group or an optionally partially or completely fluorinated (C$_1$-C$_{10}$)-alkyl group, a (C$_3$-C$_7$)cycloalkyl group, a (C$_1$-C$_8$)alkyl(C$_3$-C$_7$)cycloalkyl group, a (C$_2$-C$_8$)alkenyl(C$_3$-C$_7$)cycloalkyl group, a heterocyclyl group, a (C$_1$-C$_8$)alkylheterocyclyl group, a (C$_2$-C$_8$)-alkenylheterocyclyl group, an aryl group, a (C$_1$-C$_8$)alkylaryl group, a (C$_2$-C$_8$)alkenylaryl group, (C$_2$-C$_8$)alkinylaryl groups, a monocyclic or bicyclic heteroaryl group that contains 1-3 nitrogen atoms and/or 1-2 oxygen atoms and/or 1-2 sulfur atoms and that optionally is substituted by 1-2 keto groups, 1-2 ($C_1$-$C_5$)-alkyl groups, 1-2 ($C_1$-$C_5$)-alkoxy groups, 1-3 halogen atoms or 1-2 exomethylene groups; a ($C_1$-$C_8$)alkylheteroaryl group or a ($C_2$-$C_8$)alkenylheteroaryl group, or a ($C_2$-$C_8$)alkinylheteroaryl group, wherein these groups can be linked via any position to the tetrahydronaphthalene system and optionally is hydrogenated at one or more locations, $R^6$ and $R^7$, independently of one another, mean a hydrogen atom, a methyl or ethyl group or together with the carbon atom of the tetrahydronaphthalene system mean a ($C_3$-$C_6$)-cycloalkyl ring, provided that at least three of radicals $R^1$, $R^2$, $R^{11}$ and $R^{12}$ are not hydrogen, or a pharmaceutically acceptable salt thereof.

2. Stereoisomers of general formula (I) according to claim 1, in which $R^1$ and $R^2$, independently of one another, mean a hydrogen atom, a hydroxy group, a halogen atom, an optionally substituted ($C_1$-$C_{10}$)-alkyl group, a ($C_1$-$C_{10}$)-alkoxy group, a ($C_1$-$C_{10}$)-alkylthio group, a ($C_1$-$C_5$)-perfluoroalkyl group, a cyano group, or a nitro group, or $R^1$ and $R^2$ together mean a group that is selected from the groups —O—$(CH_2)_n$—O—, —O—$(CH_2)_n$—$CH_2$—, —O—CH=CH—, —$(CH_2)_{n+2}$—, —NH—$(CH_2)_{n+1}$—, —N($C_1$-$C_3$-alkyl)-$(CH_2)_{n+1}$—, and —NH—N=CH—, wherein n=1 or 2, and the terminal oxygen atoms and/or carbon atoms and/or nitrogen atoms are linked to directly adjacent ring-carbon atoms, or $NR^8R^9$, wherein $R^8$ and $R^9$, independently of one another, are hydrogen, $C_1$-$C_5$-alkyl or (CO)—$C_1$-$C_5$-alkyl, $R^{11}$ means a hydrogen atom, a hydroxy group, a halogen atom, a cyano group, an optionally substituted ($C_1$-$C_{10}$)-alkyl group, a ($C_1$-$C_{10}$)-alkoxy group, a ($C_1$-$C_{10}$)-alkylthio group, or a ($C_1$-$C_5$)-perfluoroalkyl group, $R^{12}$ means a hydrogen atom, a hydroxy group, a halogen atom, a cyano group, an optionally substituted ($C_1$-$C_{10}$)-alkyl group, or a ($C_1$-$C_{10}$)-alkoxy group, $R^3$ means a $C_1$-$C_{10}$-alkyl group that optionally is substituted by 1-3 hydroxy groups, halogen atoms, or 1-3 ($C_1$-$C_5$)-alkoxy groups; an optionally substituted ($C_3$-$C_7$)-cycloalkyl group, an optionally substituted heterocyclyl group, an optionally substituted aryl group, a monocyclic or bicyclic heteroaryl group that optionally contains 1-3 nitrogen atoms and/or 1-2 oxygen atoms and/or 1-2 sulfur atoms and/or 1-2 keto groups and that optionally is substituted by one or more groups that are selected from ($C_1$-$C_5$)-alkyl groups (which optionally is substituted by 1-3 hydroxy groups or 1-3 $COOR^{13}$ groups, wherein $R^{13}$ means hydrogen or ($C_1$-$C_5$)-alkyl); ($C_1$-$C_5$)-alkoxy groups, halogen atoms, or exomethylene groups, wherein this group can be linked via any position to the amine of the tetrahydronaphthalene system and optionally is hydrogenated at one or more locations, $R^4$ means a hydroxy group, a group $OR^{10}$ or an $O(CO)R^{10}$ group, wherein $R^{10}$ means any hydroxy protective group or a $C_1$-$C_{10}$-alkyl group, $R^5$ means a ($C_1$-$C_5$)-alkyl group or an optionally partially or completely fluorinated ($C_1$-$C_5$)-alkyl group, a ($C_3$-$C_7$)cycloalkyl group, a ($C_1$-$C_8$)alkyl($C_3$-$C_7$)cycloalkyl group, a ($C_2$-$C_8$)alkenyl($C_3$-$C_7$)cycloalkyl group, a heterocyclyl group, a ($C_1$-$C_8$)alkylheterocyclyl group, a ($C_2$-$C_8$)-alkenylheterocyclyl group, ($C_2$-$C_8$)alkinylaryl groups, an aryl group, a ($C_1$-$C_8$)alkylaryl group, a ($C_2$-$C_8$)alkenylaryl group, a monocyclic or bicyclic heteroaryl group that contains 1-3 nitrogen atoms and/or 1-2 oxygen atoms and/or 1-2 sulfur atoms and that optionally is substituted by 1-2 keto groups, 1-2 ($C_1$-$C_5$)-alkyl groups, 1-2 ($C_1$-$C_5$)-alkoxy groups, 1-3 halogen atoms, or 1-2 exomethylene groups; a ($C_1$-$C_8$)alkylheteroaryl group or a ($C_2$-$C_8$)alkenylheteroaryl group, wherein these groups are linked via any position to the tetrahydronaphthalene system and optionally are hydrogenated at one or more locations, $R^6$ and $R^7$, independently of one another, mean a hydrogen atom, a methyl or ethyl group or together with the carbon atom of the tetrahydronaphthalene system mean a ($C_3$-$C_6$)-cycloalkyl ring, provided that at least three of radicals $R^1$, $R^2$, $R^{11}$ and $R^{12}$ are not hydrogen.

3. Stereoisomers of general formula (I) according to claim 2, in which $R^1$ and $R^2$, independently of one another, mean a hydrogen atom, a hydroxy group, a halogen atom, an optionally substituted ($C_1$-$C_{10}$)-alkyl group, an optionally substituted ($C_1$-$C_{10}$)-alkoxy group, a ($C_1$-$C_{10}$)-alkylthio group, a ($C_1$-$C_5$)-perfluoroalkyl group, a cyano group, or a nitro group, or $R^1$ and $R^2$ together mean a group that is selected from the groups —O—$(CH_2)_n$—O—, —O—$(CH_2)_n$—$CH_2$—, —O—CH=CH—, —$(CH_2)_{n+2}$—, —NH—$(CH_2)_{n+1}$—, —N($C_1$-$C_3$-alkyl)-$(CH_2)_{n+1}$—, and —NH—N=CH—, wherein n=1 or 2, and the terminal oxygen atoms and/or carbon atoms and/or nitrogen atoms are linked to directly adjacent ring-carbon atoms, or $NR^8R^9$, wherein $R^8$ and $R^9$, independently of one another, are hydrogen, $C_1$-$C_5$-alkyl, or (CO)—$C_1$-$C_5$-alkyl, $R^{11}$ means a hydrogen atom, a hydroxy group, a halogen atom, a cyano group, an optionally substituted ($C_1$-$C_{10}$)-alkyl group, a ($C_1$-$C_{10}$)-alkoxy group, a ($C_1$-$C_{10}$)-alkylthio group, or a ($C_1$-$C_5$)-perfluoroalkyl group, $R^{12}$ means a hydrogen atom, a hydroxy group, a halogen atom, a cyano group, an optionally substituted ($C_1$-$C_{10}$)-alkyl group, or a ($C_1$-$C_{10}$)-alkoxy group, $R^3$ means a $C_1$-$C_{10}$-alkyl group that optionally is substituted by 1-3 hydroxy groups, halogen atoms, 1-3 ($C_1$-$C_5$)-alkoxy groups, an optionally substituted ($C_3$-$C_7$)-cycloalkyl group, an optionally substituted heterocyclyl group, an optionally substituted aryl group, a monocyclic or bicyclic heteroaryl group that optionally contains 1-3 nitrogen atoms and/or 1-2 oxygen atoms and/or 1-2 sulfur atoms and/or 1-2 keto groups and that optionally is substituted, independently of one another, by one or more groups selected from ($C_1$-$C_5$)-alkyl groups (which optionally is substituted by 1-3 hydroxy groups or 1-3 $COOR^{13}$ groups, wherein $R^{13}$ means hydrogen or ($C_1$-$C_5$)-alkyl); ($C_1$-$C_5$)-alkoxy groups, halogen atoms, hydroxy groups, $NR^8R^9$ groups, exomethylene groups, or oxygen, wherein this group can be linked via any position to the amine of the tetrahydronaphthalene system and optionally is hydrogenated at one or more locations, $R^4$ means a hydroxy group, a group $OR^{10}$ or an $O(CO)R^{10}$ group, wherein $R^{10}$ means any hydroxy protective group or a $C_1$-$C_{10}$-alkyl group, R⁵ means a $(C_1-C_{10})$-alkyl group or an optionally partially or completely fluorinated $(C_1-C_{10})$-alkyl group, R⁶ and R⁷, independently of one another, mean a hydrogen atom, a methyl or ethyl group, or together with the carbon atom of the tetrahydronaphthalene system mean a $(C_3-C_6)$-cycloalkyl ring, provided that at least three of radicals R¹, R², R¹¹ and R¹² are not hydrogen.

4. Stereoisomers of general formula (I),

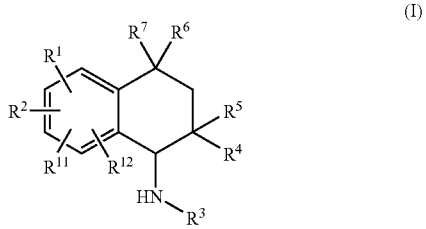

(I)

in which

R¹ and R², independently of one another, mean a hydrogen atom, a hydroxy group, a halogen atom, an optionally substituted $(C_1-C_{10})$-alkyl group, a $(C_1-C_{10})$-alkoxy group, a $(C_1-C_{10})$-alkylthio group, a $(C_1-C_5)$-perfluoroalkyl group, a cyano group, or a nitro group, or R¹ and R² together mean a group that is selected from the groups —O—(CH₂)ₙ—O—, —O—(CH₂)ₙ—CH₂—, —O—CH=CH—, —(CH₂)ₙ₊₂—, —NH—(CH₂)ₙ₊₁, —N(C₁-C₃-alkyl)-(CH₂)ₙ₊₁, and —NH—N=CH—, wherein n=1 or 2, and the terminal oxygen atoms and/or carbon atoms and/or nitrogen atoms are linked to directly adjacent ring-carbon atoms, or NR⁸R⁹, wherein R⁸ and R⁹, independently of one another, are hydrogen, C₁-C₅-alkyl, or (CO)—C₁-C₅-alkyl, R¹¹ means a hydrogen atom, a hydroxy group, a halogen atom, a cyano group, an optionally substituted $(C_1-C_{10})$-alkyl group, a $(C_1-C_{10})$-alkoxy group, a $(C_1-C_{10})$-alkylthio group, or a $(C_1-C_5)$-perfluoroalkyl group, R¹² means a hydrogen atom, a hydroxy group, a halogen atom, a cyano group, an optionally substituted $(C_1-C_{10})$-alkyl group, or a $(C_1-C_{10})$-alkoxy group, R³ means a C₁-C₁₀-alkyl group that optionally is substituted by a group that is selected from 1-3 hydroxy groups, halogen atoms, 1-3 $(C_1-C_5)$-alkoxy groups, an optionally substituted $(C_3-C_7)$-cycloalkyl group, an optionally substituted heterocyclyl group, an optionally substituted aryl group, a monocyclic or bicyclic heteroaryl group that optionally contains 1-3 nitrogen atoms and/or 1-2 oxygen atoms and/or 1-2 sulfur atoms and/or 1-2 keto groups and that optionally is substituted by one or more groups selected from $(C_1-C_5)$-alkyl groups (which optionally is substituted by 1-3 hydroxy groups or 1-3 COOR¹³ groups); $(C_1-C_5)$-alkoxy groups, halogen atoms, or exomethylene groups, wherein this group can be linked via any position to the amine of the tetrahydronaphthalene system and optionally is hydrogenated at one or more locations, R⁴ means a hydroxy group, a group OR¹⁰ or an O(CO)R¹⁰ group, wherein R¹⁰ means any hydroxy protective group or a C₁-C₁₀-alkyl group, R⁵ means a $(C_1-C_{10})$-alkyl group or an optionally partially or completely fluorinated $(C_1-C_5)$-alkyl group, a $(C_3-C_7)$cycloalkyl group, a $(C_1-C_8)$alkyl$(C_3-C_7)$cycloalkyl group, a $(C_2-C_8)$alkenyl$(C_3-C_7)$cycloalkyl group, a heterocyclyl group, a $(C_1-C_8)$alkylheterocyclyl group, a $(C_2-C_8)$-alkenylheterocyclyl group, an aryl group, a $(C_1-C_8)$alkylaryl group, a $(C_2-C_8)$alkenylaryl group, $(C_2-C_8)$alkinylaryl groups, a monocyclic or bicyclic heteroaryl group that contains 1-3 nitrogen atoms and/or 1-2 oxygen atoms and/or 1-2 sulfur atoms and that optionally is substituted by 1-2 keto groups, 1-2 $(C_1-C_5)$-alkyl groups, 1-2 $(C_1-C_5)$-alkoxy groups, 1-3 halogen atoms, or 1-2 exomethylene groups; a $(C_1-C_8)$alkylheteroaryl group or a $(C_2-C_8)$alkenylheteroaryl group, wherein these groups are linked via any position to the tetrahydronaphthalene system and optionally are hydrogenated at one or more locations, R⁶ and R⁷, independently of one another, mean a hydrogen atom, a methyl or ethyl group, or together with the carbon atom of the tetrahydronaphthalene system mean a $(C_3-C_6)$-cycloalkyl ring, provided that at least three of radicals R¹, R², R¹¹ and R¹² are not hydrogen, or a pharmaceutically acceptable salt thereof.

5. Stereoisomers of general formula (I) according to claim 4,

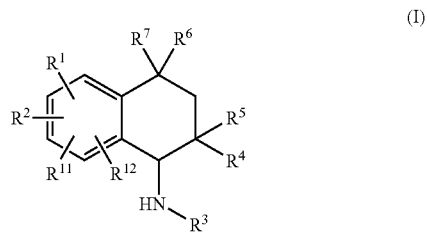

(I)

in which

R¹ and R², independently of one another, mean a hydrogen atom, a hydroxy group, a halogen atom, a $(C_1-C_{10})$-alkyl group, a $(C_1-C_{10})$-alkoxy group, a $(C_1-C_{10})$-alkylthio group, a $(C_1-C_5)$-perfluoroalkyl group, a cyano group, a nitro group, or R¹ and R² together mean a group that is —O—(CH₂)ₙ—O—, —O—(CH₂)ₙ—CH₂—, —O—CH=CH—, or —(CH₂)ₙ₊₂—, wherein n=1 or 2, and the terminal oxygen atoms and/or carbon atoms are linked to directly adjacent ring-carbon atoms, or NR⁸R⁹, wherein R⁸ and R⁹, independently of one another, are hydrogen, C₁-C₅-alkyl or (CO)—C₁-C₅-alkyl, R¹¹ means a hydrogen atom, a hydroxy group, a halogen atom, a cyano group, an optionally substituted $(C_1-C_{10})$-alkyl group, a $(C_1-C_{10})$-alkoxy group, a $(C_1-C_{10})$-alkylthio group, or a $(C_1-C_5)$-perfluoroalkyl group, R¹² means a hydrogen atom, a hydroxy group, a halogen atom, a cyano group, an optionally substituted $(C_1-C_{10})$-alkyl group, or a $(C_1-C_{10})$-alkoxy group, R³ means a C₁-C₁₀-alkyl group, which optionally is substituted by a group that is selected from 1-3 hydroxy groups, halogen atoms and 1-3 $(C_1-C_5)$-alkoxy groups, an optionally substituted phenyl group or a naphthyl group, a monocyclic or bicyclic heteroaryl group that contains 1-3 nitrogen atoms and/or 1-2 oxygen atoms and/or 1-2 sulfur atoms and that optionally is substituted by 1-2 keto groups, 1-2 ($C_1$-$C_5$)-alkyl groups, 1-2 ($C_1$-$C_5$)-alkoxy groups, 1-3 halogen atoms, or 1-2 exomethylene groups,
wherein these groups are linked via any position to the amine of the tetrahydronaphthalene system and optionally are hydrogenated at one or more locations,
$R^4$ means a hydroxy group,
$R^5$ means a ($C_1$-$C_5$)-alkyl group or an optionally partially or completely fluorinated ($C_1$-$C_5$)-alkyl group, an aryl group, a ($C_1$-$C_8$)alkylaryl group, a ($C_2$-$C_8$)alkenylaryl group, a ($C_3$-$C_7$)cycloalkyl group, a ($C_1$-$C_8$)alkyl($C_3$-$C_7$)cycloalkyl group, or a ($C_2$-$C_8$)alkenyl($C_3$-$C_7$)cycloalkyl group,
$R^6$ and $R^7$, independently of one another, mean a hydrogen atom, a methyl or ethyl group, or together with the carbon atom of the tetrahydronaphthalene system mean a ($C_3$-$C_6$)-cycloalkyl ring,
provided that at least three of radicals $R^1$, $R^2$, $R^{11}$ and $R^{12}$ are not hydrogen.

6. Stereoisomers of general formula (I) according to claim 4,

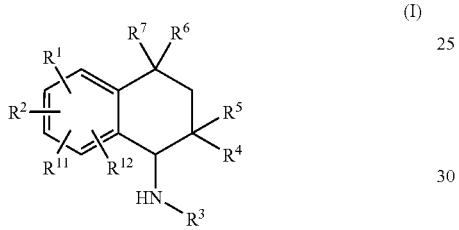

(I)

in which
$R^1$ and $R^2$, independently of one another, mean a hydrogen atom, a hydroxy group, a halogen atom, a ($C_1$-$C_{10}$)-alkyl group, a ($C_1$-$C_{10}$)-alkoxy group, a ($C_1$-$C_{10}$)-alkylthio group, a ($C_1$-$C_5$)-perfluoroalkyl group, a cyano group, a nitro group, or $R^1$ and $R^2$ together mean a group that is —O—$(CH_2)_n$—O—, —O—$(CH_2)_n$—$CH_2$—, —O—CH=CH—, or —$(CH_2)_{n+2}$—,
wherein n=1 or 2, and the terminal oxygen atoms and/or carbon atoms are linked to directly adjacent ring-carbon atoms,
or $NR^8R^9$,
wherein $R^8$ and $R^9$, independently of one another, are hydrogen, $C_1$-$C_5$-alkyl or (CO)—$C_1$-$C_5$-alkyl,
$R^{11}$ means a hydrogen atom, a hydroxy group, a halogen atom, a cyano group, an optionally substituted ($C_1$-$C_{10}$)-alkyl group, a ($C_1$-$C_{10}$)-alkoxy group, a ($C_1$-$C_{10}$-alkylthio group, or a ($C_1$-$C_5$)-perfluoroalkyl group,
$R^{12}$ means a hydrogen atom, a hydroxy group, a halogen atom, a cyano group, an optionally substituted ($C_1$-$C_{10}$)-alkyl group, or a ($C_1$-$C_{10}$)-alkoxy group,
$R^3$ means a $C_1$-$C_{10}$-alkyl group that optionally is substituted by a group that is selected from 1-3 hydroxy groups, halogen atoms, and 1-3 ($C_1$-$C_5$)-alkoxy groups, an optionally substituted phenyl group,
a monocyclic or bicyclic heteroaryl group that contains 1-3 nitrogen atoms and/or 1-2 oxygen atoms and/or 1-2 sulfur atoms and that optionally is substituted by 1-2 keto groups, 1-2 ($C_1$-$C_5$)-alkyl groups, 1-2 ($C_1$-$C_5$)-alkoxy groups, 1-3 halogen atoms, or 1-2 exomethylene groups,
wherein these groups can be linked via any position to the amine of the tetrahydronaphthalene system and optionally are hydrogenated at one or more locations,
$R^4$ means a hydroxy group,
$R^5$ means a ($C_1$-$C_5$)-alkyl group or an optionally partially or completely fluorinated ($C_1$-$C_5$)-alkyl group, an aryl group, a ($C_1$-$C_8$)alkylaryl group, a ($C_2$-$C_8$)alkenylaryl group, a ($C_3$-$C_7$)cycloalkyl group, a ($C_1$-$C_8$)alkyl($C_3$-$C_7$)cycloalkyl group, or a ($C_2$-$C_8$)alkenyl($C_3$-$C_7$)cycloalkyl group,
$R^6$ and $R^7$, independently of one another, mean a hydrogen atom, a methyl or ethyl group, or together with the carbon atom of the tetrahydronaphthalene system mean a ($C_3$-$C_6$)-cycloalkyl ring,
provided that at least three of radicals $R^1$, $R^2$, $R^{11}$ and $R^{12}$ are not hydrogen.

7. Stereoisomers of general formula (I) according to claim 4,

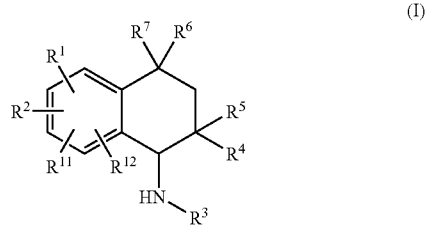

(I)

in which
$R^1$ and $R^2$, independently of one another, mean a hydrogen atom, a hydroxy group, a halogen atom, a ($C_1$-$C_{10}$)-alkyl group, a ($C_1$-$C_{10}$)-alkoxy group, a ($C_1$-$C_{10}$)-alkylthio group, a ($C_1$-$C_5$)-perfluoroalkyl group, a cyano group, or a nitro group, or $R^1$ and $R^2$ together mean a group that is —O—$(CH_2)_n$—O—, —O—$(CH_2)_n$—$CH_2$—, —O—CH=CH—, or —$(CH_2)_{n+2}$—,
wherein n=1 or 2, and the terminal oxygen atoms and/or carbon atoms are linked to directly adjacent ring-carbon atoms,
or $NR^8R^9$,
wherein $R^8$ and $R^9$, independently of one another, are hydrogen, $C_1$-$C_5$-alkyl or (CO)—$C_1$-$C_5$-alkyl,
$R^{11}$ means a hydrogen atom, a hydroxy group, a halogen atom, a cyano group, an optionally substituted ($C_1$-$C_{10}$)-alkyl group, a ($C_1$-$C_{10}$)-alkoxy group, a ($C_1$-$C_{10}$)-alkylthio group, or a ($C_1$-$C_5$)-perfluoroalkyl group,
$R^{12}$ means a hydrogen atom, a hydroxy group, a halogen atom, a cyano group, an optionally substituted ($C_1$-$C_{10}$)-alkyl group, or a ($C_1$-$C_{10}$)-alkoxy group,
$R^3$ means a $C_1$-$C_{10}$-alkyl group, which optionally is substituted by a group that is selected from 1-3 hydroxy groups, halogen atoms, and 1-3 ($C_1$-$C_5$)-alkoxy groups, an optionally substituted phenyl group,
a monocyclic or bicyclic heteroaryl group that contains 1-3 nitrogen atoms and/or 1-2 oxygen atoms and/or 1-2 sulfur atoms and that optionally is substituted by 1-2 keto groups, 1-2 ($C_1$-$C_5$)-alkyl groups, 1-2 ($C_1$-$C_5$)-alkoxy groups, 1-3 halogen atoms, or 1-2 exomethylene groups,
wherein these groups can be linked via any position to the amine of the tetrahydronaphthalene system and optionally are hydrogenated at one or more locations,
$R^4$ means a hydroxy group,
$R^5$ means a ($C_1$-$C_5$)-alkyl group or an optionally partially or completely fluorinated ($C_1$-$C_5$)-alkyl group, an aryl group, a ($C_1$-$C_8$)alkylaryl group, a ($C_2$-$C_8$)alkenylaryl group, a $(C_3-C_7)$cycloalkyl group, a $(C_1-C_8)$alkyl$(C_3-C_7)$cycloalkyl group, or a $(C_2-C_8)$alkenyl$(C_3-C_7)$cycloalkyl group, $R^6$ and $R^7$, independently of one another, mean a hydrogen atom, a methyl or ethyl group, or together with the carbon atom of the tetrahydronaphthalene system mean a $(C_3-C_6)$-cycloalkyl ring, provided that at least three of radicals $R^1$, $R^2$, $R^{11}$ and $R^{12}$ are not hydrogen.

8. Stereoisomers of general formula (I) according to claim 4,

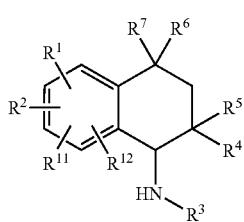

(I)

in which $R^1$ and $R^2$, independently of one another, mean a hydrogen atom, a hydroxy group, a halogen atom, a $(C_1-C_5)$-alkyl group, a $(C_1-C_5)$-alkoxy group, a $(C_1-C_5)$-perfluoroalkyl group, a cyano group, or $R^1$ and $R^2$ together mean a group that is —O—$(CH_2)_n$—O—, —O—$(CH_2)_n$—$CH_2$—, —O—CH=CH—, or —$(CH_2)_{n+2}$—, wherein n=1 or 2, and the terminal oxygen atoms and/or carbon atoms are linked to directly adjacent ring-carbon atoms, $R^{11}$ means a hydrogen atom, a hydroxy group, a halogen atom, a cyano group, an optionally substituted $(C_1-C_{10})$-alkyl group, a $(C_1-C_{10})$-alkoxy group, a $(C_1-C_{10})$-alkylthio group, or a $(C_1-C_5)$-perfluoroalkyl group, $R^{12}$ means a hydrogen atom, a hydroxy group, a halogen atom, a cyano group, an optionally substituted $(C_1-C_{10})$-alkyl group, or a $(C_1-C_{10})$-alkoxy group, $R^3$ means a $C_1-C_{10}$-alkyl group, which optionally is substituted by 1-3 hydroxy groups, halogen atoms, a phenyl, phthalidyl, isoindolyl, dihydroindolyl, dihydroisoindolyl, dihydroisoquinolinyl, thiophthalidyl, benzoxazinonyl, phthalazinonyl, quinolinyl, isoquinolinyl, quinolonyl, isoquinolonyl, indazolyl, benzothiazolyl, quinazolinyl, quinoxalinyl, cinnolinyl, phthalazinyl, 1,7- or 1,8-naphthyridinyl, dihydroindolonyl, dihydroisoindolonyl, benzimidazolyl or indolyl group that optionally is substituted with $C_1-C_5$-alkyl, halogen, hydroxy, or $C_1-C_5$-alkoxy, wherein these groups can be linked via any position to the amine of the tetrahydronaphthalene system and optionally are substituted in one or more places with 1-2 keto groups, 1-2 $(C_1-C_3)$-alkyl groups, 1-2 $(C_1-C_3)$-alkoxy groups, 1-3 halogen atoms, or 1-2 exomethylene groups, and optionally are hydrogenated at one or more locations, $R^4$ means a hydroxy group, $R^5$ means a $(C_1-C_5)$-alkyl group or an optionally partially or completely fluorinated $(C_1-C_5)$-alkyl group, $R^6$ and $R^7$, independently of one another, mean a hydrogen atom, a methyl or ethyl group or together with the carbon atom of the tetrahydronaphthalene system mean a $(C_3-C_6)$-cycloalkyl ring, provided that at least three of radicals $R^1$, $R^2$, $R^{11}$ and $R^{12}$ are not hydrogen.

9. Stereoisomers of general formula (I) according to claim 4,

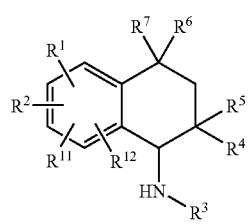

(I)

in which $R^1$ and $R^2$, independently of one another, mean a hydrogen atom, a hydroxy group, a halogen atom, a $(C_1-C_5)$-alkyl group, a $(C_1-C_5)$-perfluoroalkyl group, a cyano group, a $(C_1-C_5)$-alkoxy group, or together mean a $(C_1-C_2)$-alkylenedioxy group, wherein then $R^1$ and $R^2$ must be directly adjacent, $R^{11}$ means a hydrogen atom, a hydroxy group, a halogen atom, a cyano group, an optionally substituted $(C_1-C_{10})$-alkyl group, a $(C_1-C_{10})$-alkoxy group, a $(C_1-C_{10})$-alkylthio group, or a $(C_1-C_5)$-perfluoroalkyl group, $R^{12}$ means a hydrogen atom, a hydroxy group, a halogen atom, a cyano group, an optionally substituted $(C_1-C_{10})$-alkyl group, or a $(C_1-C_{10})$-alkoxy group, $R^3$ means a phenyl, phthalidyl, isoindolyl, dihydroindolyl, dihydroisoindolyl, dihydroisoquinolinyl, thiophthalidyl, benzoxazinonyl, phthalazinonyl, quinolinyl, isoquinolinyl, quinolonyl, isoquinolonyl, indazolyl, benzothiazolyl, quinazolinyl, quinoxalinyl, cinnolinyl, phthalazinyl, 1,7- or 1,8-naphthyridinyl, dihydroindolonyl, dihydroisoindolonyl, benzimidazolyl or indolyl group that optionally is substituted with $C_1-C_5$-alkyl, halogen, hydroxy, or $C_1-C_5$-alkoxy, wherein these groups can be linked via any position to the amine of the tetrahydronaphthalene system and optionally are substituted in one or more places with 1-2 keto groups, 1-2 $(C_1-C_3)$-alkyl groups, or 1-2 exomethylene groups, and optionally are hydrogenated at one or more locations, $R^4$ means a hydroxy group, $R^5$ means a $(C_1-C_5)$-alkyl group or an optionally partially or completely fluorinated $(C_1-C_5)$-alkyl group, $R^6$ and $R^7$, independently of one another, mean a hydrogen atom, a methyl or ethyl group or together with the carbon atom of the tetrahydronaphthalene system mean a $(C_3-C_6)$-cycloalkyl ring, provided that at least three of radicals $R^1$, $R^2$, $R^{11}$ and $R^{12}$ are not hydrogen.

10. A method for treating an inflammatory disease, comprising administering to a subject in need thereof an effective amount of stereoisomers of claim 4.

11. A method for treating an inflammatory disease, comprising administering to a subject in need thereof an effective amount of stereoisomers of claim 1.

12. A pharmaceutical composition comprising stereoisomers of claim 1 and a pharmaceutically acceptable carrier.

13. Process for the production of the stereoisomers of general formula I according to claim 1, comprising cyclizing stereoisomers of general formula II

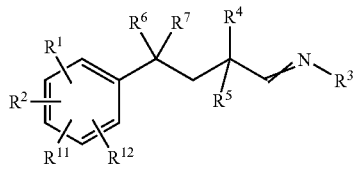

in which $R^1$, $R^2$, $R^{11}$, $R^{12}$, $R^3$, $R^4$, $R^5$, $R^6$ and $R^7$ have the meanings indicated for the compound of formula I,
with the addition of inorganic or organic aids or Lewis acids.

14. Stereoisomers of general formula I according to claim 1, in the form of a salt with physiologically compatible anions.

15. Stereoisomers of general formula II,

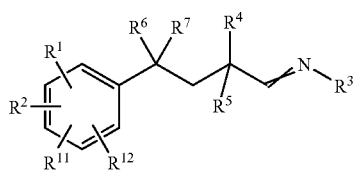

in which
$R^1$ and $R^2$, independently of one another, mean a hydrogen atom, a hydroxy group, a halogen atom, an optionally substituted $(C_1-C_{10})$-alkyl group, an optionally substituted $(C_1-C_{10})$-alkoxy group, a $(C_1-C_{10})$-alkylthio group, a $(C_1-C_5)$-perfluoroalkyl group, a cyano group, or a nitro group,
or $R^1$ and $R^2$ together mean a group that is —O—$(CH_2)_n$—O—, —O—$(CH_2)_n$—$CH_2$—, —O—CH=CH—, —$(CH_2)_{n+2}$—, —NH—$(CH_2)_{n+1}$, N($C_1$-$C_3$-alkyl)-$(CH_2)_{n+1}$, or —NH—N=CH—,
wherein n=1 or 2, and the terminal oxygen atoms and/or carbon atoms and/or nitrogen atoms are linked to directly adjacent ring-carbon atoms,
or $NR^8R^9$,
wherein $R^8$ and $R^9$, independently of one another, are hydrogen, $C_1$-$C_5$-alkyl or (CO)—$C_1$-$C_5$-alkyl,
$R^{11}$ means a hydrogen atom, a hydroxy group, a halogen atom, a cyano group, an optionally substituted $(C_1-C_{10})$-alkyl group, a $(C_1-C_{10})$-alkoxy group, a $(C_1-C_{10})$-alkylthio group, or a $(C_1-C_5)$-perfluoroalkyl group,
$R^{12}$ means a hydrogen atom, a hydroxy group, a halogen atom, a cyano group, an optionally substituted $(C_1-C_{10})$-alkyl group, or a $(C_1-C_{10})$-alkoxy group,
$R^3$ means a $C_1-C_{10}$-alkyl group that optionally is substituted by 1-3 hydroxy groups, halogen atoms, 1-3 $(C_1-C_5)$-alkoxy groups; an optionally substituted $(C_3-C_7)$-cycloalkyl group, an optionally substituted heterocyclyl group, an optionally substituted aryl group, a monocyclic or bicyclic heteroaryl group that optionally contains 1-4 nitrogen atoms and/or 1-2 oxygen atoms and/or 1-2 sulfur atoms and/or 1-2 keto groups and that optionally is substituted, independently of one another, by one or more groups selected from $(C_1-C_5)$-alkyl groups (which optionally is substituted by 1-3 hydroxy groups or 1-3 $COOR^{13}$ groups, wherein $R^{13}$ means hydrogen or $(C_1-C_5)$-alkyl); $(C_1-C_5)$-alkoxy groups, halogen atoms, hydroxy groups, $NR^8R^9$ groups, exomethylene groups, or oxygen, wherein this group can be linked via any position to the amine of the tetrahydronaphthalene system and optionally is hydrogenated at one or more locations,
$R^4$ means a hydroxy group, a group $OR^{10}$ or an $O(CO)R^{10}$ group, wherein $R^{10}$ means any hydroxy protective group or a $C_1-C_{10}$-alkyl group,
$R^5$ means a $(C_1-C_{10})$-alkyl group or an optionally partially or completely fluorinated $(C_1-C_{10})$-alkyl group, a $(C_3-C_7)$cycloalkyl group, a $(C_1-C_8)$alkyl$(C_3-C_7)$cycloalkyl group, a $(C_2-C_8)$alkenyl$(C_3-C_7)$cycloalkyl group, a heterocyclyl group, a $(C_1-C_8)$alkylheterocyclyl group, a $(C_2-C_8)$-alkenylheterocyclyl group, an aryl group, a $(C_1-C_8)$alkylaryl group, a $(C_2-C_8)$alkenylaryl group, $(C_2-C_8)$alkinylaryl groups,
a monocyclic or bicyclic heteroaryl group that contains 1-3 nitrogen atoms and/or 1-2 oxygen atoms and/or 1-2 sulfur atoms and that optionally is substituted by 1-2 keto groups, 1-2 $(C_1-C_5)$-alkyl groups, 1-2 $(C_1-C_5)$-alkoxy groups, 1-3 halogen atoms or 1-2 exomethylene groups; a $(C_1-C_8)$alkylheteroaryl group or a $(C_2-C_8)$alkenylheteroaryl group, or a $(C_2-C_8)$alkinylheteroaryl group, wherein these groups can be linked via any position to the tetrahydronaphthalene system and optionally is hydrogenated at one or more locations,
$R^6$ and $R^7$, independently of one another, mean a hydrogen atom, a methyl or ethyl group or together with the carbon atom of the tetrahydronaphthalene system mean a $(C_1-C_6)$-cycloalkyl ring,
provided that at least three of radicals $R^1$, $R^2$, $R^{11}$ and $R^{12}$ are not hydrogen.

16. Process for the production of the stereoisomers of general formula I according to claim 4, comprising cyclizing stereoisomers of general formula II

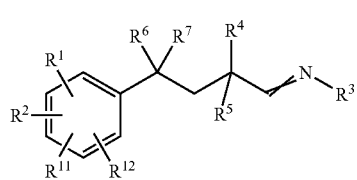

in which $R^1$, $R^2$, $R^{11}$, $R^{12}$, $R^3$, $R^4$, $R^5$, $R^6$ and $R^7$ have the meanings indicated for the compound of formula I,
with the addition of inorganic or organic aids or Lewis acids.

17. A pharmaceutical composition comprising stereoisomers of claim 4 and a pharmaceutically acceptable carrier.

18. Stereoisomers of general formula I according to claim 4, in the form of a salt with physiologically compatible anions.

* * * * *